US010184152B2

(12) United States Patent
O'Connell et al.

(10) Patent No.: US 10,184,152 B2
(45) Date of Patent: Jan. 22, 2019

(54) TRANSCRIPTIONAL SIGNATURE FOR CHLAMYDIAL PELVIC INFLAMMATORY DISEASE

(71) Applicant: University of Pittsburgh—Of the Commonwealth System of Higher Education, Pittsburgh, PA (US)

(72) Inventors: Catherine O'Connell, Chapel Hill, NC (US); Toni Darville, Chapel Hill, NC (US); Xiaojing Zheng, Chapel Hill, NC (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 15/304,836

(22) PCT Filed: Apr. 16, 2015

(86) PCT No.: PCT/US2015/026122
§ 371 (c)(1),
(2) Date: Oct. 17, 2016

(87) PCT Pub. No.: WO2015/161044
PCT Pub. Date: Oct. 22, 2015

(65) Prior Publication Data
US 2017/0183732 A1   Jun. 29, 2017

Related U.S. Application Data

(60) Provisional application No. 61/981,545, filed on Apr. 18, 2014.

(51) Int. Cl.
*C12Q 1/68* (2018.01)
*C12Q 1/6883* (2018.01)
*A61K 31/43* (2006.01)
*A61K 31/65* (2006.01)
*A61K 31/7048* (2006.01)
*A61K 31/7052* (2006.01)
*G01N 33/569* (2006.01)
*C12Q 1/689* (2018.01)

(52) U.S. Cl.
CPC ............ *C12Q 1/6883* (2013.01); *A61K 31/43* (2013.01); *A61K 31/65* (2013.01); *A61K 31/7048* (2013.01); *A61K 31/7052* (2013.01); *C12Q 1/689* (2013.01); *G01N 33/56927* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

2010/0292170 A1   11/2010   Reeder et al.

OTHER PUBLICATIONS

Enard et al. (Science 2002 vol. 296 p. 340) (Year: 2002).*
Cobb et al (Crit Care Med 2002 vol. 30 p. 2711) (Year: 2002).*
Darville et al., "Blood transcriptional profiling of women with Chlamydia trachomatis identifies a pelvic inflammatory disease (PID) signature," *Sexually Transmitted Infections* 89(Suppl.1): A27, Oral Sessions O01.4 (2013).
Duan et al., "Multiple SVM-RFE for gene selection in cancer classification with expression data," *IEEE trans nanobioscience* 4, 228-234 (2005).
Geisler, 2010. "Duration of untreated, uncomplicated *Chlamydia trachomatis* genital infection and factors associated with chlamydia resolution: A review of human studies," *J. Infect. Dis.* 201(Suppl 2): S104-S113 (2010).
Gottlieb et al., "Screening and treating *Chlamydia trachomatis* genital infection to prevent pelvic inflammatory disease: Interpretation of findings from randomized controlled trials," *Sexually Transmitted Diseases* 40(2): 97-102 (2013).
Guyon et al., "Gene selection for cancer classification using support vector machines," *Machine learning* 46: 389-422 (2002).
International Search Report from parent PCT Application No. PCT/US2015/026122, 5 pages (dated Jun. 18, 2015).
Judlin "Current concepts in managing pelvic inflammatory disease," *Curr. Opin. Infect. Dis.* 23: 83-87 (2010).
Kiviat et al., "Endometrial histopathology in patients with culture-proved upper genital tract infection and laparoscopically diagnosed acute salpingitis," *Am. J. Surg. Pathol.* 14: 167-175 (1990).
Rodrigues-Cerdeira et al., "Unveiling new molecular factors useful for detection of pelvic inflammatory disease due to *Chlamydia trachomatis* infection," *International Scholarly Research Network (ISRN) Obstetrics and Gynecology* (Article ID 581725) (internal pp. 1-7) (2012).
Scholes et al., "Prevention of pelvic inflammatory disease by screening for cervical chlamydial infection," *The New England Journal of Medicine* 334(21): 1362-1366 (1996).
Taylor et al., "Variants in toll-like receptor 1 and 4 genes are associated with *Chlamydia trachomatis* among women with pelvic inflammatory disease," *Journal of Infectious Diseases* 205(4): 603-609 (2012).
Wiesenfeld et al., "Subclinical pelvic inflammatory disease and infertility," *Obstet. Gynecol.* 120: 37-43 (2012).
Written Opinion from parent PCT Application No. PCT/US2015/026122, 6 pages (dated Jun. 18, 2015).

* cited by examiner

*Primary Examiner* — Katherine D Salmon
(74) *Attorney, Agent, or Firm* — Klarquist Sparkman, LLP

(57) ABSTRACT

Methods are provided herein for determining the likelihood that a subject, such as an asymptomatic subject, has chlamydial pelvic inflammatory disease. In some embodiments, the method can determine the likelihood that a pharmaceutical agent is effective for treating a subject that has chlamydial pelvic inflammatory disease. In other specific non-limiting examples, the method predicts endometritis and elevated pathogen burden. The subject is a female, such as a human female.

8 Claims, 2 Drawing Sheets

TRANSCRIPTIONAL SIGNATURE FOR CHLAMYDIAL PELVIC INFLAMMATORY DISEASE

CROSS REFERENCE TO RELATED APPLICATION

This is a § 371 U.S. national stage of International Application No. PCT/US2015/026122, filed Apr. 16, 2015, which was published in English under PCT Article 21(2), which claims the benefit of U.S. Application No. 61/981,545, filed on Apr. 18, 2014 which is incorporated herein by reference in its entirety.

ACKNOWLEDGMENT OF GOVERNMENT SUPPORT

This invention was made with government support under Grant Nos. A1084024-01 and A1098660 awarded by the National Institutes of Health. The government has certain rights in the invention.

FIELD OF THE DISCLOSURE

This relates to the field of pelvic inflammatory disease (PID), specifically to methods for determining if a subject has chlamydial pelvic inflammatory disease and/or determining if a subject is at risk for reproductive organ damage from a *chlamydia* infection.

BACKGROUND

Pelvic Inflammatory Disease (PID) poses an important risk to the reproductive health of women globally. In addition to costs associated with the treatment of symptomatic acute infection, women risk devastating long-term sequelae, including chronic pelvic pain, infertility and ectopic pregnancy. Asymptomatic infection is common and women who do not experience overt signs of illness remain at elevated risk for these morbidities. Genital tract infection caused by *C. trachomatis* and *N. gonorrhoeae* infections or co-infections exceed ~3.7 million cases annually in the US, with combined lifetime associated costs exceeding $678 million. Furthermore, many infections with *C. trachomatis* are asymptomatic. Infection with *C. trachomatis* is easily detected and treated but identification of women who are at elevated risk of reproductive sequelae has been impossible. It is estimated that ~80,000 of the ~4 million women diagnosed with chlamydial infection each year risk long-term reproductive sequelae. A need remains for methods to identify women at risk for silent disease.

SUMMARY

The disclosed methods utilize marker sets to identify subjects. In some embodiments, the methods include measuring the markers listed in Table A (TCL1A, HINT3, CDK5RAP3, FLJ35801, VPREB3, SULT1A1 (transcript variant 5), SULT1A1 (transcript variant 3), FCRLA, LOC100130562, SULT1A2, SLC4A1, LOC90925, MYOM2, CD19, LOC100132727) and Table B (LOC100008588, CDCA7, TATDN3, LOC648729, HIST1H4H, MCM4, LOC642678, RPS15A, CKS2, LIMS1, OSBPL8, GRB2, LOC441763, SPATA13, TPM4, MCTP1, SUMO3). In other embodiments, the methods include measuring the markers listed in Table C (MYOM2, SLC4A1, LOC402251, LOC286444, FBXO7, TCL1A, LOC100130562, C5ORF28, LOC642989, CD79B, LOC643873, LOC100129742, VPREB3, LOC100133372, RPL13, SULT1A1 (transcript variant 5), CD19, CD79B, LOC100133583, CCR6, LOC642934, LOC100132727, LOC90925, PPA2, LOC100130053, SULT1A4, FCRLA, CDC42, CERK, SDHALP1, LOC100129237, HINT3, SULT1A1 (transcript variant 3), SULT1A2, CMPK1, MEF2D, C10ORF104, JAK1, LOC644739, HS.552082, KCNH6, RPL37A, CDK5RAP3, and FLJ35801) and Table D (FBLN1, CKS2, C10ORF105, CDCA7, HS.489254, MAX, GINS2, MCM4, LOC648729, TATDN3, MYD88, LEPROT, LOC645159, MSRA, TPM4, NAT8B, RTP4, GRB2, SUMO3, RPS15A, MCTP1, LOC642678, PROS1, NFKBIZ, PARP12, OSBPL8, SPATA13, LIMS1, HEBP1, HIST1H4H, LOC441763, LY6E, and LOC100008588). In some embodiments, methods identify a female subject that has a *chlamydia* infection, and/or can be at risk of damage to a reproductive organ from a *chlamydia* infection, and/or that is amenable to treatment with certain pharmaceutical agents.

In some embodiments, a method is provided for detecting a chlamydial pelvic inflammatory disease in a female subject. The method includes performing one or more assays that detect a level of TCL1A, HINT3, CDK5RAP3, FLJ35801, VPREB3, SULT1A1 (transcript variant 5), SULT1A1 (transcript variant 3), FCRLA, LOC100130562, SULT1A2, SLC4A1, LOC90925, MYOM2, CD19, LOC100132727, LOC100008588, CDCA7, TATDN3, LOC648729, HIST1H4H, MCM4, LOC642678, RPS15A, CKS2, LIMS1, OSBPL8, GRB2, LOC441763, SPATA13, TPM4, MCTP1, and SUMO3 in a biological sample from the subject. The level of TCL1A, HINT3, CDK5RAP3, FLJ35801, VPREB3, SULT1A1 (transcript variant 5), SULT1A1 (transcript variant 3), FCRLA, LOC100130562, SULT1A2, SLC4A1, LOC90925, MYOM2, CD19, LOC100132727, LOC100008588, CDCA7, TATDN3, LOC648729, HIST1H4H, MCM4, LOC642678, RPS15A, CKS2, LIMS1, OSBPL8, GRB2, LOC441763, SPATA13, TPM4, MCTP1, and SUMO3 is compared to a respective control level of TCL1A, HINT3, CDK5RAP3, FLJ35801, VPREB3, SULT1A1 (transcript variant 5), SULT1A1 (transcript variant 3), FCRLA, LOC100130562, SULT1A2, SLC4A1, LOC90925, MYOM2, CD19, LOC100132727, LOC100008588, CDCA7, TATDN3, LOC648729, HIST1H4H, MCM4, LOC642678, RPS15A, CKS2, LIMS1, OSBPL8, GRB2, LOC441763, SPATA13, TPM4, MCTP1, and SUMO3, respectively. The detection of a decrease in the level of TCL1A, HINT3, CDK5RAP3, FLJ35801, VPREB3, SULT1A1 (transcript variant 5), SULT1A1 (transcript variant 3), FCRLA, LOC100130562, SULT1A2, SLC4A1, LOC90925, MYOM2, CD19, and LOC100132727, and an increase in the level of LOC100008588, CDCA7, TATDN3, LOC648729, HIST1H4H, MCM4, LOC642678, RPS15A, CKS2, LIMS1, OSBPL8, GRB2, LOC441763, SPATA13, TPM4, MCTP1, and SUMO3, as compared to the respective control indicates that the subject has chlamydial pelvic inflammatory disease.

In additional embodiments, the method includes performing one or more assays that detect a level of MYOM2, SLC4A1, LOC402251, LOC286444, FBXO7, TCL1A, LOC100130562, C5ORF28, LOC642989, CD79B, LOC643873, LOC100129742, VPREB3, LOC100133372, RPL13, SULT1A1 (transcript variant 5), CD19, CD79B, LOC100133583, CCR6, LOC642934, LOC100132727, LOC90925, PPA2, LOC100130053, SULT1A4, FCRLA, CDC42, CERK, SDHALP1, LOC100129237, HINT3, SULT1A1 (transcript variant 3), SULT1A2, CMPK1, MEF2D, C10ORF104, JAK1, LOC644739, HS.552082, KCNH6, RPL37A, CDK5RAP3, FLJ3580, FBLN1, CKS2, C10ORF105, CDCA7, HS.489254, MAX, GINS2, MCM4, LOC648729, TATDN3, MYD88, LEPROT, LOC645159, MSRA, TPM4, NAT8B, RTP4, GRB2, SUMO3, RPS15A, MCTP1, LOC642678, PROS1, NFKBIZ, PARP12, OSBPL8, SPATA13, LIMS1, HEBP1, HIST1H4H, LOC441763, LY6E, and LOC100008588 in a biological sample from the subject. The level of MYOM2, SLC4A1, LOC402251, LOC286444, FBXO7, TCL1A, LOC100130562, C5ORF28, LOC642989, CD79B, LOC643873, LOC100129742, VPREB3, LOC100133372, RPL13, SULT1A1 (transcript variant 5), CD19, CD79B, LOC100133583, CCR6, LOC642934, LOC100132727, LOC90925, PPA2, LOC100130053, SULT1A4, FCRLA, CDC42, CERK, SDHALP1, LOC100129237, HINT3, SULT1A1 (transcript variant 3), SULT1A2, CMPK1, MEF2D, C10ORF104, JAK1, LOC644739, HS.552082, KCNH6, RPL37A, CDK5RAP3, FLJ35801, CKS2, C10ORF105, CDCA7, HS.489254, MAX, GINS2, MCM4, LOC648729, TATDN3, MYD88, LEPROT, LOC645159, MSRA, TPM4, NAT8B, RTP4, GRB2, SUMO3, RPS15A, MCTP1, LOC642678, PROS1, NFKBIZ, PARP12, OSBPL8, SPATA13, LIMS1, HEBP1, HIST1H4H, LOC441763, LY6E, and LOC100008588 is compared to a respective control level of MYOM2, SLC4A1, LOC402251, LOC286444, FBXO7, TCL1A, LOC100130562, C5ORF28, LOC642989, CD79B, LOC643873, LOC100129742, VPREB3, LOC100133372, RPL13, SULT1A1 (transcript variant 5), CD19, CD79B, LOC100133583, CCR6, LOC642934, LOC100132727, LOC90925, PPA2, LOC100130053, SULT1A4, FCRLA, CDC42, CERK, SDHALP1, LOC100129237, HINT3, SULT1A1 (transcript variant 3), SULT1A2, CMPK1, MEF2D, C10ORF104, JAK1, LOC644739, HS.552082, KCNH6, RPL37A, CDK5RAP3, FLJ35801, CKS2, C10ORF105, CDCA7, HS.489254, MAX, GINS2, MCM4, LOC648729, TATDN3, MYD88, LEPROT, LOC645159, MSRA, TPM4, NAT8B, RTP4, GRB2, SUMO3, RPS15A, MCTP1, LOC642678, PROS1, NFKBIZ, PARP12, OSBPL8, SPATA13, LIMS1, HEBP1, HIST1H4H, LOC441763, LY6E, and LOC100008588. The detection of a decrease in the level of MYOM2, SLC4A1, LOC402251, LOC286444, FBXO7, TCL1A, LOC100130562, C5ORF28, LOC642989, CD79B, LOC643873, LOC100129742, VPREB3, LOC100133372, RPL13, SULT1A1 (transcript variant 5), CD19, CD79B, LOC100133583, CCR6, LOC642934, LOC100132727, LOC90925, PPA2, LOC100130053, SULT1A4, FCRLA, CDC42, CERK, SDHALP1, LOC100129237, HINT3, SULT1A1 (transcript variant 3), SULT1A2, CMPK1, MEF2D, C10ORF104, JAK1, LOC644739, HS.552082, KCNH6, RPL37A, CDK5RAP3, and FLJ35801, and an increase in the level of FBLN1, CKS2, C10ORF105, CDCA7, HS.489254, MAX, GINS2, MCM4, LOC648729, TATDN3, MYD88, LEPROT, LOC645159, MSRA, TPM4, NAT8B, RTP4, GRB2, SUMO3, RPS15A, MCTP1, LOC642678, PROS1, NFKBIZ, PARP12, OSBPL8, SPATA13, LIMS1, HEBP1, HIST1H4H, LOC441763, LY6E, and LOC100008588, as compared to the respective control indicates that the subject has chlamydial pelvic inflammatory disease.

In further embodiments, a method is provided for determining the likelihood that a female subject will develop damage to a reproductive organ after chlamydial infection, the method includes performing one or more assays that detect a level of TCL1A, HINT3, CDK5RAP3, FLJ35801, VPREB3, SULT1A1 (transcript variant 5), SULT1A1 (transcript variant 3), FCRLA, LOC100130562, SULT1A2, SLC4A1, LOC90925, MYOM2, CD19, LOC100132727, LOC100008588, CDCA7, TATDN3, LOC648729, HIST1H4H, MCM4, LOC642678, RPS15A, CKS2, LIMS1, OSBPL8, GRB2, LOC441763, SPATA13, TPM4, MCTP1, and SUMO3 in a biological sample from the subject. The level of TCL1A, HINT3, CDK5RAP3, FLJ35801, VPREB3, SULT1A1 (transcript variant 5), SULT1A1 (transcript variant 3), FCRLA, LOC100130562, SULT1A2, SLC4A1, LOC90925, MYOM2, CD19, LOC100132727, LOC100008588, CDCA7, TATDN3, LOC648729, HIST1H4H, MCM4, LOC642678, RPS15A, CKS2, LIMS1, OSBPL8, GRB2, LOC441763, SPATA13, TPM4, MCTP1, and SUMO3 to a respective control level of TCL1A, HINT3, CDK5RAP3, FLJ35801, VPREB3, SULT1A1 (transcript variant 5), SULT1A1 (transcript variant 3), FCRLA, LOC100130562, SULT1A2, SLC4A1, LOC90925, MYOM2, CD19, LOC100132727, LOC100008588, CDCA7, TATDN3, LOC648729, HIST1H4H, MCM4, LOC642678, RPS15A, CKS2, LIMS1, OSBPL8, GRB2, LOC441763, SPATA13, TPM4, MCTP1, and SUMO3. The detection of a decrease in the level of TCL1A, HINT3, CDK5RAP3, FLJ35801, VPREB3, SULT1A1 (transcript variant 5), SULT1A1 (transcript variant 3), FCRLA, LOC100130562, SULT1A2, SLC4A1, LOC90925, MYOM2, CD19, and LOC100132727, and an increase in the level of LOC100008588, CDCA7, TATDN3, LOC648729, HIST1H4H, MCM4, LOC642678, RPS15A, CKS2, LIMS1, OSBPL8, GRB2, LOC441763, SPATA13, TPM4, MCTP1, and SUMO3, as compared to the respective control indicates that the subject will develop damage to a reproductive organ after chlamydial infection.

In additional embodiments, the method includes performing one or more assays that detect a level of MYOM2, SLC4A1, LOC402251, LOC286444, FBXO7, TCL1A, LOC100130562, C5ORF28, LOC642989, CD79B, LOC643873, LOC100129742, VPREB3, LOC100133372, RPL13, SULT1A1 (transcript variant 5), CD19, CD79B, LOC100133583, CCR6, LOC642934, LOC100132727, LOC90925, PPA2, LOC100130053, SULT1A4, FCRLA, CDC42, CERK, SDHALP1, LOC100129237, HINT3, SULT1A1 (transcript variant 3), SULT1A2, CMPK1, MEF2D, C10ORF104, JAK1, LOC644739, HS.552082, KCNH6, RPL37A, CDK5RAP3, FLJ3580, FBLN1, CKS2, C10ORF105, CDCA7, HS.489254, MAX, GINS2, MCM4, LOC648729, TATDN3, MYD88, LEPROT, LOC645159, MSRA, TPM4, NAT8B, RTP4, GRB2, SUMO3, RPS15A, MCTP1, LOC642678, PROS1, NFKBIZ, PARP12, OSBPL8, SPATA13, LIMS1, HEBP1, HIST1H4H, LOC441763, LY6E, and LOC100008588 in a biological sample from the subject. The level of MYOM2, SLC4A1, LOC402251, LOC286444, FBXO7, TCL1A, LOC100130562, C5ORF28, LOC642989, CD79B, LOC643873, LOC100129742, VPREB3, LOC100133372, RPL13, SULT1A1 (transcript variant 5), CD19, CD79B, LOC100133583, CCR6, LOC642934, LOC100132727, LOC90925, PPA2, LOC100130053, SULT1A4, FCRLA, CDC42, CERK, SDHALP1, LOC100129237, HINT3, SULT1A1 (transcript variant 3), SULT1A2, CMPK1, MEF2D, C10ORF104, JAK1, LOC644739, HS.552082, KCNH6, RPL37A, CDK5RAP3, FLJ35801, CKS2, C10ORF105, CDCA7, HS.489254, MAX, GINS2, MCM4, LOC648729, TATDN3, MYD88, LEPROT, LOC645159, MSRA, TPM4, NAT8B, RTP4, GRB2, SUMO3, RPS15A, MCTP1, LOC642678, PROS1, NFKBIZ, PARP12, OSBPL8, SPATA13, LIMS1, HEBP1, HIST1H4H, LOC441763, LY6E, and LOC100008588 is compared to a respective control level of MYOM2, SLC4A1, LOC402251, LOC286444, FBXO7, TCL1A, LOC100130562, C5ORF28, LOC642989, CD79B, LOC643873, LOC100129742, VPREB3, LOC100133372, RPL13, SULT1A1 (transcript variant 5), CD19, CD79B, LOC100133583, CCR6, LOC642934, LOC100132727, LOC90925, PPA2, LOC100130053, SULT1A4, FCRLA, CDC42, CERK, SDHALP1, LOC100129237, HINT3, SULT1A1 (transcript variant 3), SULT1A2, CMPK1, MEF2D, C10ORF104, JAK1, LOC644739, HS.552082, KCNH6, RPL37A, CDK5RAP3, FLJ35801, CKS2, C10ORF105, CDCA7, HS.489254, MAX, GINS2, MCM4, LOC648729, TATDN3, MYD88, LEPROT, LOC645159, MSRA, TPM4, NAT8B, RTP4, GRB2, SUMO3, RPS15A, MCTP1, LOC642678, PROS1, NFKBIZ, PARP12, OSBPL8, SPATA13, LIMS1, HEBP1, HIST1H4H, LOC441763, LY6E, and LOC100008588. The detection of a decrease in the level of MYOM2, SLC4A1, LOC402251, LOC286444, FBXO7, TCL1A, LOC100130562, C5ORF28, LOC642989, CD79B, LOC643873, LOC100129742, VPREB3, LOC100133372, RPL13, SULT1A1 (transcript variant 5), CD19, CD79B, LOC100133583, CCR6, LOC642934, LOC100132727, LOC90925, PPA2, LOC100130053, SULT1A4, FCRLA, CDC42, CERK, SDHALP1, LOC100129237, HINT3, SULT1A1 (transcript variant 3), SULT1A2, CMPK1, MEF2D, C10ORF104, JAK1, LOC644739, HS.552082, KCNH6, RPL37A, CDK5RAP3, and FLJ35801, and an increase in FBLN1, CKS2, C10ORF105, CDCA7, HS.489254, MAX, GINS2, MCM4, LOC648729, TATDN3, MYD88, LEPROT, LOC645159, MSRA, TPM4, NAT8B, RTP4, GRB2, SUMO3, RPS15A, MCTP1, LOC642678, PROS1, NFKBIZ, PARP12, OSBPL8, SPATA13, LIMS1, HEBP1, HIST1H4H, LOC441763, LY6E, and LOC100008588, as compared to the respective control indicates that that the subject will develop damage to a reproductive organ from a *chlamydia* infection. In specific non-limiting examples, the damage includes endometritis.

In further embodiments, a method is provided for determining if a pharmaceutical agent is effective for treatment or prevention of chlamydial pelvic inflammatory disease in a female subject. The method includes performing one or more assays that detect a level of TCL1A, HINT3, CDK5RAP3, FLJ35801, VPREB3, SULT1A1 (transcript variant 5), SULT1A1 (transcript variant 3), FCRLA, LOC100130562, SULT1A2, SLC4A1, LOC90925, MYOM2, CD19, LOC100132727, LOC100008588, CDCA7, TATDN3, LOC648729, HIST1H4H, MCM4, LOC642678, RPS15A, CKS2, LIMS1, OSBPL8, GRB2, LOC441763, SPATA13, TPM4, MCTP1, and SUMO3 in a biological sample from the subject; and comparing the level of TCL1A, HINT3, CDK5RAP3, FLJ35801, VPREB3, SULT1A1 (transcript variant 5), SULT1A1 (transcript variant 3), FCRLA, LOC100130562, SULT1A2, SLC4A1, LOC90925, MYOM2, CD19, LOC100132727, LOC100008588, CDCA7, TATDN3, LOC648729, HIST1H4H, MCM4, LOC642678, RPS15A, CKS2, LIMS1, OSBPL8, GRB2, LOC441763, SPATA13, TPM4, MCTP1, and SUMO3 to a respective control level of these markers. The detection of a decrease in the level of TCL1A, HINT3, CDK5RAP3, FLJ35801, VPREB3, SULT1A1 (transcript variant 5), SULT1A1 (transcript variant 3), FCRLA, LOC100130562, SULT1A2, SLC4A1, LOC90925, MYOM2, CD19, and LOC100132727, and an increase in the level of LOC100008588, CDCA7, TATDN3, LOC648729, HIST1H4H, MCM4, LOC642678, RPS15A, CKS2, LIMS1, OSBPL8, GRB2, LOC441763, SPATA13, TPM4, MCTP1, and SUMO3, as compared to the respective control level of TCL1A, HINT3, CDK5RAP3, FLJ35801, VPREB3, SULT1A1 (transcript variant 5), SULT1A1 (transcript variant 3), FCRLA, LOC100130562, SULT1A2, SLC4A1, LOC90925, MYOM2, CD19, LOC100132727, LOC100008588, CDCA7, TATDN3, LOC648729, HIST1H4H, MCM4, LOC642678, RPS15A, CKS2, LIMS1, OSBPL8, GRB2, LOC441763, SPATA13, TPM4, MCTP1, and SUMO3, indicates that the pharmacologic agent is effective for treating the chlamydial pelvic inflammatory disease.

In additional embodiments, the method includes performing one or more assays that detect a level of MYOM2, SLC4A1, LOC402251, LOC286444, FBXO7, TCL1A, LOC100130562, C5ORF28, LOC642989, CD79B, LOC643873, LOC100129742, VPREB3, LOC100133372, RPL13, SULT1A1 (transcript variant 5), CD19, CD79B, LOC100133583, CCR6, LOC642934, LOC100132727, LOC90925, PPA2, LOC100130053, SULT1A4, FCRLA, CDC42, CERK, SDHALP1, LOC100129237, HINT3, SULT1A1 (transcript variant 3), SULT1A2, CMPK1, MEF2D, C10ORF104, JAK1, LOC644739, HS.552082, KCNH6, RPL37A, CDK5RAP3, FLJ3580, FBLN1, CKS2, C10ORF105, CDCA7, HS.489254, MAX, GINS2, MCM4, LOC648729, TATDN3, MYD88, LEPROT, LOC645159, MSRA, TPM4, NAT8B, RTP4, GRB2, SUMO3, RPS15A, MCTP1, LOC642678, PROS1, NFKBIZ, PARP12, OSBPL8, SPATA13, LIMS1, HEBP1, HIST1H4H, LOC441763, LY6E, and LOC100008588 in a biological sample from the subject. The level of MYOM2, SLC4A1, LOC402251, LOC286444, FBXO7, TCL1A, LOC100130562, C5ORF28, LOC642989, CD79B, LOC643873, LOC100129742, VPREB3, LOC100133372, RPL13, SULT1A1 (transcript variant 5), CD19, CD79B, LOC100133583, CCR6, LOC642934, LOC100132727, LOC90925, PPA2, LOC100130053, SULT1A4, FCRLA, CDC42, CERK, SDHALP1, LOC100129237, HINT3, SULT1A1 (transcript variant 5), SULT1A2, CMPK1, MEF2D, C10ORF104, JAK1, LOC644739, HS.552082, KCNH6, RPL37A, CDK5RAP3, FLJ35801, CKS2, C10ORF105, CDCA7, HS.489254, MAX, GINS2, MCM4, LOC648729, TATDN3, MYD88, LEPROT, LOC645159, MSRA, TPM4, NAT8B, RTP4, GRB2, SUMO3, RPS15A, MCTP1, LOC642678, PROS1, NFKBIZ, PARP12, OSBPL8, SPATA13, LIMS1, HEBP1, HIST1H4H, LOC441763, LY6E, and LOC100008588 is compared to a respective control level of MYOM2, SLC4A1, LOC402251, LOC286444, FBXO7, TCL1A, LOC100130562, C5ORF28, LOC642989, CD79B, LOC643873, LOC100129742, VPREB3, LOC100133372, RPL13, SULT1A1 (transcript variant 5), CD19, CD79B, LOC100133583, CCR6, LOC642934, LOC100132727, LOC90925, PPA2, LOC100130053, SULT1A4, FCRLA, CDC42, CERK, SDHALP1, LOC100129237, HINT3, SULT1A1 (transcript variant 3), SULT1A2, CMPK1, MEF2D, C10ORF104, JAK1, LOC644739, HS.552082, KCNH6, RPL37A, CDK5RAP3, FLJ35801, CKS2, C10ORF105, CDCA7, HS.489254, MAX, GINS2, MCM4, LOC648729, TATDN3, MYD88, LEPROT, LOC645159, MSRA, TPM4, NAT8B, RTP4, GRB2, SUMO3, RPS15A, MCTP1, LOC642678, PROS1, NFKBIZ, PARP12, OSBPL8, SPATA13, LIMS1, HEBP1, HIST1H4H, LOC441763, LY6E, and LOC100008588. The detection of a decrease in the level of MYOM2, SLC4A1, LOC402251, LOC286444, FBXO7, TCL1A, LOC100130562, C5ORF28, LOC642989, CD79B, LOC643873, LOC100129742, VPREB3, LOC100133372, RPL13, SULT1A1 (transcript variant 5), CD19, CD79B, LOC100133583, CCR6, LOC642934, LOC100132727, LOC90925, PPA2, LOC100130053, SULT1A4, FCRLA, CDC42, CERK, SDHALP1, LOC100129237, HINT3, SULT1A1 (transcript variant 3), SULT1A2, CMPK1, MEF2D, C10ORF104, JAK1, LOC644739, HS.552082, KCNH6, RPL37A, CDK5RAP3, and FLJ35801, and an increase in the level of FBLN1, CKS2, C10ORF105, CDCA7, HS.489254, MAX, GINS2, MCM4, LOC648729, TATDN3, MYD88, LEPROT, LOC645159, MSRA, TPM4, NAT8B, RTP4, GRB2, SUMO3, RPS15A, MCTP1, LOC642678, PROS1, NFKBIZ, PARP12, OSBPL8, SPATA13, LIMS1, HEBP1, HIST1H4H, LOC441763, LY6E, and LOC100008588, as compared to the respective control level of MYOM2, SLC4A1, LOC402251, LOC286444, FBXO7, TCL1A, LOC100130562, C5ORF28, LOC642989, CD79B, LOC643873, LOC100129742, VPREB3, LOC100133372, RPL13, SULT1A1 (transcript variant 5), CD19, CD79B, LOC100133583, CCR6, LOC642934, LOC100132727, LOC90925, PPA2, LOC100130053, SULT1A4, FCRLA, CDC42, CERK, SDHALP1, LOC100129237, HINT3, SULT1A1 (transcript variant 3), SULT1A2, CMPK1, MEF2D, C10ORF104, JAK1, LOC644739, HS.552082, KCNH6, RPL37A, CDK5RAP3, FLJ35801, CKS2, C10ORF105, CDCA7, HS.489254, MAX, GINS2, MCM4, LOC648729, TATDN3, MYD88, LEPROT, LOC645159, MSRA, TPM4, NAT8B, RTP4, GRB2, SUMO3, RPS15A, MCTP1, LOC642678, PROS1, NFKBIZ, PARP12, OSBPL8, SPATA13, LIMS1, HEBP1, HIST1H4H, LOC441763, LY6E, and LOC100008588 indicates that the pharmacologic agent is effective for treating the chlamydial pelvic inflammatory disease.

In specific, non-limiting examples the subject is asymptomatic. In other specific non-limiting examples, the method predicts endometritis and/or elevated pathogen burden.

The foregoing and other objects, features, and advantages of the invention will become more apparent from the following detailed description, which proceeds with reference to the accompanying figures.

DETAILED DESCRIPTION

Figure 1:
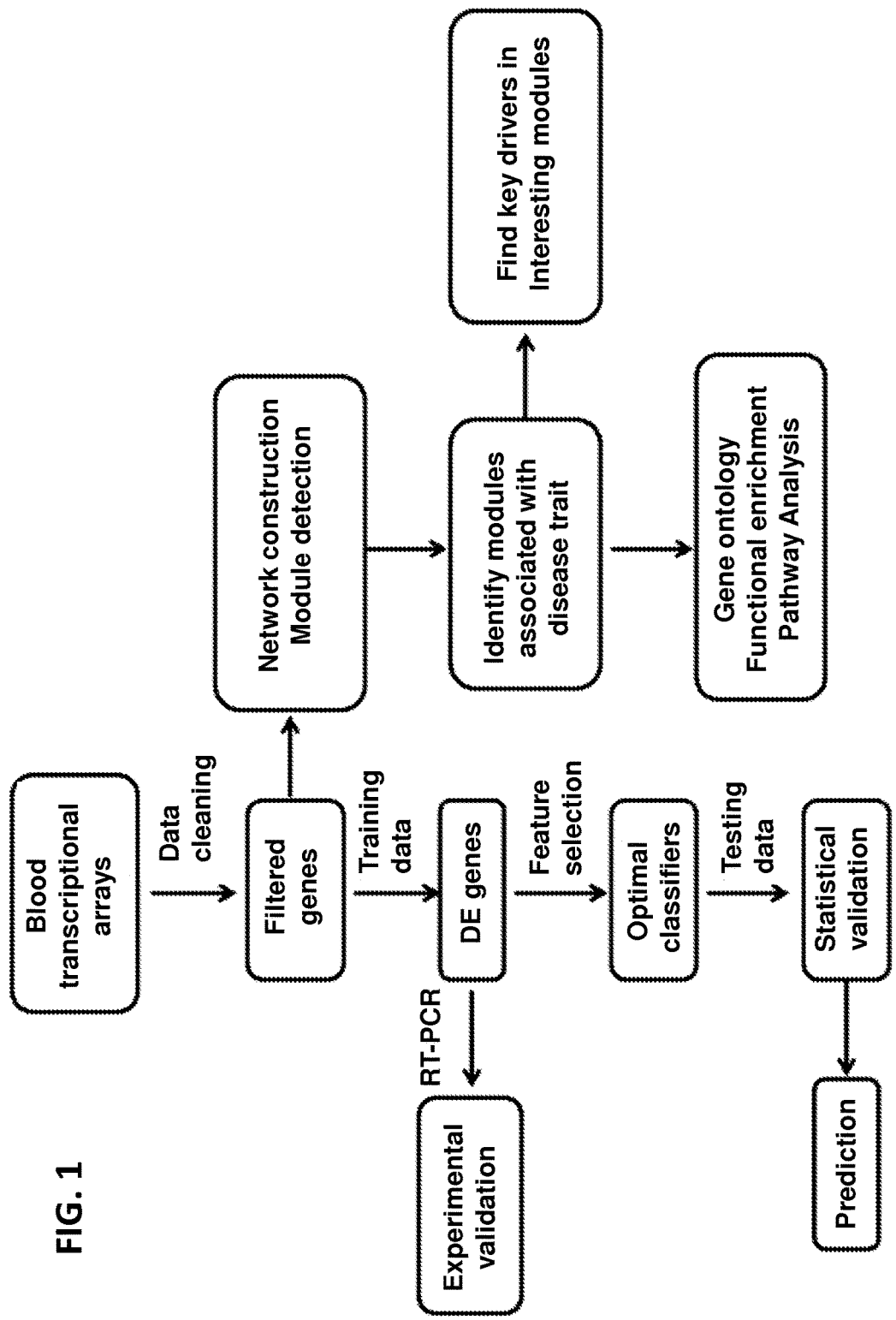
FIG. 1. Outline of strategy used to identify the chlamydial PID transcriptional signature.

Methods are provided herein for determining the likelihood that a subject, such as an asymptomatic subject, has chlamydial pelvic inflammatory disease. In some embodiments, the method determines the likelihood that a pharmaceutical agent is effective for treating a subject that has chlamydial pelvic inflammatory disease. In other specific non-limiting examples, the method predicts endometritis and elevated pathogen burden. In further embodiments, the method determines the likelihood that the subject will develop damage to a reproductive organ after a *chlamydia* infection.

Methods are disclosed herein for detecting or determining the likelihood that a subject will develop damage to a reproductive organ from a *chlamydia* infection. These methods include performing one or more assays that detect a level of the markers shown in Table A (TCL1A, HINT3, CDK5RAP3, FLJ35801, VPREB3, SULT1A1 (transcript variant 5), SULT1A1 (transcript variant 3), FCRLA, LOC100130562, SULT1A2, SLC4A1, LOC90925, MYOM2, CD19, LOC100132727) and Table B (LOC100008588, CDCA7, TATDN3, LOC648729, HIST1H4H, MCM4, LOC642678, RPS15A, CKS2, LIMS1, OSBPL8, GRB2, LOC441763, SPATA13, TPM4, MCTP1, and SUMO3) in a biological sample from the subject, and comparing the level of the markers shown in Table A and B to a respective control level of these markers. Detection of a decrease in the level of the markers shown in Table A, and an increase in the markers shown in Table B, as compared to the respective control indicates the likelihood that the subject is at risk of damage to a reproductive organ.

In additional embodiments, the method can include performing one or more assays that detect a level of the markers shown in Table C (MYOM2, SLC4A1, LOC402251, LOC286444, FBXO7, TCL1A, LOC100130562, C5ORF28, LOC642989, CD79B, LOC643873, LOC100129742, VPREB3, LOC100133372, RPL13, SULT1A1, CD19, CD79B, LOC100133583, CCR6, LOC642934, LOC100132727, LOC90925, PPA2, LOC100130053, SULT1A4, FCRLA, CDC42, CERK, SDHALP1, LOC100129237, HINT3, SULT1A1, SULT1A2, CMPK1, MEF2D, C10ORF104, JAK1, LOC644739, HS.552082, KCNH6, RPL37A, CDK5RAP3, FLJ35801) and Table D (FBLN1, CKS2, C10ORF105, CDCA7, HS.489254, MAX, GINS2, MCM4, LOC648729, TATDN3, MYD88, LEPROT, LOC645159, MSRA, TPM4, NAT8B, RTP4, GRB2, SUMO3, RPS15A, MCTP1, LOC642678, PROS1, NFKBIZ, PARP12, OSBPL8, SPATA13, LIMS1, HEBP1, HIST1H4H, LOC441763, LY6E, LOC100008588) in a biological sample from the subject, and comparing the level of the markers shown in Table C and D to a respective control level of these markers. Detection of a decrease in the level of the markers shown in Table C, and an increase in the markers shown in Table D, as compared to the respective control indicates the likelihood that the subject will develop damage to a reproductive organ after a *chlamydia* infection.

Methods also are disclosed herein for determining if a pharmaceutical agent is effective for treatment or prevention of chlamydial pelvic inflammatory disease in a subject. The method includes performing one or more assays that detect a level of the markers shown in Table A (TCL1A, HINT3, CDK5RAP3, FLJ35801, VPREB3, SULT1A1 (transcript variant 5), SULT1A1 (transcript variant 3), FCRLA, LOC100130562, SULT1A2, SLC4A1, LOC90925, MYOM2, CD19, LOC100132727) and Table B (LOC100008588, CDCA7, TATDN3, LOC648729, HIST1H4H, MCM4, LOC642678, RPS15A, CKS2, LIMS1, OSBPL8, GRB2, LOC441763, SPATA13, TPM4, MCTP1, and SUMO3) in a biological sample from the subject, and comparing the level of the markers shown in Table A and B to a respective control level of these markers. An increase in the level of the markers shown in Table A, and/or a decrease in the markers shown in Table B, indicates that the pharmacologic agent is effective for treating the chlamydial pelvic inflammatory disease. In yet other embodiments, the method includes performing one or more assays that detect a level of the markers shown in Table C (MYOM2, SLC4A1, LOC402251, LOC286444, FBXO7, TCL1A, LOC100130562, C5ORF28, LOC642989, CD79B, LOC643873, LOC100129742, VPREB3, LOC100133372, RPL13, SULT1A1 (transcript variant 5), CD19, CD79B, LOC100133583, CCR6, LOC642934, LOC100132727, LOC90925, PPA2, LOC100130053, SULT1A4, FCRLA, CDC42, CERK, SDHALP1, LOC100129237, HINT3, SULT1A1 (transcript variant 3), SULT1A2, CMPK1, MEF2D, C10ORF104, JAK1, LOC644739, HS.552082, KCNH6, RPL37A, CDK5RAP3, FLJ35801) and Table D (FBLN1, CKS2, C10ORF105, CDCA7, HS.489254, MAX, GINS2, MCM4, LOC648729, TATDN3, MYD88, LEPROT, LOC645159, MSRA, TPM4, NAT8B, RTP4, GRB2, SUMO3, RPS15A, MCTP1, LOC642678, PROS1, NFKBIZ, PARP12, OSBPL8, SPATA13, LIMS1, HEBP1, HIST1H4H, LOC441763, LY6E, LOC100008588) in a biological sample from the subject, and comparing the level of the markers shown in Table C and D to a respective control level of these markers. An increase in the level of the markers shown in Table C, and/or a decrease in the markers shown in Table D, indicates that the pharmacologic agent is effective for treating the chlamydial pelvic inflammatory disease.

Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a nucleic acid molecule" includes single or plural nucleic acid molecules and is considered equivalent to the phrase "comprising at least one nucleic acid molecule." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs. All GENBANK® Accession Nos. listed herein are incorporated by reference in their entirety. Although methods and materials similar or equivalent to those described herein can be used in the practice or testing of the present disclosure, suitable methods and materials are described below. The materials, methods, and examples are illustrative only and not intended to be limiting.

Alter: A change in an effective amount of a substance of interest, such as a polynucleotide or polypeptide. The amount of the substance can changed by a difference in the amount of the substance produced, by a difference in the amount of the substance that has a desired function, or by a difference in the activation of the substance. The change can be an increase or a decrease. The alteration can be in vivo or in vitro.

In several embodiments, altering an amount of a polypeptide or polynucleotide is at least about a 50%, 60%, 70%, 80%, 90%, 95%, 96%, 97%, 98%, 99%, or 100% increase or decrease in the effective amount (level) of a substance. In specific example, an increase of a polypeptide or polynucleotide is at least about a 50%, 60%, 70%, 80%, 90%, 95%, 96%, 97%, 98%, 99%, or 100% increase in a polypeptide or polynucleotide as compared to a control, a statistical normal, or a standard value chosen for specific study. In another specific example, a decrease of a polypeptide or polynucleotide, such as following the initiation of a therapeutic protocol, is at least about a 50%, 60%, 70%, 80%, 90%, 95%, 96%, 97%, 98%, 99%, or 100% decrease in a polypeptide or polynucleotide as compared to a control, a statistical normal, or a standard value chosen for specific study.

Antibody: A polypeptide including at least a light chain or heavy chain immunoglobulin variable region which specifically recognizes and binds an epitope of an antigen or an antigen-binding fragment thereof. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. Antibodies of the present disclosure include those that are specific for the molecules listed.

The term antibody includes intact immunoglobulins, as well the variants and portions thereof, such as Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W.H. Freeman & Co., New York, 1997.

Typically, a naturally occurring immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA, and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs."

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "polyclonal antibody" is an antibody that is derived from different B-cell lines. Polyclonal antibodies are a mixture of immunoglobulin molecules secreted against a specific antigen, each recognizing a different epitope. These antibodies are produced by methods known to those of skill in the art, for instance, by injection of an antigen into a suitable mammal (such as a mouse, rabbit or goat) that induces the B-lymphocytes to produce IgG immunoglobulins specific for the antigen, which are then purified from the mammal's serum.

A "chimeric antibody" has framework residues from one species, such as human, and CDRs (which generally confer antigen binding) from another species, such as a murine antibody that specifically binds an antigen of interest.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one example, all the CDRs are from the donor immunoglobulin in a humanized immunoglobulin. Constant regions need not be present, but if they are, they are substantially identical to human immunoglobulin constant regions, e.g., at least about 85-90%, such as about 95% or more identical. Hence, all parts of a humanized immunoglobulin, except possibly the CDRs, are substantially identical to corresponding parts of natural human immunoglobulin sequences. Humanized immunoglobulins can be constructed by means of genetic engineering (see for example, U.S. Pat. No. 5,585,089).

Array: An arrangement of molecules, such as biological macromolecules (such as peptides or nucleic acid molecules) or biological samples (such as tissue sections), in addressable locations on or in a substrate. A "microarray" is an array that is miniaturized so as to require or be aided by microscopic examination for evaluation or analysis. Arrays are sometimes called chips or biochips.

The array of molecules ("features") makes it possible to carry out a very large number of analyses on a sample at one time. In certain example arrays, one or more molecules (such as an oligonucleotide probe) will occur on the array a plurality of times (such as twice), for instance to provide internal controls. The number of addressable locations on the array can vary, for example from at least one, to at least 2, to at least 5, to at least 10, at least 20, at least 30, at least 50, at least 75, at least 100, at least 150, at least 200, at least 300, at least 500, least 550, at least 600, at least 800, at least 1000, at least 10,000, or more. In particular examples, an array includes nucleic acid molecules, such as oligonucleotide sequences that are at least 15 nucleotides in length, such as about 15-40 nucleotides in length. In particular examples, an array includes oligonucleotide probes or primers which can be used to detect chlamydial pelvic inflammatory disease.

Within an array, each arrayed sample is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Protein-based arrays include probe molecules that are or include proteins, or where the target molecules are or include proteins, and arrays including antibodies to which proteins are bound, or vice versa. In some examples, an array contains antibodies to chlamydial pelvic inflammatory disease-associated proteins.

In some examples, the array includes positive controls, negative controls, or both, for example molecules specific for detecting β-actin, 18S RNA, beta-microglobulin, glyceraldehyde-3-phosphate-dehydrogenase (GAPDH), and other housekeeping genes. In one example, the array includes 1 to 20 controls, such as 1 to 10 or 1 to 5 controls.

*Chlamydia* infection: A common sexually transmitted infection in humans caused by the bacterium *Chlamydia trachomatis*. The term *chlamydia* infection can also refer to infection caused by any species belonging to the bacterial family Chlamydiaceae. *Chlamydia* is known as the "Silent Epidemic" because in women, it may not cause any symptoms in 70-80% of cases. Of those who have an asymptomatic infection that is not detected, approximately half will develop pelvic inflammatory disease (PID). *C. trachomatis* infection can be effectively cured with antibiotics once it is detected. Current CDC guidelines recommend azithromycin or doxycycline, but erythromycin, levofloxacin or ofloxacin can be used as alternative regimens. Agents recommended for pregnant women include azithromycin or amoxicillin. The treatment guidelines can be found at the CDC website (cdc.gov/std/treatment/2010/chlamydial-infections.htm).

Consists essentially of: In the context of the present disclosure, "consists essentially of" indicates that the expression of additional markers associated with a disorder can be evaluated, but not more than ten additional associated markers. In some examples, "consists essentially of" indicates that no more than 5 other molecules are evaluated, such as no more than 4, 3, 2, or 1 other molecules. In some examples, the expression of one or more controls is evaluated, such as a housekeeping protein or rRNA (such as 18S RNA, beta-microglobulin, GAPDH, and/or β-actin) in addition to the genes associated with the disorder. In this context "consists of" indicates that only the expression of the stated molecules is evaluated; the expression of additional molecules is not evaluated.

Control: A "control" refers to a sample or standard used for comparison with an experimental sample. In some embodiments, the control is a sample obtained from a healthy patient or a non-diseased tissue sample (not reproductive tissue) obtained from a patient diagnosed with the disorder of interest, such as chlamydial pelvic inflammatory disease. In some embodiments, the control is a historical control or standard reference value or range of values (such as a previously tested control sample, such as a group of patients that do not have a sexually transmitted infection, or group of samples that represent baseline or normal values, such as the level of specific genes in non-diseased tissue).

Detecting expression of a gene product: Determining the presence of and/or the level of expression of a nucleic acid molecule (such as an mRNA molecule) or a protein encoded by a gene in either a qualitative or quantitative manner. Exemplary methods include microarray analysis, RT-PCR, Northern blot, Western blot, and mass spectrometry of specimens from a subject, for example measuring levels of a gene product present in blood, serum, or another biological sample as a measure of expression.

Diagnosis: The process of identifying a disease by its signs, symptoms and results of various tests. The conclusion reached through that process is also called "a diagnosis."

Forms of testing commonly performed include blood tests, medical imaging, urinalysis, and biopsy.

Differential or alteration in expression: A difference or change, such as an increase or decrease, in the conversion of the information encoded in a gene into messenger RNA, the conversion of mRNA to a protein, or both. In some examples, the difference is relative to a control or reference value or range of values, such as an amount of gene expression that is expected in a subject who does not have chlamydial PID. Detecting differential expression can include measuring a change in gene expression or a change in protein levels.

Downregulated or decreased: When used in reference to the expression of a nucleic acid molecule, such as a gene, refers to any process which results in a decrease in production of a gene product. A gene product can be RNA (such as microRNA, mRNA, rRNA, tRNA, and structural RNA) or protein. Therefore, gene downregulation or deactivation includes processes that decrease transcription of a gene or translation of mRNA.

Examples of processes that decrease transcription include those that facilitate degradation of a transcription initiation complex, those that decrease transcription initiation rate, those that decrease transcription elongation rate, those that decrease processivity of transcription and those that increase transcriptional repression. Gene downregulation can include reduction of expression above an existing level. Examples of processes that decrease translation include those that decrease translational initiation, those that decrease translational elongation and those that decrease mRNA stability.

Gene downregulation includes any detectable decrease in the production of a gene product. In certain examples, production of a gene product decreases by at least 2-fold, for example at least 3-fold or at least 4-fold, as compared to a control (such an amount of gene expression in a normal cell). In one example, a control is a relative amount of gene expression in a biological sample, such as from a subject that does not have chlamydial PID.

Endometritis: Inflammation of the endometrium. Acute Endometritis is characterized by infection. The clinical presentation is typically high fever and purulent vaginal discharge. Chronic Endometritis is characterized by the presence of plasma cells in the stroma. Lymphocytes, eosinophils, and even lymphoid follicles may be seen, but in the absence of plasma cells, are not enough to warrant a histologic diagnosis. It may be seen in up to 10% of all endometrial biopsies performed for irregular bleeding. The most common organisms are *Chlamydia trachomatis* (chlamydia), *Neisseria gonorrhoeae* (gonorrhea), *Streptococcus agalactiae* (Group B *Streptococcus*), *Mycoplasma hominis*, tuberculosis, and various viruses.

Endometritis is the histological diagnosis of inflammation of the endometrium and can be present in the presence or absence of systemic symptoms. Infection is one cause where immune cells invade the endometrium. In acute endometritis associated with infection there is an abundance of neutrophils and plasma cells, while in chronic endometritis there is a preponderance of plasma cells but neutrophils are not abundant. Diagnosis of endometritis associated with PID is used for research purposes. Simultaneous presence of ≥5 neutrophils per 400× field in the endometrial surface epithelium and with one or more plasma cells per 120× field in endometrial stroma defines acute endometritis. However, this is not used standardly in clinical practice when a pathologist makes a general assessment of the specimen.

Expression: The process by which the coded information of a gene is converted into an operational, non-operational, or structural part of a cell, such as the synthesis of a protein. Gene expression can be influenced by external signals. Different types of cells can respond differently to an identical signal. Expression of a gene also can be regulated anywhere in the pathway from DNA to RNA to protein. Regulation can include controls on transcription, translation, RNA transport and processing, degradation of intermediary molecules such as mRNA, or through activation, inactivation, compartmentalization or degradation of specific protein molecules after they are produced. In an example, gene expression can be monitored to determine the diagnosis and/or prognosis of a subject with pelvic inflammatory disease.

The expression of a nucleic acid molecule in a test sample can be altered relative to a control sample, such as a normal sample from a healthy subject. Expression of proteins is the level of protein in a biological sample. Expression includes, but is not limited to, the production of the protein by translation of an mRNA and the half-life of the protein. Protein expression can also be altered in some manner to be different from the expression of the protein in a normal (e.g., non-disease) situation. Alterations in expression, such as differential expression, include but are not limited to: (1) overexpression; (2) underexpression; or (3) suppression of expression.

Controls or standards for comparison to a sample, for the determination of differential expression, include samples believed to be normal (in that they are not altered for the desired characteristic, for example a sample from a subject who does not have pelvic inflammatory disease) as well as laboratory values (e.g., range of values), even though possibly arbitrarily set, keeping in mind that such values can vary from laboratory to laboratory. Laboratory standards and values can be set based on a known or determined population value and can be supplied in the format of a graph or table that permits comparison of measured, experimentally determined values.

Gene expression profile (or signature): Differential or altered gene expression can be detected by changes in the detectable amount of gene expression (such as cDNA or mRNA) or by changes in the detectable amount of proteins expressed by those genes. A distinct or identifiable pattern of gene expression, for instance a pattern of high and low expression of a defined set of genes or gene-indicative nucleic acids such as ESTs. A gene expression profile (also referred to as a signature) can be linked to disease progression (such as chlamydial pelvic inflammatory disease), or to any other distinct or identifiable condition that influences gene expression in a predictable way. Gene expression profiles can include relative as well as absolute expression levels of specific genes, and can be viewed in the context of a test sample compared to a baseline or control sample profile (such as a sample from the same tissue type from a subject who does not have a sexually transmitted infection or chlamydial pelvic inflammatory disease). In one example, a gene expression profile in a subject is read on an array (such as a nucleic acid or protein array). For example, a gene expression profile can be performed using a commercially available array such as Human Genome GENECHIP® arrays from AFFYMETRIX® (Santa Clara, Calif.).

Hybridization: To form base pairs between complementary regions of two strands of DNA, RNA, or between DNA and RNA, thereby forming a duplex molecule, for example. Hybridization conditions resulting in particular degrees of stringency will vary depending upon the nature of the hybridization method and the composition and length of the hybridizing nucleic acid sequences. Generally, the temperature of hybridization and the ionic strength (such as the Na+ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

Very High Stringency (Detects Sequences that Share at Least 90% Identity)
Hybridization: 5×SSC at 65° C. for 16 hours
Wash twice: 2×SSC at room temperature (RT) for 15 minutes each
Wash twice: 0.5×SSC at 65° C. for 20 minutes each
High Stringency (Detects Sequences that Share at Least 80% Identity)
Hybridization: 5×-6×SSC at 65° C.–70° C. for 16-20 hours
Wash twice: 2×SSC at RT for 5-20 minutes each
Wash twice: 1×SSC at 55° C.–70° C. for 30 minutes each
Low Stringency (Detects Sequences that Share at Least 60% Identity)
Hybridization: 6×SSC at RT to 55° C. for 16-20 hours
Wash at least twice: 2×-3×SSC at RT to 55° C. for 20-30 minutes each Isolated: An "isolated" biological component (such as a nucleic acid molecule, protein, or cell) has been substantially separated or purified away from other biological components in the cell of the organism, or the organism itself, in which the component naturally occurs, such as other chromosomal and extra-chromosomal DNA and RNA, proteins and cells. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules and proteins.

Label: An agent capable of detection, for example by ELISA, spectrophotometry, flow cytometry, or microscopy. For example, a label can be attached to a nucleic acid molecule or protein, thereby permitting detection of the nucleic acid molecule or protein. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998). In a particular example, a label is conjugated to a binding agent that specifically binds to a chlamydial pelvic inflammatory disease associated protein, disclosed herein.

Level of Expression: An amount, such as of a protein or an mRNA, that can be measured in a biological sample.

Mammal: This term includes both human and non-human mammals. Examples of mammals include, but are not limited to: humans, pigs, cows, goats, cats, dogs, rabbits, rats, and mice.

Mass Spectrometry: A process used to separate and identify molecules based on their mass. Mass spectrometry ionizes chemical compounds to generate charged molecules or molecule fragments and measures their mass-to-charge ratios. In a typical MS procedure, as sample is ionized. The ions are separated according to their mass-to-charge ratio, and the ions are dynamically detected by some mechanism capable of detecting energetic charged particles. The signal is processed into the spectra of the masses of the particles of that sample. The elements or molecules are identified by correlating known masses by the identified masses. "Time-of-flight mass spectrometry" (TOFMS) is a method of mass spectrometry in which an ion's mass-to-charge ratio is determined via a time measurement. Ions are accelerated by an electric field of known strength. This acceleration results in an ion having the same kinetic energy as any other ion that has the same charge. The velocity of the ion depends on the mass-to-charge ratio. The time that it subsequently takes for the particle to reach a detector at a known distance is measured. This time will depend on the mass-to-charge ratio of the particle (heavier particles reach lower speeds). From this time and the known experimental parameters one can find the mass-to-charge ratio of the ion.

"Liquid chromatography-mass spectrometry" or "LC-MS" is a chemistry technique that combines the physical separation capabilities of liquid chromatography (or HPLC) with the mass analysis capabilities of mass spectrometry. Liquid chromatography mass spectrometry (LC-MS) separates compounds chromatographically before they are introduced to the ion source and mass spectrometer. It differs from gas chromatography (GC-MS) in that the mobile phase is liquid, usually a mixture of water and organic solvents, instead of gas and the ions fragments. Most commonly, an electrospray ionization source is used in LC-MS.

Multiple reaction monitoring (MRM): A mass spectrometry based method in which absolute quantification of a targeted protein(s) can be obtained. In this method external or internal standards are used. Often a known quantity of a synthetic stable isotopically labeled peptide matching each of the targeted peptides that represent unique the protein is added into each sample being quantified. Comparison of the peak of the endogenous peptide to the labeled standard peptide allows absolute quantitation. MRM can be multiplexed easily, allowing multiple phosphorylation sites and/or multiple proteins to be assessed simultaneously.

Nucleic acid array: An arrangement of nucleic acids (such as DNA or RNA) in assigned locations on a matrix, such as that found in cDNA arrays, or oligonucleotide arrays.

Nucleic acid molecules representing genes: Any nucleic acid, for example DNA (intron or exon or both), cDNA, or RNA (such as mRNA), of any length suitable for use as a probe or other indicator molecule, and that is informative about the corresponding gene, such the proteins specified herein.

Pelvic Inflammatory Disease (PID): Inflammation of the uterus, fallopian tubes, and/or ovaries as it progresses to tissue damage, including scar formation with adhesions to nearby tissues and organs. This can lead to infertility. The causes of PID are viral, fungal, and parasitic, although most PID is caused by a bacterial infection. PID can be classified by affected organs, the stage of the infection, and the organism(s) causing it. Although a sexually transmitted infection (STI) is often the cause, many other routes are possible, including lymphatic, postpartum, postabortal (either miscarriage or abortion) or intrauterine device (IUD) related, and hematogenous spread. Treatment depends on the cause and generally involves use of antibiotic therapy, which must be selected based on the type of infection. When symptoms are present, the most common symptoms of PID are lower abdominal pain, mild pelvic pain, increased vaginal discharge, irregular menstrual bleeding, fever (>38° C.), pain with intercourse, painful and frequent urination abdominal tenderness, pelvic organ tenderness, uterine tenderness (along with endometritis) adnexal tenderness (along with salpingitis), cervical motion tenderness, and inflammation. In the case of subclinical PID, women have mild or no pelvic pain, despite evidence of endometritis or salpingitis.

Subclinical PID is asymptomatic. Definitive criteria include: histopathologic evidence of endometritis, thickened filled fallopian tubes, or laparoscopic findings. Although the underlying infection may be cured, effects of the infection can be permanent. This makes early identification important for prevention of damage to the reproductive system.

PID can cause scarring inside the reproductive organs, which can later cause serious complications, including chronic pelvic pain, infertility, ectopic pregnancy, and other pregnancy complications. Occasionally, the infection can spread to in the peritoneum causing inflammation and the formation of scar tissue on the external surface of the liver (Fitz-Hugh-Curtis syndrome).

Peptide/Protein/Polypeptide: All of these terms refer to a polymer of amino acids and/or amino acid analogs that are joined by peptide bonds or peptide bond mimetics, regardless of length or post-translational modification (such as glycosylation, methylation, ubiquitination, phosphorylation, or the like).

Polymerase Chain Reaction (PCR): An in vitro amplification technique that increases the number of copies of a nucleic acid molecule (for example, a nucleic acid molecule in a sample or specimen). The product of a PCR can be characterized by standard techniques known in the art, such as electrophoresis, restriction endonuclease cleavage patterns, oligonucleotide hybridization or ligation, and/or nucleic acid sequencing.

In some examples, PCR utilizes primers, for example, DNA oligonucleotides 10-100 nucleotides in length, such as about 15, 20, 25, 30 or 50 nucleotides or more in length (such as primers that can be annealed to a complementary target DNA strand by nucleic acid hybridization to form a hybrid between the primer and the target DNA strand. Primers can be selected that include at least 15, at least 20, at least 25, at least 30, at least 35, at least 40, at least 45, at least 50 or more consecutive nucleotides of a nucleotide sequence of interest. Methods for preparing and using nucleic acid primers are described, for example, in Sambrook et al. (In *Molecular Cloning: A Laboratory Manual, CSHL*, New York, 1989), Ausubel et al. (ed.) (*In Current Protocols in Molecular Biology*, John Wiley & Sons, New York, 1998), and Innis et al. (PCR Protocols, *A Guide to Methods and Applications*, Academic Press, Inc., San Diego, Calif., 1990).

Primers: Short nucleic acid molecules, for instance DNA oligonucleotides 10-100 nucleotides in length, such as about 15, 20, 25, 30 or 50 nucleotides or more in length, such as this number of contiguous nucleotides of a nucleotide sequence encoding a protein of interest or other nucleic acid molecule. Primers can be annealed to a complementary target DNA strand by nucleic acid hybridization to form a hybrid between the primer and the target DNA strand. Primer pairs can be used for amplification of a nucleic acid sequence, such as by PCR or other nucleic acid amplification methods known in the art.

Methods for preparing and using nucleic acid primers are described, for example, in Sambrook et al. (In *Molecular Cloning: A Laboratory Manual, CSHL*, New York, 1989), Ausubel et al. (*In Current Protocols in Molecular Biology*, John Wiley & Sons, New York, 1998), and Innis et al. (PCR Protocols, *A Guide to Methods and Applications*, Academic Press, Inc., San Diego, Calif., 1990). PCR primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular primer increases with its length.

In one example, a primer includes at least 15 consecutive nucleotides of a nucleotide molecule, such as at least 18 consecutive nucleotides, at least 20, at least 25, at least 30, at least 35, at least 40, at least 45, at least 50 or more consecutive nucleotides of a nucleotide sequence (such as a gene, mRNA or cDNA). Such primers can be used to amplify a nucleotide sequence of interest, such as the markers listed in Tables A, B, and/or C, for example using PCR.

Probe: A short sequence of nucleotides, such as at least 8, at least 10, at least 15, at least 20, at least 21, at least 25, at least 30, at least 35, at least 40, at least 45, at least 50, at least 55, at least 60, at least 65, at least 70, at least 75, at least 80, at least 85, at least 90, at least 95 or even greater than 100 nucleotides in length, used to detect the presence of a complementary sequence by molecular hybridization. In particular examples, oligonucleotide probes include a label that permits detection of oligonucleotide probe:target sequence hybridization complexes. Such an oligonucleotide probe can also be used on a nucleic acid array, for example to detect a nucleic acid molecule in a biological sample contacted to the array. In some examples, a probe is used to detect the presence of a nucleic acid molecule for a markers listed in Tables A, B, and/or C.

Prognosis: A prediction of the future course of a disease, such as chlamydial pelvic inflammatory disease. The prediction can include determining the likelihood of a subject to develop complications of chlamydial pelvic inflammatory disease, damage to their reproductive organs, or to become pregnant, or have an uncomplicated pregnancy, or the particular amount of time (e.g., determine the likelihood that a subject will survive 1, 2, 3 or 5 years), to respond to a particular therapy, or combinations thereof.

Purified: The term "purified" does not require absolute purity; rather, it is intended as a relative term. Thus, for example, a purified protein preparation is one in which the protein referred to is more pure than the protein in its natural environment within a cell. For example, a preparation of a protein is purified such that the protein represents at least 50% of the total protein content of the preparation. Similarly, a purified oligonucleotide preparation is one in which the oligonucleotide is more pure than in an environment including a complex mixture of oligonucleotides.

Sample (or biological sample): A biological specimen containing genomic DNA, RNA (including mRNA), protein, or combinations thereof, obtained from a subject. Examples include, but are not limited to, peripheral blood, serum, plasma, urine, fine needle aspirate, tissue biopsy, surgical specimen, and autopsy material.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, *Adv. Appl.*

Math. 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biotechnology (NCBI, National Library of Medicine, Building 38A, Room 8N805, Bethesda, Md. 20894) and on the Internet, for use in connection with the sequence analysis programs blastp, blastn, blastx, tblastn, and tblastx. Additional information can be found at the NCBI web site.

BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer.

In another example, a target sequence containing a 20-nucleotide region that aligns with 20 consecutive nucleotides from an identified sequence as follows contains a region that shares 75 percent sequence identity to that identified sequence (that is, 15÷20*100=75).

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, *Comput. Appl. Biosci.* 10:67-70). Other programs may use SEG filtering (Wootton and Federhen, *Meth. Enzymol.* 266:554-571, 1996). In addition, a manual alignment can be performed. Proteins with even greater similarity will show increasing percentage identities when assessed by this method, such as at least about 75%, 80%, 85%, 90%, 95%, 98%, or 99% sequence identity to a molecule listed in Tables A, B, or C.

When aligning short peptides (fewer than around 30 amino acids), the alignment is performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least about 60%, 70%, 75%, 80%, 85%, 90%, 95%, 98%, 99% sequence identity to a molecule listed in Tables A, B, or C. When less than the entire sequence is being compared for sequence identity, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site.

One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least about 60%, 70%, 80%, 90%, 95%, 98%, or 99% sequence identity to a molecule listed in Tables A, B, or C determined by this method. An alternative (and not necessarily cumulative) indication that two nucleic acid sequences are substantially identical is that the polypeptide which the first nucleic acid encodes is immunologically cross reactive with the polypeptide encoded by the second nucleic acid.

One of skill in the art will appreciate that the particular sequence identity ranges are provided for guidance only; it is possible that strongly significant homologs could be obtained that fall outside the ranges provided.

Reproductive organs: The organs used for reproduction in a mammal. For a human female, these include the ovaries, fallopian tubes, uterus, and vagina.

Specific Binding Agent: An agent that binds substantially or preferentially only to a defined target such as a protein, enzyme, polysaccharide, oligonucleotide, DNA, RNA, recombinant vector or a small molecule. Thus, a nucleic acid-specific binding agent binds substantially only to the defined nucleic acid, such as RNA, or to a specific region within the nucleic acid. For example, a "specific binding agent" includes an antisense compound (such as an antisense oligonucleotide, siRNA, miRNA, shRNA or ribozyme) that binds substantially to a specified RNA.

A protein-specific binding agent binds substantially only the defined protein, or to a specific region within the protein. For example, a "specific binding agent" includes antibodies and other agents that bind substantially to a specified polypeptide. Antibodies can be monoclonal or polyclonal antibodies that are specific for the polypeptide, as well as immunologically effective portions ("fragments") thereof. The determination that a particular agent binds substantially only to a specific polypeptide may readily be made by using or adapting routine procedures. One suitable in vitro assay makes use of the Western blotting procedure (described in many standard texts, including Harlow and Lane, Using Antibodies: A Laboratory Manual, CSHL, New York, 1999).

Subject: Living multi-cellular vertebrate organism, a category that includes human and non-human mammals.

Therapeutically effective amount: An amount of a pharmaceutical preparation that alone, or together with a pharmaceutically acceptable carrier or one or more additional therapeutic agents, induces the desired response. A therapeutic agent, such as an anticoagulant, or a statin, is administered in therapeutically effective amounts.

Effective amounts a therapeutic agent can be determined in many different ways, such as assaying for a reduction in infection or improvement of physiological condition of a subject having PID. Effective amounts also can be determined through various in vitro, in vivo or in situ assays.

Therapeutic agents can be administered in a single dose, or in several doses, for example daily, during a course of treatment. However, the effective amount of can be dependent on the source applied, the subject being treated, the severity and type of the condition being treated, and the manner of administration.

In one example, it is an amount sufficient to partially or completely alleviate symptoms of inflammation within a subject. Treatment can involve only slowing the progression of inflammation temporarily, but can also include halting or reversing the progression of the inflammation permanently. For example, a pharmaceutical preparation can decrease one or more symptoms or pathology of chlamydial pelvic inflammatory disease, for example decrease a symptom or pathological condition by at least 20%, at least 50%, at least 70%, at least 90%, at least 98%, or even at least 100%, as compared to an amount in the absence of the pharmaceutical preparation.

Translation: The process in which cellular ribosomes create proteins. In translation, messenger RNA (mRNA) produced by transcription is decoded by a ribosome complex to produce a specific polypeptide.

Treating a disease: "Treatment" refers to a therapeutic intervention that ameliorates a sign or symptom of a disease or pathological condition, such a sign, parameter or symptom of pelvic inflammatory disease. Treatment also can induce remission or cure of a condition. In particular examples, treatment includes preventing a disease, for example by inhibiting the full development of a disease, such as preventing development of pelvic inflammatory disease in a subject infected with *Chlamydia*. Prevention of a disease does not require a total absence of disease. For example, a decrease of inflammation at least 50% can be sufficient.

Upregulated or activation: When used in reference to the expression of a nucleic acid molecule, such as a gene, refers to any process which results in an increase in production of a gene product. A gene product can be RNA (such as mRNA, rRNA, tRNA, and structural RNA) or protein. Therefore, gene upregulation or activation includes processes that increase transcription of a gene or translation of mRNA.

Examples of processes that increase transcription include those that facilitate formation of a transcription initiation complex, those that increase transcription initiation rate, those that increase transcription elongation rate, those that increase processivity of transcription and those that relieve transcriptional repression (for example by blocking the binding of a transcriptional repressor). Gene upregulation can include inhibition of repression as well as stimulation of expression above an existing level. Examples of processes that increase translation include those that increase translational initiation, those that increase translational elongation and those that increase mRNA stability.

Gene upregulation includes any detectable increase in the production of a gene product. In certain examples, production of a gene product increases by at least 1.5-fold, such as at least 2-fold, at least 3-fold or at least 4-fold, as compared to a control. In one example, a control is a relative amount of gene expression in a biological sample, such as from a subject that does not have chlamydial PID.

Additional terms commonly used in molecular genetics can be found in Benjamin Lewin, *Genes V*, published by Oxford University Press, 1994 (ISBN 0-19-854287-9); Kendrew et al (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Chlamydial Pelvic Inflammatory Disease

The disclosed methods utilize marker sets to identify subjects. In some embodiments, the methods include measuring the makers listed in Table A (TCL1A, HINT3, CDK5RAP3, FLJ35801, VPREB3, SULT1A1 (transcript variant 5), SULT1A1 (transcript variant 3), FCRLA, LOC100130562, SULT1A2, SLC4A1, LOC90925, MYOM2, CD19, LOC100132727) and Table B (LOC100008588, CDCA7, TATDN3, LOC648729, HIST1H4H, MCM4, LOC642678, RPS15A, CKS2, LIMS1, OSBPL8, GRB2, LOC441763, SPATA13, TPM4, MCTP1, and SUMO3). In other embodiments, the methods include measuring the markers listed in Table C (MYOM2, SLC4A1, LOC402251, LOC286444, FBXO7, TCL1A, LOC100130562, C5ORF28, LOC642989, CD79B, LOC643873, LOC100129742, VPREB3, LOC100133372, RPL13, SULT1A1 (transcript variant 5), CD19, CD79B, LOC100133583, CCR6, LOC642934, LOC100132727, LOC90925, PPA2, LOC100130053, SULT1A4, FCRLA, CDC42, CERK, SDHALP1, LOC100129237, HINT3, SULT1A1 (transcript variant 3), SULT1A2, CMPK1, MEF2D, C10ORF104, JAK1, LOC644739, HS.552082, KCNH6, RPL37A, CDK5RAP3, FLJ35801) and Table D (FBLN1, CKS2, C10ORF105, CDCA7, HS.489254, MAX, GINS2, MCM4, LOC648729, TATDN3, MYD88, LEPROT, LOC645159, MSRA, TPM4, NAT8B, RTP4, GRB2, SUMO3, RPS15A, MCTP1, LOC642678, PROS1, NFKBIZ, PARP12, OSBPL8, SPATA13, LIMS1, HEBP1, HIST1H4H, LOC441763, LY6E, LOC100008588). In some embodiments, the subject is administered a pharmaceutical agent, such as, but not limited to, azithromycin, doxycycline, erythromycin, amoxicillin and/or ofloxacin.

In some embodiments, the control is a sample obtained from a healthy patient or a non-diseased tissue sample (not reproductive tissue) obtained from a patient diagnosed with the disorder of interest, such as chlamydial pelvic inflammatory disease. In some embodiments, the control is a historical control or standard reference value or range of values (such as a previously tested control sample, such as a group of patients that do not have a sexually transmitted infection, or group of samples that represent baseline or normal values, such as the level of specific genes in non-diseased tissue).

Methods are provided herein for evaluating risk, for example for determining the likelihood that a subject, such as an asymptomatic subject, has chlamydial pelvic inflammatory disease. Method are provided for detecting a *chlamydia* infection in a subject.

In additional embodiments, methods are provided to determine the likelihood that a pharmaceutical agent is effective for treating a subject that has chlamydial pelvic inflammatory disease. The subject can be a female subject. In some examples, the subject has a *chlamydia* infection. In other embodiments, the subject does not have a *chlamydia* infection.

The expression of the markers disclosed herein can also be used to identify women at a higher risk of poor outcome and who are more likely to benefit from regular and/or intensive screening. The expression of the markers disclosed herein can also be used to identify women who will benefit from vaccination. For example, the markers listed in Tables A and B, or Tables C and D can be used to identify women at a higher risk of a poor outcome, such as damage to their reproductive organs, and who are more likely to benefit from regular and/or intensive screening and/or who are more likely to benefit from vaccination. In some embodiments, method are provided to determine the likelihood that a woman will develop damage to their reproductive organs, such as scar formation and adhesions, from a *chlamydia* infection. In some specific non-limiting examples, the method predicts endometritis and elevated pathogen burden.

In some examples, a biological sample obtained from the subject, such as, but not limited to, serum, blood, plasma, urine, purified cells (for example, blood cells, such as white blood cells, B cells, T cells, or mononuclear cells), saliva, a biopsy or tissue sample, such as a sample including uterine tissue, ovarian tissue, or fallopian tube tissue obtained from the subject are used to predict the subject's risk of chlamydial pelvic inflammatory disease.

In some embodiments of the methods disclosed herein, the subject can be apparently healthy, such as a subject who does not exhibit symptoms of pelvic inflammatory disease, which can include lower abdominal pain, mild pelvic pain, increased vaginal discharge, irregular menstrual bleeding, fever (>38° C.), pain with intercourse, painful and frequent urination, abdominal tenderness, pelvic organ tenderness, uterine tenderness (along with endometritis) adnexal tenderness (along with salpingitis), cervical motion tenderness, and inflammation. In additional embodiments, the subject has not previously had a sexually transmitted disease. In some examples, an asymptomatic subject is one that if examined by a medical professional, would be characterized as healthy and free of symptoms of pelvic inflammatory disease. The methods disclosed herein can be used to screen subjects for future evaluation or treatment for chlamydial pelvic inflammatory disease. The methods can include treating chlamydial pelvic inflammatory disease following detection using the disclosed methods.

In other embodiments, the subject can have one or more symptoms of chlamydial pelvic inflammatory disease. The methods disclosed herein can be used to confirm a prior clinical suspicion of chlamydial pelvic inflammatory disease.

In some embodiments, the methods determine the likelihood that a subject has chlamydial pelvic inflammatory disease. In specific non-limiting examples, the subject is suspected of having a chlamydial pelvic inflammatory disease, or is suspected of being at risk of developing pelvic inflammatory disease. For example, such a subject can have multiple sexual partners and/or can previously have had one or more sexually transmitted diseases.

The expression of the markers disclosed herein can be used to assess the efficacy of a therapeutic protocol for the treatment of chlamydial pelvic inflammatory disease. In some embodiments, methods are provided for evaluating the efficacy of a treatment protocol that includes any therapy for designed to treat or slow the progression of an infection, including but not limited to treatment with antibiotics such as azithromycin, doxycycline, erythromycin, amoxicillin or ofloxacin, or any other pharmaceutical compound.

In these embodiments, a sample can be taken from a subject prior to initiation of therapy. After therapy is initiated, an additional sample is taken from the subject. A decrease in the amount of the markers indicates that the therapy is efficacious. In addition, the subject can be monitored over time to evaluate the continued effectiveness of the therapeutic protocol. The effect of different dosages can also be evaluated, by comparing the expression of markers in a sample from the subject receiving a first dose to the expression of the same markers in a sample from the subject receiving a second (different) dose. The methods can be repeated 1, 2, 3, 4, 5, 6, 7, 8, 9, 10 or more times to determine the lowest dose of a pharmaceutical agent that is effective for treating the subject, and/or the shortest duration of administration that is effective for treating the subject. The methods can also be used over the course of a therapeutic regimen to monitor the efficacy of a pharmaceutical agent for the treatment of the subject.

In yet other embodiments, the subject has been determined to be at risk for pelvic inflammatory disease based on risk factors, such as, but not limited to, sexual history and clinical history of sexually transmitted diseases. The method can include evaluation of a subject to determine if they are at risk for chlamydial pelvic inflammatory disease using risk factors, such as, but not limited to, prior infections, prior sexually transmitted disease, and multiple partners. The subject can be a sex worker. The method can predict risk for damaging inflammation if the subject is infected again with *Chlamydia* at a future time.

Tables A, B, C and D, disclose markers of use in the disclosed methods. Either mRNA or protein can be evaluated for each marker listed in Tables A, B, C and D. It is appreciated that nucleic and protein sequences can differ slightly amongst different individuals in a population. In some embodiments, detection of these markers listed in Tables A, B, C and/or D includes detecting a protein or mRNA at least 95%, 96%, 97%, 98%, 99% or 100% identical to the listed GENBANK® Accession number. In further embodiments detection of the markers listed in Table A, B, C and/or D, that have at most 10, 9, 8, 7, 6, 5, 4, 3, 2, 1 substitutions in the reference sequence listed in Tables A, B, C and/or D. In some embodiments, the expression of additional markers (protein or nucleic acids) can also be evaluated. Thus, assays that include detection of the markers listed in Tables A, B, C and/or D can include the detection of additional proteins and/or mRNA sequences.

In some embodiments, the methods disclosed herein can include evaluating the level of one, more or all of the following:

TABLE A

Genes (RNA/Protein) down-regulated (Fold change < 1.0) in the minimum chlamydial PID signature.

| Gene Symbol | p value | Adjusted p value | Fold Change | ACCESSION |
|---|---|---|---|---|
| TCL1A | 1.46E−06 | 0.001410265 | 0.533888232 | NM_001098725.1 |
| HINT3 | 2.20E−05 | 0.004615395 | 0.737912062 | NM_138571.4 |

TABLE A-continued

Genes (RNA/Protein) down-regulated (Fold change < 1.0) in the minimum chlamydial PID signature.

| Gene Symbol | p value | Adjusted p value | Fold Change | ACCESSION |
|---|---|---|---|---|
| CDK5RAP3 | 0.002964725 | 0.037586812 | 0.806074888 | NM_176095.1 |
| FLJ35801 | 0.003148175 | 0.0388813 | 0.816076372 | NM_153044.1 |
| VPREB3 | 0.000732768 | 0.019498872 | 0.639320549 | NM_013378.1 |
| SULT1A1 (transcript variant 5) | 0.0005338 | 0.01707774 | 0.740072546 | NM_177536.1 |
| SULT1A1 (transcript variant 3) | 7.22E−06 | 0.002882061 | 0.658823223 | NM_177530.1 |
| FCRLA | 0.003197706 | 0.039179988 | 0.716180272 | NM_032738.3 |
| LOC100130562 | 5.07E−05 | 0.006455432 | 0.586417779 | XM_001720379.1 |
| SULT1A2 | 0.001421189 | 0.027223457 | 0.757270352 | NM_001054.2 |
| SLC4A1 | 0.001693564 | 0.028778708 | 0.493816558 | NM_000342.2 |
| LOC90925 | 0.000604222 | 0.017628007 | 0.681048184 | NM_175870.3 |
| MYOM2 | 0.002988523 | 0.037789604 | 0.430463281 | NM_003970.1 |
| CD19 | 0.000885191 | 0.021542619 | 0.666118078 | NM_001770.4 |
| LOC100132727 | 0.000564588 | 0.017480464 | 0.677567918 | XM_001723325.1 |

TABLE B

Genes (RNA/Protein) up-regulated (Fold change < 1.0) in the minimum chlamydial PID signature.

| Gene Symbol | p value | Adjusted p value | Fold Change | ACCESSION |
|---|---|---|---|---|
| LOC100008588 | 8.13E−05 | 0.008562637 | 2.987179291 | NR_003286.1 |
| CDCA7 | 0.003891851 | 0.043731406 | 1.238947859 | NM_031942.4 |
| TATDN3 | 0.000502907 | 0.016990412 | 1.272091003 | NM_001042552.1 |
| LOC648729 | 0.001561954 | 0.028438133 | 1.262350648 | XR_039144.1 |
| HIST1H4H | 0.000380779 | 0.015897516 | 1.582307528 | NM_003543.3 |
| MCM4 | 0.003273635 | 0.039331849 | 1.261673176 | NM_005914.2 |
| LOC642678 | 0.002592056 | 0.03543651 | 1.451406288 | XM_926130.1 |
| RPS15A | 0.000299433 | 0.014557172 | 1.423910022 | NM_001030009.1 |
| CKS2 | 0.001465648 | 0.027419578 | 1.224171819 | NM_001827.1 |
| LIMS1 | 0.001898989 | 0.030176904 | 1.49195121 | NM_004987.3 |
| OSBPL8 | 0.0005193 | 0.016990412 | 1.479426946 | NM_020841.4 |
| GRB2 | 0.000531921 | 0.01707774 | 1.38354601 | NM_002086.3 |
| LOC441763 | 0.00030681 | 0.01456899 | 1.629602627 | XM_930284.1 |
| SPATA13 | 0.002594227 | 0.03543651 | 1.484737028 | NM_153023.1 |
| TPM4 | 0.000485728 | 0.016990412 | 1.329266853 | NM_003290.1 |
| MCTP1 | 7.90E−06 | 0.002882061 | 1.444265644 | NM_024717.3 |
| SUMO3 | 0.002209861 | 0.031647678 | 1.385855818 | NM_006936.2 |

The GENBANK® entries listed in Tables A and B are incorporated by reference herein in their entirety as available on Mar. 26, 2014.

Thus, a method of detecting or determining the likelihood that a subject has chlamydial pelvic inflammatory disease (PID) is provided. The methods include performing one or more assays that detect a level of the markers shown in Tables A and B in a biological sample from the subject; and comparing the level of the markers shown in Table A and B to a respective control level of these markers. Detection of a decrease in the level of the markers shown in Table A, and an increase in the markers shown in Table B, as compared to the respective control indicates the likelihood that the subject has chlamydial pelvic inflammatory disease (PID).

In other embodiments, the methods disclosed herein can include evaluating the level of one, more or all of the following:

TABLE C

Genes down-regulated (Fold change < 1.0) in the chlamydial PID transcriptional signature (77 classifiers).

| Gene symbol | Fold change | P value | Adjust p value | Accession |
|---|---|---|---|---|
| MYOM2 | 0.430463281 | 0.002988523 | 0.037789604 | NM_003970.1 |
| SLC4A1 | 0.493816558 | 0.001693564 | 0.028778708 | NM_000342.2 |
| LOC402251 | 0.495720192 | 2.05E−08 | 9.92E−05 | XM_377933.3 |
| LOC286444 | 0.509379487 | 0.000329811 | 0.01456899 | XR_038693.1 |

TABLE C-continued

Genes down-regulated (Fold change < 1.0) in the chlamydial PID transcriptional signature (77 classifiers).

| Gene symbol | Fold change | P value | Adjust p value | Accession |
|---|---|---|---|---|
| FBXO7 | 0.515381126 | 0.000552884 | 0.017480464 | NM_001033024.1 |
| TCL1A | 0.533888232 | 1.46E-06 | 0.001410265 | NM_001098725.1 |
| LOC100130562 | 0.586417779 | 5.07E-05 | 0.006455432 | XM_001720379.1 |
| C5ORF28 | 0.589604499 | 0.000133893 | 0.010630191 | NM_022483.3 |
| LOC642989 | 0.603773756 | 0.00082731 | 0.020759904 | XM_926370.1 |
| CD79B | 0.620233558 | 0.001961832 | 0.030452411 | NM_001039933.1 |
| LOC643873 | 0.63447115 | 0.000124519 | 0.010557533 | XR_039149.1 |
| LOC100129742 | 0.634977611 | 0.00204349 | 0.031023898 | XR_037977.1 |
| VPREB3 | 0.639320549 | 0.000732768 | 0.019498872 | NM_013378.1 |
| LOC100133372 | 0.650467727 | 9.29E-06 | 0.002882061 | XR_039042.1 |
| RPL13 | 0.650902492 | 2.58E-05 | 0.004895576 | NM_033251.1 |
| SULT1A1 (transcript variant 3) | 0.658823223 | 7.22E-06 | 0.002882061 | NM_177530.1 |
| CD19 | 0.666118078 | 0.000885191 | 0.021542619 | NM_001770.4 |
| CD79B | 0.669780886 | 0.000509224 | 0.016990412 | NM_000626.1 |
| LOC100133583 | 0.672866944 | 0.004706101 | 0.047681268 | XM_001714074.1 |
| CCR6 | 0.676926533 | 0.000222428 | 0.013040233 | NM_031409.3 |
| LOC642934 | 0.677048774 | 0.001772688 | 0.029316443 | XM_942991.2 |
| LOC100132727 | 0.677567918 | 0.000564588 | 0.017480464 | XM_001723325.1 |
| LOC90925 | 0.681048184 | 0.000604222 | 0.017628007 | NM_175870.3 |
| PPA2 | 0.685847897 | 0.000245803 | 0.013842115 | NM_006903.4 |
| LOC100130053 | 0.701256648 | 0.001309788 | 0.026211988 | XM_001721292.1 |
| SULT1A4 | 0.711744185 | 0.00060335 | 0.017628007 | NM_001017391.1 |
| FCRLA | 0.716180272 | 0.003197706 | 0.039179988 | NM_032738.3 |
| CDC42 | 0.719356177 | 0.001264288 | 0.025512279 | NM_001039802.1 |
| CERK | 0.728713169 | 0.000115086 | 0.010516234 | NM_182661.1 |
| SDHALP1 | 0.733872148 | 0.003420066 | 0.040202382 | NR_003264.1 |
| LOC100129237 | 0.735831959 | 0.000455271 | 0.016990412 | XR_038101.1 |
| HINT3 | 0.737912062 | 2.20E-05 | 0.004615395 | NM_138571.4 |
| SULT1A1 (transcript variant 5) | 0.740072546 | 0.0005338 | 0.01707774 | NM_177536.1 |
| SULT1A2 | 0.757270352 | 0.001421189 | 0.027223457 | NM_001054.2 |
| CMPK1 | 0.758726129 | 0.003644831 | 0.042058009 | NM_016308.1 |
| MEF2D | 0.761929823 | 0.000148444 | 0.010759652 | NM_005920.2 |
| C10ORF104 | 0.763497751 | 0.000328754 | 0.01456899 | NM_173473.2 |
| JAK1 | 0.764033216 | 0.001631035 | 0.028474781 | NM_002227.2 |
| LOC644739 | 0.770681192 | 0.004100027 | 0.045025924 | XM_933679.1 |
| HS.552082 | 0.79036876 | 0.00086625 | 0.021188125 | BU616603 |
| KCNH6 | 0.795979768 | 0.005085935 | 0.049370605 | NM_030779.2 |
| RPL37A | 0.799734547 | 0.002585317 | 0.03543651 | NM_000998.4 |
| CDK5RAP3 | 0.806074888 | 0.002964725 | 0.037586812 | NM_176095.1 |
| FLJ35801 | 0.816076372 | 0.003148175 | 0.0388813 | NM_153044.1 |

TABLE D

Genes up-regulated (Fold change < 1.0) in the chlamydial PID transcriptional signature (77 classifiers).

| Gene symbol | Fold change | pvalue | Adjust pvalue | Accession |
|---|---|---|---|---|
| FBLN1 | 1.222655121 | 0.004055246 | 0.044839168 | NM_001996.2 |
| CKS2 | 1.224171819 | 0.001465648 | 0.027419578 | NM_001827.1 |
| C10ORF105 | 1.236657774 | 0.003236244 | 0.039182829 | XM_001723289.1 |
| CDCA7 | 1.238947859 | 0.003891851 | 0.043731406 | NM_031942.4 |
| HS.489254 | 1.245018325 | 0.000522728 | 0.016990412 | BC031266 |
| MAX | 1.246549223 | 0.00173854 | 0.029134075 | NM_145114.1 |
| GINS2 | 1.257559476 | 0.002208031 | 0.031647678 | NM_016095.1 |
| MCM4 | 1.261673176 | 0.003273635 | 0.039331849 | NM_005914.2 |
| LOC648729 | 1.262350648 | 0.001561954 | 0.028438133 | XR_039144.1 |
| TATDN3 | 1.272091003 | 0.000502907 | 0.016990412 | NM_001042552.1 |
| MYD88 | 1.274019249 | 0.001642239 | 0.028474781 | NM_002468.3 |
| LEPROT | 1.280661328 | 0.003797667 | 0.042595493 | NM_017526.2 |
| LOC645159 | 1.29546137 | 0.001349708 | 0.026464112 | XM_928195.2 |
| MSRA | 1.321064097 | 0.002096713 | 0.031535344 | NM_012331.2 |
| TPM4 | 1.329266853 | 0.000485728 | 0.016990412 | NM_003290.1 |
| NAT8B | 1.331351675 | 0.004805116 | 0.048180489 | NM_016347.2 |
| RTP4 | 1.346510072 | 0.001348327 | 0.026464112 | NM_022147.2 |

TABLE D-continued

Genes up-regulated (Fold change < 1.0) in the chlamydial
PID transcriptional signature (77 classifiers).

| Gene symbol | Fold change | pvalue | Adjust pvalue | Accession |
|---|---|---|---|---|
| GRB2 | 1.38354601 | 0.000531921 | 0.01707774 | NM_002086.3 |
| SUMO3 | 1.385855818 | 0.002209861 | 0.031647678 | NM_006936.2 |
| RPS15A | 1.423910022 | 0.000299433 | 0.014557172 | NM_001030009.1 |
| MCTP1 | 1.444265644 | 7.90E−06 | 0.002882061 | NM_024717.3 |
| LOC642678 | 1.451406288 | 0.002592056 | 0.03543651 | XM_926130.1 |
| PROS1 | 1.456485747 | 0.001561741 | 0.028438133 | NM_000313.1 |
| NFKBIZ | 1.461664034 | 5.64E−05 | 0.007000129 | NM_001005474.1 |
| PARP12 | 1.474199773 | 0.000817632 | 0.020731892 | NM_022750.2 |
| OSBPL8 | 1.479426946 | 0.0005193 | 0.016990412 | NM_020841.4 |
| SPATA13 | 1.484737028 | 0.002594227 | 0.03543651 | NM_153023.1 |
| LIMS1 | 1.49197121 | 0.001898989 | 0.030176904 | NM_004987.3 |
| HEBP1 | 1.510497586 | 0.000418315 | 0.016547248 | NM_015987.3 |
| HIST1H4H | 1.582307528 | 0.000380779 | 0.015897516 | NM_003543.3 |
| LOC441763 | 1.629602627 | 0.00030681 | 0.01456899 | XM_930284.1 |
| LY6E | 1.76850941 | 0.002904697 | 0.037447978 | NM_002346.1 |
| LOC100008588 | 2.987179291 | 8.13E−05 | 0.008562637 | NR_003286.1 |

The GENBANK® entries listed in Tables C and D are incorporated by reference herein in their entirety as available on Mar. 26, 2014.

Thus, a method of detecting or determining the likelihood that a subject has chlamydial pelvic inflammatory disease (PID) is provided. The methods include performing one or more assays that detect a level of the markers shown in Tables C and D in a biological sample from the subject; and comparing the level of the markers shown in Table C and D to a respective control level of these markers. Detection of a decrease in the level of the markers shown in Table C, and an increase in the markers shown in Table D, as compared to the respective control indicates the likelihood that the subject has chlamydial PID.

Methods are also provided for determining if a pharmaceutical agent is effective for treatment or prevention of chlamydial PID in a subject. In specific non-liming examples, the subject can have chlamydial PID. In some embodiments, a method is provided for determining if a pharmaceutical agent is effective for treatment or prevention of pelvic inflammatory disease in a subject. The method includes performing one or more assays that detect a level of the markers shown in Tables A and B in a biological sample from the subject; and comparing the level of the markers shown in Table A and B to a respective control level of these markers. An increase in the level of the markers shown in Table A, and/or a decrease in the markers shown in Table B, indicates that the pharmacologic agent is effective for treating the chlamydial pelvic inflammatory disease.

In other embodiments, a method is provided for determining if a pharmaceutical agent is effective for treatment or prevention of pelvic inflammatory disease in a subject. The method includes performing one or more assays that detect a level of the markers shown in Tables C and D in a biological sample from the subject; and comparing the level of the markers shown in Table C and D to a respective control level of these markers. An increase in the level of the markers shown in Table C, and/or a decrease in the markers shown in Table D, indicates that the pharmacologic agent is effective for treating the chlamydial pelvic inflammatory disease.

The pharmaceutical agent can be any agent of interest. In some embodiments, the pharmaceutical agent is azithromycin, doxycycline, erythromycin, amoxicillin or ofloxacin.

Methods for Detection of mRNA

Gene expression can be evaluated by detecting mRNA encoding the gene of interest. Thus, the disclosed methods can include evaluating mRNA encoding one or more of the markers listed in Tables A, B, or C. Any of the methods disclosed above can utilize the detection of mRNA. In some embodiments, the disclosed methods also include evaluating mRNA encoding one or more of the markers listed in the Tables disclosed herein.

RNA can be isolated from a sample from a subject, such as a biopsy, tissue sample, uterine tissue, ovarian tissue, fallopian tube tissue, blood vessel, peripheral blood mononuclear cells, or isolated cells, such as white blood cells (B, T or mononuclear cells). RNA can also be isolated from a control, such as the same type of biological tissue from a healthy subject, for example a subject known not to have chlamydial pelvic inflammatory disease or a sexually transmitted infection, using methods well known to one skilled in the art, including commercially available kits. General methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, *Biotechniques* 6:56-60 (1988), and De Andres et al., *Biotechniques* 18:42-44 (1995). In one example, RNA isolation can be performed using purification kit, buffer set and protease from commercial manufacturers, such as QIAGEN® (Valencia, Calif.), according to the manufacturer's instructions. For example, total RNA from cells in culture (such as those obtained from a subject) can be isolated using QIAGEN® RNeasy® mini-columns. Other commercially available RNA isolation kits include MASTERPURE® Complete DNA and RNA Purification Kit (EPICENTRE® Madison, Wis.), and Paraffin Block RNA Isolation Kit (Ambion, Inc.). Total RNA from tissue samples can be isolated using RNA Stat-60 (Tel-Test). RNA prepared from a biological sample can be isolated, for example, by cesium chloride density gradient centrifugation.

Methods of gene expression profiling include methods based on hybridization analysis of polynucleotides, methods based on sequencing of polynucleotides, and proteomics-based methods. In some examples, mRNA expression in a sample is quantified using Northern blotting or in situ hybridization (Parker & Barnes, *Methods in Molecular Biology* 106:247-283, 1999); RNAse protection assays (Hod, *Biotechniques* 13:852-4, 1992); and PCR-based methods, such as reverse transcription polymerase chain reaction (RT-PCR) (Weis et al., *Trends in Genetics* 8:263-4, 1992). Alternatively, antibodies can be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS). In one example, RT-PCR can be used to compare mRNA levels in different samples, such as from a subject that is undergoing treatment, to characterize patterns of gene expression, to discriminate between closely related mRNAs, and to analyze RNA structure.

Methods for quantitating mRNA are well known in the art. In some examples, the method utilizes RT-PCR. For example, extracted RNA can be reverse-transcribed using a GENEAMP® RNA PCR kit (Perkin Elmer, Calif., USA), following the manufacturer's instructions.

For example, TAQMAN® RT-PCR can be performed using commercially available equipment. The system can include a thermocycler, laser, charge-coupled device (CCD) camera, and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

To minimize errors and the effect of sample-to-sample variation, RT-PCR can be performed using an internal standard. The ideal internal standard is expressed at a constant level among different tissues, and is unaffected by an experimental treatment. RNAs commonly used to normalize patterns of gene expression are mRNAs for the housekeeping genes GAPDH, β-actin, and 18S ribosomal RNA.

A variation of RT-PCR is real time quantitative RT-PCR, which measures PCR product accumulation through a dual-labeled fluorogenic probe (e.g., TAQMAN® probe). Real time PCR is compatible both with quantitative competitive PCR, where internal competitor for each target sequence is used for normalization, and with quantitative comparative PCR using a normalization gene contained within the sample, or a housekeeping gene for RT-PCR (see Heid et al., *Genome Research* 6:986-994, 1996). Quantitative PCR is also described in U.S. Pat. No. 5,538,848. Related probes and quantitative amplification procedures are described in U.S. Pat. No. 5,716,784 and U.S. Pat. No. 5,723,591. Instruments for carrying out quantitative PCR in microtiter plates are available from PE Applied Biosystems (Foster City, Calif.).

The steps of a representative protocol for quantitating gene expression using fixed, paraffin-embedded tissues as the RNA source, including mRNA isolation, purification, primer extension and amplification are given in various published journal articles (see Godfrey et al., *J. Mol. Diag.* 2:84 91, 2000; Specht et al., *Am. J. Pathol.* 158:419-29, 2001). Briefly, a representative process starts with cutting about 10 μm thick sections of paraffin-embedded tissue samples or adjacent non-diseased tissue. The RNA is then extracted, and protein and DNA are removed. Alternatively, RNA is isolated directly from a tissue sample. After analysis of the RNA concentration, RNA repair and/or amplification steps can be included, if necessary, and RNA is reverse transcribed using gene specific promoters followed by RT-PCR.

The primers used for the amplification are selected so as to amplify a unique segment of the gene of interest (such as mRNA encoding one or more of the markers listed in Tables A, B, and C). In some embodiments, expression of other genes is also detected, such as the genes listed in Table 6 and Table 7. Primers that can be used to amplify mRNAs of interest are commercially available or can be designed and synthesized according to well-known methods.

An alternative quantitative nucleic acid amplification procedure is described in U.S. Pat. No. 5,219,727. In this procedure, the amount of a target sequence in a sample is determined by simultaneously amplifying the target sequence and an internal standard nucleic acid segment. The amount of amplified DNA from each segment is determined and compared to a standard curve to determine the amount of the target nucleic acid segment that was present in the sample prior to amplification.

In some examples, gene expression is identified or confirmed using the microarray technique. Thus, the expression profile can be measured in either fresh or paraffin-embedded tissue, using microarray technology. In this method, nucleic acid sequences of interest (including cDNAs and oligonucleotides) are plated, or arrayed, on a microchip substrate. The arrayed sequences are then hybridized with isolated nucleic acids (such as cDNA or mRNA) from cells or tissues of interest. Just as in the RT-PCR method, the source of mRNA typically is total RNA isolated from tissue or cells, and optionally from corresponding tissues or cells from a subject known not to be at risk for chlamydial PID.

In a specific embodiment of the microarray technique, PCR amplified inserts of cDNA clones are applied to a substrate in a dense array. In some examples, the array includes probes specific to markers listed in the Tables, or subsets of these markers. In some examples, probes specific for these nucleotide sequences are applied to the substrate, and the array can consist essentially of, or consist of these sequences. The microarrayed nucleic acids are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for genes of interest, such as those in the Tables. Microarray analysis can be performed by commercially available equipment, following manufacturer's protocols, such as are supplied with Affymetrix GENECHIP® technology (Affymetrix, Santa Clara, Calif.), or Agilent's microarray technology (Agilent Technologies, Santa Clara, Calif.).

Serial analysis of gene expression (SAGE) is another method that allows the simultaneous and quantitative analysis of a large number of gene transcripts, without the need of providing an individual hybridization probe for each transcript. First, a short sequence tag (about 10-14 base pairs) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag (see, for example, Velculescu et al., *Science* 270:484-7, 1995; and Velculescu et al., *Cell* 88:243-51, 1997).

In situ hybridization (ISH) is another method for detecting and comparing expression of genes of interest. ISH applies and extrapolates the technology of nucleic acid hybridization to the single cell level, and, in combination with the art of cytochemistry, immunocytochemistry and immunohistochemistry, permits the maintenance of morphology and the identification of cellular markers to be maintained and identified, and allows the localization of sequences to specific cells within populations, such as tissues and blood samples. ISH is a type of hybridization that uses a complementary nucleic acid to localize one or more specific nucleic acid sequences in a portion or section of tissue (in situ), or, if the tissue is small enough, in the entire tissue (whole mount ISH). RNA ISH can be used to assay expression patterns in a tissue, such as one or more of the markers listed in the Table. Sample cells or tissues are treated to increase their permeability to allow a probe to enter the cells. The probe is added to the treated cells, allowed to hybridize at pertinent temperature, and excess probe is washed away. A complementary probe is labeled so that the probe's location and quantity in the tissue can be determined, for example, using autoradiography, fluorescence microscopy or immunoassay. The sample may be any sample of interest.

In situ PCR is the PCR-based amplification of the target nucleic acid sequences prior to ISH. For detection of RNA, an intracellular reverse transcription step is introduced to generate complementary DNA from RNA templates prior to in situ PCR. This enables detection of low copy RNA sequences.

Prior to in situ PCR, cells or tissue samples are fixed and permeabilized to preserve morphology and permit access of the PCR reagents to the intracellular sequences to be amplified. PCR amplification of target sequences is next performed either in intact cells held in suspension or directly in cytocentrifuge preparations or tissue sections on glass slides. In the former approach, fixed cells suspended in the PCR reaction mixture are thermally cycled using conventional thermal cyclers. After PCR, the cells are cytocentrifuged onto glass slides with visualization of intracellular PCR products by ISH or immunohistochemistry. In situ PCR on glass slides is performed by overlaying the samples with the PCR mixture under a coverslip which is then sealed to prevent evaporation of the reaction mixture. Thermal cycling is achieved by placing the glass slides either directly on top of the heating block of a conventional or specially designed thermal cycler or by using thermal cycling ovens.

Detection of intracellular PCR products is generally achieved by one of two different techniques, indirect in situ PCR by ISH with PCR-product specific probes, or direct in situ PCR without ISH through direct detection of labeled nucleotides (such as digoxigenin-11-dUTP, fluorescein-dUTP, $^3$H-CTP or biotin-16-dUTP), which have been incorporated into the PCR products during thermal cycling.

In some embodiments of the detection methods, the expression of one or more "housekeeping" genes or "internal controls" can also be evaluated. These terms include any constitutively or globally expressed gene (or protein) whose presence enables an assessment of gene (or protein) levels. Such an assessment includes a determination of the overall constitutive level of gene transcription and a control for variations in RNA (or protein) recovery. The methods can also evaluate expression of other markers, such as one or more of the markers listed in Tables 6 and 7.

The concentration of the mRNA of interest, such as a mRNA corresponding to the markers listed in the Tables, that is detected is compared to a control, such as the concentration of the mRNA in a subject known not to have chlamydial PID. In other embodiments, the control is a standard value, such as a value that represents an average concentration of the mRNA of interest expected in a subject who does not have chlamydial PID.

Arrays

In particular embodiments provided herein, arrays can be used to evaluate gene expression. When describing an array that consists essentially of probes or primers specific for the genes listed in the Tables, such an array includes probes or primers specific for these genes, and can further include control probes (for example to confirm the incubation conditions are sufficient). In some examples, the array can consist essentially of probes or primers specific for the markers listed in the Tables A and B, and optionally includes probes or primers specific for the additional markers listed in Tables C and D. The array can further include one or more control probes. In some examples, the array may further include additional, such as about 5, 10, 20, 30, 40, 50, 60, or 70 additional nucleic acids, such as those corresponding to the markers listed in Tables A-D. Exemplary control probes include GAPDH, β-actin, and 18S RNA. In one example, an array is a multi-well plate (e.g., 96 or 384 well plate). The oligonucleotide probes or primers can further include one or more detectable labels, to permit detection of hybridization signals between the probe and target sequence (such as those listed in Tables A, B, C and D).

1. Array Substrates

The solid support of the array can be formed from an organic polymer. Suitable materials for the solid support include, but are not limited to: polypropylene, polyethylene, polybutylene, polyisobutylene, polybutadiene, polyisoprene, polyvinylpyrrolidine, polytetrafluoroethylene, polyvinylidene difluoride, polyfluoroethylene-propylene, polyethylenevinyl alcohol, polymethylpentene, polycholorotrifluoroethylene, polysulfornes, hydroxylated biaxially oriented polypropylene, aminated biaxially oriented polypropylene, thiolated biaxially oriented polypropylene, ethyleneacrylic acid, thylene methacrylic acid, and blends of copolymers thereof (see U.S. Pat. No. 5,985,567).

In general, suitable characteristics of the material that can be used to form the solid support surface include: being amenable to surface activation such that upon activation, the surface of the support is capable of covalently attaching a biomolecule such as an oligonucleotide thereto; amenability to "in situ" synthesis of biomolecules; being chemically inert such that at the areas on the support not occupied by the oligonucleotides or proteins (such as antibodies) are not amenable to non-specific binding, or when non-specific binding occurs, such materials can be readily removed from the surface without removing the oligonucleotides or proteins (such as antibodies).

In another example, a surface activated organic polymer is used as the solid support surface. One example of a surface activated organic polymer is a polypropylene material aminated via radio frequency plasma discharge. Other reactive groups can also be used, such as carboxylated, hydroxylated, thiolated, or active ester groups.

2. Array Formats

A wide variety of array formats can be employed in accordance with the present disclosure. One example includes a linear array of oligonucleotide bands, generally referred to in the art as a dipstick. Another suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use (see U.S. Pat. No. 5,981,185). In some examples, the array is a multi-well plate. In one example, the array is formed on a polymer medium, which is a thread, membrane or film. An example of an organic polymer medium is a polypropylene sheet having a thickness on the order of about 1 mil. (0.001 inch) to about 20 mil., although the thickness of the film is not critical and can be varied over a fairly broad range. The array can include biaxially oriented polypropylene (BOPP) films, which in addition to their durability, exhibit low background fluorescence.

The array formats of the present disclosure can be included in a variety of different types of formats. A "format" includes any format to which the solid support can be affixed, such as microtiter plates (e.g., multi-well plates), test tubes, inorganic sheets, dipsticks, and the like. For example, when the solid support is a polypropylene thread, one or more polypropylene threads can be affixed to a plastic dipstick-type device; polypropylene membranes can be affixed to glass slides. The particular format is, in and of itself, unimportant. All that is necessary is that the solid support can be affixed thereto without affecting the functional behavior of the solid support or any biopolymer absorbed thereon, and that the format (such as the dipstick or slide) is stable to any materials into which the device is introduced (such as clinical samples and hybridization solutions).

The arrays of the present disclosure can be prepared by a variety of approaches. In one example, oligonucleotide or protein sequences are synthesized separately and then attached to a solid support (see U.S. Pat. No. 6,013,789). In another example, sequences are synthesized directly onto the support to provide the desired array (see U.S. Pat. No. 5,554,501). Suitable methods for covalently coupling oligonucleotides and proteins to a solid support and for directly synthesizing the oligonucleotides or proteins onto the support are known to those working in the field; a summary of suitable methods can be found in Matson et al., *Anal. Biochem.* 217:306-10, 1994. In one example, the oligonucleotides are synthesized onto the support using conventional chemical techniques for preparing oligonucleotides on solid supports (such as PCT applications WO 85/01051 and WO 89/10977, or U.S. Pat. No. 5,554,501).

A suitable array can be produced using automated means to synthesize oligonucleotides in the cells of the array by laying down the precursors for the four bases in a predetermined pattern. Briefly, a multiple-channel automated chemical delivery system is employed to create oligonucleotide probe populations in parallel rows (corresponding in number to the number of channels in the delivery system) across the substrate. Following completion of oligonucleotide synthesis in a first direction, the substrate can then be rotated by 90° to permit synthesis to proceed within a second set of rows that are now perpendicular to the first set. This process creates a multiple-channel array whose intersection generates a plurality of discrete cells.

The oligonucleotides can be bound to the polypropylene support by either the 3' end of the oligonucleotide or by the 5' end of the oligonucleotide. In one example, the oligonucleotides are bound to the solid support by the 3' end. However, one of skill in the art can determine whether the use of the 3' end or the 5' end of the oligonucleotide is suitable for bonding to the solid support. In general, the internal complementarity of an oligonucleotide probe in the region of the 3' end and the 5' end determines binding to the support.

In particular examples, the oligonucleotide probes on the array include one or more labels, that permit detection of oligonucleotide probe:target sequence hybridization complexes.

Methods for Detection of Proteins

In some examples, the level of expression of one or more proteins is analyzed by detecting and quantifying the protein in a biological sample. In particular examples, one or more proteins corresponding to the markers, for example some or all of the markers listed in Tables A, B, C and/or D are analyzed. The disclosed assays can detect the protein corresponding to the some of markers listed in Tables A, B, C and/or D, and/or mRNA corresponding to some of the makers listed in Tables A, B, C and/or D.

Suitable biological samples include samples containing protein, such as blood, serum, plasma, urine, saliva, tissue biopsies, cells, including adipose cells or isolated blood cells, for example peripheral blood mononuclear cells, B cells, T cells and/or monocytes, and tissue samples, such as biopsy samples. Detecting an alteration in the amount of one or more (or all) of the proteins listed in Tables A, B, C and/or D, using the methods disclosed herein indicates the prognosis or diagnosis of the subject, or indicates if a therapy is effective for treating a subject as described above. In some embodiments, the expression level of one or more of the proteins listed in Table E is also assessed. Expression of proteins is the level of protein in a biological sample. Expression includes, but is not limited to, the production of the protein by translation of an mRNA and the half-life of the protein.

The expression level of the proteins can be evaluation using antibodies that specifically bind the markers listed in Tables A and B. The expression level of the proteins can be evaluation using antibodies that specifically bind the markers listed in Tables C and D.

In some embodiments, the method includes contacting the biological sample with one, more or all of an antibody that specifically binds TCL1A, an antibody that specifically binds HINT3, an antibody that specifically binds CDK5RAP3, an antibody that specifically binds FLJ35801, an antibody that specifically binds VPREB3, an antibody that specifically binds SULT1A1 (transcript variant 5), an antibody that specifically binds SULT1A1 (transcript variant 3), an antibody that specifically binds FCRLA, an antibody that specifically binds LOC100130562, an antibody that specifically binds SULT1A2, an antibody that specifically binds SLC4A1, an antibody that specifically binds LOC90925, an antibody that specifically binds MYOM2, an antibody that specifically binds CD19, an antibody that specifically binds LOC100132727, an antibody that specifically binds LOC100008588, an antibody that specifically binds CDCA7, an antibody that specifically binds TATDN3, an antibody that specifically binds LOC648729, an antibody that specifically binds HIST1H4H, an antibody that specifically binds MCM4, an antibody that specifically binds LOC642678, an antibody that specifically binds RPS15A, an antibody that specifically binds CKS2, an antibody that specifically binds LIMS1, an antibody that specifically binds OSBPL8, an antibody that specifically binds GRB2, an antibody that specifically binds LOC441763, an antibody that specifically binds SPATA13, an antibody that specifically binds TPM4, an antibody that specifically binds MCTP1, and an antibody that specifically binds SUMO3, an antibody that specifically binds LOC44173, and/or an antibody that specifically binds LOC100008588 protein. In other embodiments, the method includes contacting the biological sample or a component thereof with one, more or all of an antibody that specifically binds MYOM2, an antibody that specifically binds SLC4A1, an antibody that specifically binds LOC402251, an antibody that specifically binds LOC286444, an antibody that specifically binds FBXO7, an antibody that specifically binds TCL1A, an antibody that specifically binds LOC100130562, an antibody that specifically binds C5ORF28, an antibody that specifically binds LOC642989, an antibody that specifically binds CD79B, an antibody that specifically binds LOC643873, an antibody that specifically binds LOC100129742, an antibody that specifically binds VPREB3, an antibody that specifically binds LOC100133372, an antibody that specifically binds RPL13, an antibody that specifically binds SULT1A1 (transcript variant 5), an antibody that specifically binds CD19, an antibody that specifically binds CD79B, an antibody that specifically binds LOC100133583, an antibody that specifically binds CCR6, an antibody that specifically binds LOC642934, an antibody that specifically binds LOC100132727, an antibody that specifically binds LOC90925, an antibody that specifically binds PPA2, an antibody that specifically binds LOC100130053, an antibody that specifically binds SULT1A4, an antibody that specifically binds FCRLA, an antibody that specifically binds CDC42, an antibody that specifically binds CERK, an antibody that specifically binds SDHALP1, an antibody that specifically binds LOC100129237, an antibody that specifically binds HINT3, an antibody that specifically binds SULT1A1 (transcript variant 3), an antibody that specifically binds SULT1A2, an antibody that specifically binds CMPK1, an antibody that specifically binds MEF2D, an antibody that specifically binds C10ORF104, an antibody that specifically binds JAK1, an antibody that specifically binds LOC644739, an antibody that specifically binds HS.552082, an antibody that specifically binds KCNH6, an antibody that specifically binds RPL37A, an antibody that specifically binds CDK5RAP3, an antibody that specifically binds FLJ35801, an antibody that specifically binds CKS2, an antibody that specifically binds C10ORF105, an antibody that specifically binds CDCA7, an antibody that specifically binds HS.489254, an antibody that specifically binds MAX, an antibody that specifically binds GINS2, an antibody that specifically binds MCM4, an antibody that specifically binds LOC648729, an antibody that specifically binds TATDN3, an antibody that specifically binds MYD88, an antibody that specifically binds LEPROT, an antibody that specifically binds LOC645159, an antibody that specifically binds MSRA, an antibody that specifically binds TPM4, an antibody that specifically binds NAT8B, an antibody that specifically binds RTP4, GRB2, an antibody that specifically binds SUMO3, an antibody that specifically binds RPS15A, an antibody that specifically binds MCTP1, an antibody that specifically binds LOC642678, an antibody that specifically binds PROS1, an antibody that specifically binds NFKBIZ, an antibody that specifically binds PARP12, an antibody that specifically binds OSBPL8, an antibody that specifically binds SPATA13, an antibody that specifically binds LIMS1, an antibody that specifically binds HEBP1, an antibody that specifically binds HIST1H4H, an antibody that specifically binds LOC441763, an antibody that specifically binds LY6E, and/or an antibody that specifically binds LOC100008588.

Any standard immunoassay format (such as ELISA, Western blot, or RIA assay) can be used to measure protein levels. Immunohistochemical techniques can also be utilized. General guidance regarding such techniques can be found in Bancroft and Stevens (*Theory and Practice of Histological Techniques*, Churchill Livingstone, 1982) and Ausubel et al. (*Current Protocols in Molecular Biology*, John Wiley & Sons, New York, 1998), and Harlow & Lane, Antibodies, *A Laboratory Manual*, Cold Spring Harbor Publications, New York (1988); these references disclose a number of immunoassay formats and conditions that can be used to determine specific immunoreactivity. Generally, immunoassays include the use of one or more specific binding agents (such as antibodies) that specifically recognizes and can bind a molecule of interest, such a protein corresponding to a marker listed in Tables A, B, C and/or D. Such binding agents can include a detectable label (such as a radiolabel, fluorophore or enzyme), that permits detection of the binding to the protein and determination of relative or absolute quantities of the molecule of interest in the sample. Although the details of the immunoassays may vary with the particular format employed, the method of detecting the protein in a sample generally includes the steps of contacting the sample with an antibody, which specifically binds to the protein under immunologically reactive conditions to form an immune complex between the antibody and the protein, and detecting the presence of and/or quantity of the immune complex (bound antibody), either directly or indirectly. The antibody can be a polyclonal or monoclonal antibody, or fragment thereof. In some examples, the antibody is a humanized antibody. In additional examples, the antibody is a chimeric antibody.

The antibodies can be labeled. Suitable detectable markers are described and known to the skilled artisan. For example, various enzymes, prosthetic groups, fluorescent materials, luminescent materials, magnetic agents, and radioactive materials can be used. Non-limiting examples of suitable enzymes include horseradish peroxidase, alkaline phosphatase, beta-galactosidase, or acetylcholinesterase. Non-limiting examples of suitable prosthetic group complexes include streptavidin/biotinm and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary magnetic agent is gadolinium, and non-limiting exemplary radioactive labels include $^{125}$I, $^{131}$I, $^{35}$S or $^{3}$H. Additional examples are disclosed above.

In another embodiment, the antibody that binds the protein of interest (the first antibody) is unlabeled and a second antibody or other molecule that can bind the antibody that binds the protein of interest is utilized. As is well known to one of skill in the art, a second antibody is chosen that is able to specifically bind the specific species and class of the first antibody. For example, if the first antibody is a mouse IgG, then the secondary antibody may be a goat anti-mouse-IgG.

Other molecules that can bind to antibodies include, without limitation, Protein A and Protein G, both of which are available commercially.

Quantitation of proteins can be achieved by immunoassay. The amount of proteins can be assessed and optionally in a control sample. The amounts of protein in the sample from the subject of interest can be compared to levels of the protein found in samples form control subjects or to another control (such as a standard value or reference value). A significant increase or decrease in the amount can be evaluated using statistical methods known in the art.

In some non-limiting examples, a sandwich ELISA can be used to detect the presence or determine the amount of a protein in a sample. In this method, a solid surface is first coated with an antibody that specifically binds the protein of interest. The test sample containing the protein (such as, but not limited to, a blood, plasma, serum, or urine sample), is then added and the antigen is allowed to react with the bound antibody. Any unbound antigen is washed away. A known amount of enzyme-labeled protein-specific antibody is then allowed to react with the bound protein. Any excess unbound enzyme-linked antibody is washed away after the reaction. The substrate for the enzyme used in the assay is then added and the reaction between the substrate and the enzyme produces a color change. The amount of visual color change is a direct measurement of specific enzyme-conjugated bound antibody, and consequently the quantity of the protein present in the sample tested.

In an alternative example, a protein can be assayed in a biological sample by a competition immunoassay utilizing protein standards labeled with a detectable substance and an unlabeled antibody that specifically binds the protein of interest. In this assay, the biological sample (such as, but not limited to, a blood, plasma, serum, or urine sample), the labeled protein standards and the antibody that specifically binds the protein of interest are combined and the amount of labeled protein standard bound to the unlabeled antibody is determined. The amount of protein in the biological sample is inversely proportional to the amount of labeled protein standard bound to the antibody that specifically binds the protein of interest.

Mass spectrometry is particularly suited to the identification of proteins from biological samples, such those listed in Tables A, B, C and D. Mass spectrometry also is particularly useful in the quantitation of peptides in a biological sample, for example using isotopically labeled peptide standards. The application of mass spectrometric techniques to identify proteins in biological samples is known in the art and is described, for example, in Akhilesh et al., *Nature*, 405:837-846, 2000; Dutt et al., *Curr. Opin. Biotechnol.*, 11:176-179, 2000; Gygi et al., *Curr. Opin. Chem. Biol.*, 4 (5): 489-94, 2000; Gygi et al., *Anal. Chem.*, 72 (6): 1112-8, 2000; and Anderson et al., *Curr. Opin. Biotechnol.*, 11:408-412, 2000.

Separation of ions according to their m/z ratio can be accomplished with any type of mass analyzer, including quadrupole mass analyzers (Q), time-of-flight (TOF) mass analyzers (for example, linear or reflecting) analyzers, magnetic sector mass analyzers, 3D and linear ion traps (IT), Fourier-transform ion cyclotron resonance (FT-ICR) analyzers, Orbitrap analyzers (like LTQ-Orbitrap LC/MS/MS), and combinations thereof (for example, a quadrupole-time-of-flight analyzer, or Q-TOF analyzer). A triple quadropole instrument can be used such as the Q-trap.

In some embodiments, the mass spectrometric technique is tandem mass spectrometry (MS/MS). Typically, in tandem mass spectrometry a protein gene product, such as those from Table A, B, and/or C, entering the tandem mass spectrometer is selected and subjected to collision induced dissociation (CID). The spectrum of the resulting fragment ion is recorded in the second stage of the mass spectrometry, as a so-called CID or ETD spectrum. Because the CID or ETD process usually causes fragmentation at peptide bonds and different amino acids for the most part yield peaks of different masses, a CID or ETD spectrum alone often provides enough information to determine the presence of a the protein of Tables A, B, or C. Suitable mass spectrometer systems for MS/MS include an ion fragmentor and one, two, or more mass spectrometers, such as those described above. Examples of suitable ion fragmentors include, but are not limited to, collision cells (in which ions are fragmented by causing them to collide with neutral gas molecules), photo dissociation cells (in which ions are fragmented by irradiating them with a beam of photons), and surface dissociation fragmentor (in which ions are fragmented by colliding them with a solid or a liquid surface). Suitable mass spectrometer systems can also include ion reflectors.

Prior to mass spectrometry, the sample can be subjected to one or more dimensions of chromatographic separation, for example, one or more dimensions of liquid or size exclusion chromatography. Representative examples of chromatographic separation include paper chromatography, thin layer chromatography (TLC), liquid chromatography, column chromatography, high performance liquid chromatography (HPLC), fast protein liquid chromatography (FPLC), ion exchange chromatography, size exclusion chromatography, affinity chromatography, high performance liquid chromatography (HPLC), nano-reverse phase liquid chromatography (nano-RPLC), polyacrylamide gel electrophoresis (PAGE), capillary electrophoresis (CE), reverse phase high performance liquid chromatography (RP-HPLC) or other suitable chromatographic techniques. Thus, in some embodiments, the mass spectrometric technique is directly or indirectly coupled with a one, two or three dimensional liquid chromatography technique, such as column chromatography, high performance liquid chromatography (HPLC or FPLC), reversed phase, ion exchange chromatography, size exclusion chromatography, affinity chromatography (such as protein or peptide affinity chromatography, immunoaffinity chromatography, lectin affinity chromatography, etc.), or one, two or three dimensional polyacrylamide gel electrophoresis (PAGE), or one or two dimensional capillary electrophoresis (CE) to further resolve the biological sample prior to mass spectrometric analysis.

A variety of mass spectrometry methods, including iTRAQ® and MRM, can be used. In some embodiments, quantitative spectroscopic methods, such as SELDI, are used to analyze protein expression in a sample. In one example, surface-enhanced laser desorption-ionization time-of-flight (SELDI-TOF) mass spectrometry is used to detect protein expression, for example by using the PROTEINCHIP™ (Ciphergen Biosystems, Palo Alto, Calif.). Such methods are well known in the art (for example see U.S. Pat. No. 5,719,060; U.S. Pat. No. 6,897,072; and U.S. Pat. No. 6,881,586). SELDI is a solid phase method for desorption in which the analyte is presented to the energy stream on a surface that enhances analyte capture or desorption. Additional methods are disclosed in the examples section below.

Briefly, one version of SELDI uses a chromatographic surface with a chemistry that selectively captures analytes of interest, such as one or more proteins of interest. Chromatographic surfaces can be composed of hydrophobic, hydrophilic, ion exchange, immobilized metal, or other chemistries. For example, the surface chemistry can include binding functionalities based on oxygen-dependent, carbon-dependent, sulfur-dependent, and/or nitrogen-dependent means of covalent or noncovalent immobilization of analytes. The activated surfaces are used to covalently immobilize specific "bait" molecules such as antibodies, receptors, or oligonucleotides often used for biomolecular interaction studies such as protein-protein and protein-DNA interactions.

The surface chemistry allows the bound analytes to be retained and unbound materials to be washed away. Subsequently, analytes bound to the surface can be desorbed and analyzed by any of several means, for example using mass spectrometry. When the analyte is ionized in the process of desorption, such as in laser desorption/ionization mass spectrometry, the detector can be an ion detector. Mass spectrometers generally include means for determining the time-of-flight of desorbed ions. This information is converted to mass. However, one need not determine the mass of desorbed ions to resolve and detect them: the fact that ionized analytes strike the detector at different times provides detection and resolution of them. Alternatively, the analyte can be detectably labeled (for example with a fluorophore or radioactive isotope). In these cases, the detector can be a fluorescence or radioactivity detector.

In an additional example, the method may include detection of a protein of interest in a sample using an electrochemical immunoassay method. See, e.g., Yu et al., *J. Am. Chem. Soc.*, 128:11199-11205, 2006; Mani et al., *ACS Nano*, 3:585-594, 2009; Malhotra et al., *Anal. Chem.*, 82:3118-3123, 2010. In this method, an antibody that specifically binds the protein of interest is conjugated to terminally carboxylated single-wall carbon nanotubes (SWNT), multi-wall carbon nanotubes (MWCNT), or gold nanoparticles (AuNP), which are attached to a conductive surface. A sample (such as a blood, plasma or serum sample) is contacted with the SWNTs, MWCNTs, or AuNPs, and protein in the sample binds to the primary antibody. A second antibody conjugated directly or indirectly to a redox enzyme (such as horseradish peroxidase (HRP), cytochrome c, myoglobin, or glucose oxidase) binds to the primary antibody or to the protein (for example, in a "sandwich" assay). In some examples, the second antibody is conjugated to the enzyme. In other examples, the second antibody and the enzyme are both conjugated to a support (such as a magnetic bead). Signals are generated by adding enzyme substrate (e.g. hydrogen peroxide if the enzyme is HRP) to the solution bathing the sensor and measuring the current produced by the catalytic reduction.

In a particular example, the method includes a first antibody that specifically binds the protein of interest attached to an AuNP sensor surface. A sample (such as, but not limited to, a blood, plasma, serum, or urine sample) is contacted with the AuNP sensor including the first antibody. After the protein of interest binds to the first (capture) antibody (Ab1) on the electrode, a horseradish peroxidase (HRP)-labeled second antibody that specifically binds the protein of interest (HRP-Ab2) or beads conjugated to both a second antibody that binds the protein of interest and HRP are incubated with the sensor, allowing the second antibody to bind to the protein of interest. Biocatalytic electrochemical reduction produces a signal via reduction of peroxide activated enzyme following addition of hydrogen peroxide. Use of HRP is advantageous for arrays since immobilization of the electroactive enzyme label on the electrode eliminates electrochemical crosstalk between array elements, which can occur when detecting soluble electroactive product.

In some embodiments, iTRAQ® reagents are utilized. Multiple samples can be run simultaneously using different iTRAQ® reagents that label the individual samples with different mass identifiers. By way of example, sample one can be labeled with a mass identifier (or mass tag) that has a molecular weight of 114 amu, while sample two mass identifier (or mass tag) can have a molecular weight of 117. When the samples are combined and subjected to mass spectrometric analysis, a fragment peptide from sample two will have a predictable mass difference of three amu, compared to the same fragment peptide from sample one. In other words a peptide of identical sequence in sample one and sample two will be three amu heavier. This predictable mass difference can be used both to identify a peptide fragment (and hence the protein from which they were excised) and the relative quantities of each peptide in the samples.

In multiple reaction monitoring (MRM), tryptic peptides are used as markers for the abundance of specific proteins of interest, such as those listed in Tables A, B, and C. This selection is relatively straightforward if the protein has been identified by MS, such that the peptides are observable in a mass spectrometer (for example an LTQ Orbitrap). The process of establishing an MRM assay for a protein consists of a number of steps: 1) selection of the appropriate peptide(s) unique to the protein of interest and showing high MS signal response (prototypic peptides) which will help maximize the sensitivity of the assay; 2) selection of predominant peptide fragments specific (MS/MS) for the parent peptide (useful MRM transition); 3) for each peptide-fragment pair, optimization of specific MS parameters (for example, the collision energy) to maximize the signal response/sensitivity; 4) validation of the MRM assay to confirm peptide identity, for example by acquiring a full MS2 spectrum of the peptide in the triple quadrupole MS instrument used for MRM; 5) extraction of the final "coordinates" of the MRM assay, including the selected peptide and peptide fragments, the corresponding mass-to-charge ratios, the fragment intensity ratios, the associated collision energy, and the chromatographic elution time to be optionally used in time-constrained MRM analyses. In some examples, isotopically labeled internal peptide standards (with known concentrations determined by amino acid analysis) are used to facilitate absolute quantitation of selected peptides.

The concentration of the protein of interest, such as a protein corresponding to the markers listed in Tables A, B, C and D, that is detected can be compared to a control, such as the concentration of the protein in a subject known not to have chlamydial PID. In other embodiments, the control is a standard value, such as a value that represents an average concentration of the protein of interest expected in a subject who does not have chlamydial PID.

Kits

Kits are also provided. The kit can include probes, primers, or antibodies specific for the genes listed in Table A, Table B, Table C and/or Table D, and can further include control probes, primers, and antibodies (for example to confirm the incubation conditions are sufficient). The kit can further include one or more control probes, primers and/or antibodies.

The kit can include a container and a label or package insert on or associated with the container. Suitable containers include, for example, bottles, vials, syringes, etc. The containers may be formed from a variety of materials such as glass or plastic. The container typically holds a composition including one or more of the probes, primers and/or antibodies. In several embodiments the container may have a sterile access port.

A label or package insert indicates that the composition is of use for evaluating if a subject is at risk for chlamydial PID or if a therapeutic agent is of use of the treatment of a subject. The label or package insert typically will further include instructions for use, such as particular assay conditions. The package insert typically includes instructions customarily included in commercial packages of products that contain information about the indications, usage, contraindications and/or warnings concerning the use of such products. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

The following examples are provided to illustrate certain particular features and/or embodiments. These examples should not be construed to limit the disclosure to the particular features or embodiments described.

EXEMPLARY EMBODIMENTS

Clause 1: A method of detecting chlamydial pelvic inflammatory disease in a female subject, comprising: performing one or more assays that detect a level of TCL1A, HINT3, CDK5RAP3, FLJ35801, VPREB3, SULT1A1 (transcript variant 5), SULT1A1 (transcript variant 3), FCRLA, LOC100130562, SULT1A2, SLC4A1, LOC90925, MYOM2, CD19, LOC100132727, LOC100008588, CDCA7, TATDN3, LOC648729, HIST1H4H, MCM4, LOC642678, RPS15A, CKS2, LIMS1, OSBPL8, GRB2, LOC441763, SPATA13, TPM4, MCTP1, and SUMO3 in a biological sample from the subject; and comparing the level of TCL1A, HINT3, CDK5RAP3, FLJ35801, VPREB3, SULT1A1 (transcript variant 5), SULT1A1 (transcript variant 3), FCRLA, LOC100130562, SULT1A2, SLC4A1, LOC90925, MYOM2, CD19, LOC100132727, LOC100008588, CDCA7, TATDN3, LOC648729, HIST1H4H, MCM4, LOC642678, RPS15A, CKS2, LIMS1, OSBPL8, GRB2, LOC441763, SPATA13, TPM4, MCTP1, SUMO3 to a respective control level of TCL1A, HINT3, CDK5RAP3, FLJ35801, VPREB3, SULT1A1 (transcript variant 5), SULT1A1 (transcript variant 3), FCRLA, LOC100130562, SULT1A2, SLC4A1, LOC90925, MYOM2, CD19, LOC100132727, LOC100008588, CDCA7, TATDN3, LOC648729, HIST1H4H, MCM4, LOC642678, RPS15A, CKS2, LIMS1, OSBPL8, GRB2, LOC441763, SPATA13, TPM4, MCTP1, and SUMO3, respectively; wherein detection of a decrease in the level of TCL1A, HINT3, CDK5RAP3, FLJ35801, VPREB3, SULT1A1 (transcript variant 5), SULT1A1 (transcript variant 3), FCRLA, LOC100130562, SULT1A2, SLC4A1, LOC90925, MYOM2, CD19, LOC100132727, and an increase in the level of LOC100008588, CDCA7, TATDN3, LOC648729, HIST1H4H, MCM4, LOC642678, RPS15A, CKS2, LIMS1, OSBPL8, GRB2, LOC441763, SPATA13, TPM4, MCTP1, and SUMO3, as compared to the respective control indicates that the subject has chlamydial pelvic inflammatory disease. All of these makers can be detected. Nucleic acids and/or proteins can be detected.

Clause 2: The method of clause 1, further comprising: performing one or more assays that detect a level of MYOM2, SLC4A1, LOC402251, LOC286444, FBXO7, TCL1A, LOC100130562, C5ORF28, LOC642989, CD79B, LOC643873, LOC100129742, VPREB3, LOC100133372, RPL13, SULT1A1 (transcript variant 5), CD19, CD79B, LOC100133583, CCR6, LOC642934, LOC100132727, LOC90925, PPA2, LOC100130053, SULT1A4, FCRLA, CDC42, CERK, SDHALP1, LOC100129237, HINT3, SULT1A1 (transcript variant 3), SULT1A2, CMPK1, MEF2D, C10ORF104, JAK1, LOC644739, HS.552082, KCNH6, RPL37A, CDK5RAP3, FLJ35801, FBLN1, CKS2, C10ORF105, CDCA7, HS.489254, MAX, GINS2, MCM4, LOC648729, TATDN3, MYD88, LEPROT, LOC645159, MSRA, TPM4, NAT8B, RTP4, GRB2, SUMO3, RPS15A, MCTP1, LOC642678, PROS1, NFKBIZ, PARP12, OSBPL8, SPATA13, LIMS1, HEBP1, HIST1H4H, LOC441763, LY6E, and LOC100008588 in a biological sample from the subject; and comparing the level of MYOM2, SLC4A1, LOC402251, LOC286444, FBXO7, TCL1A, LOC100130562, C5ORF28, LOC642989, CD79B, LOC643873, LOC100129742, VPREB3, LOC100133372, RPL13, SULT1A1 (transcript variant 5), CD19, CD79B, LOC100133583, CCR6, LOC642934, LOC100132727, LOC90925, PPA2, LOC100130053, SULT1A4, FCRLA, CDC42, CERK, SDHALP1, LOC100129237, HINT3, SULT1A1 (transcript variant 3), SULT1A2, CMPK1, MEF2D, C10ORF104, JAK1, LOC644739, HS.552082, KCNH6, RPL37A, CDK5RAP3, FLJ35801, CKS2, C10ORF105, CDCA7, HS.489254, MAX, GINS2, MCM4, LOC648729, TATDN3, MYD88, LEPROT, LOC645159, MSRA, TPM4, NAT8B, RTP4, GRB2, SUMO3, RPS15A, MCTP1, LOC642678, PROS1, NFKBIZ, PARP12, OSBPL8, SPATA13, LIMS1, HEBP1, HIST1H4H, LOC441763, LY6E, and LOC100008588 to a respective control level of MYOM2, SLC4A1, LOC402251, LOC286444, FBXO7, TCL1A, LOC100130562, C5ORF28, LOC642989, CD79B, LOC643873, LOC100129742, VPREB3, LOC100133372, RPL13, SULT1A1 (transcript variant 5), CD19, CD79B, LOC100133583, CCR6, LOC642934, LOC100132727, LOC90925, PPA2, LOC100130053, SULT1A4, FCRLA, CDC42, CERK, SDHALP1, LOC100129237, HINT3, SULT1A1 (transcript variant 3), SULT1A2, CMPK1, MEF2D, C10ORF104, JAK1, LOC644739, HS.552082, KCNH6, RPL37A, CDK5RAP3, FLJ35801, CKS2, C10ORF105, CDCA7, HS.489254, MAX, GINS2, MCM4, LOC648729, TATDN3, MYD88, LEPROT, LOC645159, MSRA, TPM4, NAT8B, RTP4, GRB2, SUMO3, RPS15A, MCTP1, LOC642678, PROS1, NFKBIZ, PARP12, OSBPL8, SPATA13, LIMS1, HEBP1, HIST1H4H, LOC441763, LY6E, and LOC100008588; wherein detection of a decrease in the level of MYOM2, SLC4A1, LOC402251, LOC286444, FBXO7, TCL1A, LOC100130562, C5ORF28, LOC642989, CD79B, LOC643873, LOC100129742, VPREB3, LOC100133372, RPL13, SULT1A1 (transcript variant 5), CD19, CD79B, LOC100133583, CCR6, LOC642934, LOC100132727, LOC90925, PPA2, LOC100130053, SULT1A4, FCRLA, CDC42, CERK, SDHALP1, LOC100129237, HINT3, SULT1A1 (transcript variant 3), SULT1A2, CMPK1, MEF2D, C10ORF104, JAK1, LOC644739, HS.552082, KCNH6, RPL37A, CDK5RAP3, and FLJ35801, and an increase in the level of FBLN1, CKS2, C10ORF105, CDCA7, HS.489254, MAX, GINS2, MCM4, LOC648729, TATDN3, MYD88, LEPROT, LOC645159, MSRA, TPM4, NAT8B, RTP4, GRB2, SUMO3, RPS15A, MCTP1, LOC642678, PROS1, NFKBIZ, PARP12, OSBPL8, SPATA13, LIMS1, HEBP1, HIST1H4H, LOC441763, LY6E, and LOC100008588, as compared to the respective control indicates that the subject has chlamydial pelvic inflammatory disease. All of these makers can be detected. Nucleic acids and/or proteins can be detected.

Clause 3: A method of determining the likelihood that a female subject will develop damage to a reproductive organ from a *chlamydia* infection, comprising: performing one or more assays that detect a level TCL1A, HINT3, CDK5RAP3, FLJ35801, VPREB3, SULT1A1 (transcript variant 5), SULT1A1 (transcript variant 3), FCRLA, LOC100130562, SULT1A2, SLC4A1, LOC90925, MYOM2, CD19, LOC100132727, LOC100008588, CDCA7, TATDN3, LOC648729, HIST1H4H, MCM4, LOC642678, RPS15A, CKS2, LIMS1, OSBPL8, GRB2, LOC441763, SPATA13, TPM4, MCTP1, and SUMO3 in a biological sample from the subject; and comparing the level of TCL1A, HINT3, CDK5RAP3, FLJ35801, VPREB3, SULT1A1 (transcript variant 5), SULT1A1 (transcript variant 3), FCRLA, LOC100130562, SULT1A2, SLC4A1, LOC90925, MYOM2, CD19, LOC100132727, LOC100008588, CDCA7, TATDN3, LOC648729, HIST1H4H, MCM4, LOC642678, RPS15A, CKS2, LIMS1, OSBPL8, GRB2, LOC441763, SPATA13, TPM4, MCTP1, and SUMO3 to a respective control level of TCL1A, HINT3, CDK5RAP3, FLJ35801, VPREB3, SULT1A1 (transcript variant 5), SULT1A1 (transcript variant 3), FCRLA, LOC100130562, SULT1A2, SLC4A1, LOC90925, MYOM2, CD19, LOC100132727, LOC100008588, CDCA7, TATDN3, LOC648729, HIST1H4H, MCM4, LOC642678, RPS15A, CKS2, LIMS1, OSBPL8, GRB2, LOC441763, SPATA13, TPM4, MCTP1, and SUMO3; wherein detection of a decrease in the level of TCL1A, HINT3, CDK5RAP3, FLJ35801, VPREB3, SULT1A1 (transcript variant 5), SULT1A1 (transcript variant 3), FCRLA, LOC100130562, SULT1A2, SLC4A1, LOC90925, MYOM2, CD19, and LOC100132727, and an increase in the level of LOC100008588, CDCA7, TATDN3, LOC648729, HIST1H4H, MCM4, LOC642678, RPS15A, CKS2, LIMS1, OSBPL8, GRB2, LOC441763, SPATA13, TPM4, MCTP1, and SUMO3, as compared to the respective control indicates that the subject will develop damage to a reproductive organ from a *chlamydia* infection. All of these makers can be detected. Nucleic acids and/or proteins can be detected.

Clause 4: The method of clause 3, further comprising: performing one or more assays that detect a level of MYOM2, SLC4A1, LOC402251, LOC286444, FBXO7, TCL1A, LOC100130562, C5ORF28, LOC642989, CD79B, LOC643873, LOC100129742, VPREB3, LOC100133372, RPL13, SULT1A1 (transcript variant 5), CD19, CD79B, LOC100133583, CCR6, LOC642934, LOC100132727, LOC90925, PPA2, LOC100130053, SULT1A4, FCRLA, CDC42, CERK, SDHALP1, LOC100129237, HINT3, SULT1A1 (transcript variant 3), SULT1A2, CMPK1, MEF2D, C10ORF104, JAK1, LOC644739, HS.552082, KCNH6, RPL37A, CDK5RAP3, and FLJ3580, FBLN1, CKS2, C10ORF105, CDCA7, HS.489254, MAX, GINS2, MCM4, LOC648729, TATDN3, MYD88, LEPROT, LOC645159, MSRA, TPM4, NAT8B, RTP4, GRB2, SUMO3, RPS15A, MCTP1, LOC642678, PROS1, NFKBIZ, PARP12, OSBPL8, SPATA13, LIMS1, HEBP1, HIST1H4H, LOC441763, LY6E, and LOC100008588 in a biological sample from the subject; and comparing the level of MYOM2, SLC4A1, LOC402251, LOC286444, FBXO7, TCL1A, LOC100130562, C5ORF28, LOC642989, CD79B, LOC643873, LOC100129742, VPREB3, LOC100133372, RPL13, SULT1A1 (transcript variant 5), CD19, CD79B, LOC100133583, CCR6, LOC642934, LOC100132727, LOC90925, PPA2, LOC100130053, SULT1A4, FCRLA, CDC42, CERK, SDHALP1, LOC100129237, HINT3, SULT1A1 (transcript variant 3), SULT1A2, CMPK1, MEF2D, C10ORF104, JAK1, LOC644739, HS.552082, KCNH6, RPL37A, CDK5RAP3, FLJ35801, CKS2, C10ORF105, CDCA7, HS.489254, MAX, GINS2, MCM4, LOC648729, TATDN3, MYD88, LEPROT, LOC645159, MSRA, TPM4, NAT8B, RTP4, GRB2, SUMO3, RPS15A, MCTP1, LOC642678, PROS1, NFKBIZ, PARP12, OSBPL8, SPATA13, LIMS1, HEBP1, HIST1H4H, LOC441763, LY6E, and LOC100008588 to a respective control level of MYOM2, SLC4A1, LOC402251, LOC286444, FBXO7, TCL1A, LOC100130562, C5ORF28, LOC642989, CD79B, LOC643873, LOC100129742, VPREB3, LOC100133372, RPL13, SULT1A1 (transcript variant 5), CD19, CD79B, LOC100133583, CCR6, LOC642934, LOC100132727, LOC90925, PPA2, LOC100130053, SULT1A4, FCRLA, CDC42, CERK, SDHALP1, LOC100129237, HINT3, SULT1A1 (transcript variant 3), SULT1A2, CMPK1, MEF2D, C10ORF104, JAK1, LOC644739, HS.552082, KCNH6, RPL37A, CDK5RAP3, FLJ35801, CKS2, C10ORF105, CDCA7, HS.489254, MAX, GINS2, MCM4, LOC648729, TATDN3, MYD88, LEPROT, LOC645159, MSRA, TPM4, NAT8B, RTP4, GRB2, SUMO3, RPS15A, MCTP1, LOC642678, PROS1, NFKBIZ, PARP12, OSBPL8, SPATA13, LIMS1, HEBP1, HIST1H4H, LOC441763, LY6E, and LOC100008588; wherein detection of a decrease in the level of MYOM2, SLC4A1, LOC402251, LOC286444, FBXO7, TCL1A, LOC100130562, C5ORF28, LOC642989, CD79B, LOC643873, LOC100129742, VPREB3, LOC100133372, RPL13, SULT1A1 (transcript variant 5), CD19, CD79B, LOC100133583, CCR6, LOC642934, LOC100132727, LOC90925, PPA2, LOC100130053, SULT1A4, FCRLA, CDC42, CERK, SDHALP1, LOC100129237, HINT3, SULT1A1 (transcript variant 3), SULT1A2, CMPK1, MEF2D, C10ORF104, JAK1, LOC644739, HS.552082, KCNH6, RPL37A, CDK5RAP3, and FLJ35801, and an increase in FBLN1, CKS2, C10ORF105, CDCA7, HS.489254, MAX, GINS2, MCM4, LOC648729, TATDN3, MYD88, LEPROT, LOC645159, MSRA, TPM4, NAT8B, RTP4, GRB2, SUMO3, RPS15A, MCTP1, LOC642678, PROS1, NFKBIZ, PARP12, OSBPL8, SPATA13, LIMS1, HEBP1, HIST1H4H, LOC441763, LY6E, and LOC100008588, as compared to the respective control indicates that that the subject will develop damage to a reproductive organ from a *chlamydia* infection. All of these makers can be detected. Nucleic acids and/or proteins can be detected.

Clause 5: The method of clause 3 or clause 4, wherein the subject has a *chlamydia* infection. Clause 6: The method of clause 3 or clause 4, wherein the subject does not have a *chlamydia* infection.

Clause 7: The method of any one of clauses 1-4, further comprising administering to the subject a therapeutically effective amount of azithromycin, doxycycline, erythromycin, amoxicillin or ofloxacin.

Clause 8: A method of determining if a pharmaceutical agent is effective for treatment or prevention of chlamydial pelvic inflammatory disease in a female subject, comprising: performing one or more assays that detect a level of TCL1A, HINT3, CDK5RAP3, FLJ35801, VPREB3, SULT1A1

(transcript variant 5), SULT1A1 (transcript variant 3), FCRLA, LOC100130562, SULT1A2, SLC4A1, LOC90925, MYOM2, CD19, LOC100132727, LOC100008588, CDCA7, TATDN3, LOC648729, HIST1H4H, MCM4, LOC642678, RPS15A, CKS2, LIMS1, OSBPL8, GRB2, LOC441763, SPATA13, TPM4, MCTP1, and SUMO3 in a biological sample from the subject; and comparing the level of TCL1A, HINT3, CDK5RAP3, FLJ35801, VPREB3, SULT1A1 (transcript variant 5), SULT1A1 (transcript variant 3), FCRLA, LOC100130562, SULT1A2, SLC4A1, LOC90925, MYOM2, CD19, LOC100132727, LOC100008588, CDCA7, TATDN3, LOC648729, HIST1H4H, MCM4, LOC642678, RPS15A, CKS2, LIMS1, OSBPL8, GRB2, LOC441763, SPATA13, TPM4, MCTP1, and SUMO3 to a respective control level of these markers; wherein detection of a decrease in the level of TCL1A, HINT3, CDK5RAP3, FLJ35801, VPREB3, SULT1A1 (transcript variant 5), SULT1A1 (transcript variant 3), FCRLA, LOC100130562, SULT1A2, SLC4A1, LOC90925, MYOM2, CD19, and LOC100132727, and an increase in the level of LOC100008588, CDCA7, TATDN3, LOC648729, HIST1H4H, MCM4, LOC642678, RPS15A, CKS2, LIMS1, OSBPL8, GRB2, LOC441763, SPATA13, TPM4, MCTP1, SUMO3, as compared to the respective control level of TCL1A, HINT3, CDK5RAP3, FLJ35801, VPREB3, SULT1A1 (transcript variant 5), SULT1A1 (transcript variant 3), FCRLA, LOC100130562, SULT1A2, SLC4A1, LOC90925, MYOM2, CD19, LOC100132727, LOC100008588, CDCA7, TATDN3, LOC648729, HIST1H4H, MCM4, LOC642678, RPS15A, CKS2, LIMS1, OSBPL8, GRB2, LOC441763, SPATA13, TPM4, MCTP1, and SUMO3, indicates that the pharmacologic agent is effective for treating the chlamydial pelvic inflammatory disease. All of these makers can be detected. Nucleic acids and/or proteins can be detected.

Clause 9: The method of clause 8, further comprising: performing one or more assays that detect a level of MYOM2, SLC4A1, LOC402251, LOC286444, FBXO7, TCL1A, LOC100130562, C5ORF28, LOC642989, CD79B, LOC643873, LOC100129742, VPREB3, LOC100133372, RPL13, SULT1A1 (transcript variant 5), CD19, CD79B, LOC100133583, CCR6, LOC642934, LOC100132727, LOC90925, PPA2, LOC100130053, SULT1A4, FCRLA, CDC42, CERK, SDHALP1, LOC100129237, HINT3, SULT1A1 (transcript variant 3), SULT1A2, CMPK1, MEF2D, C10ORF104, JAK1, LOC644739, HS.552082, KCNH6, RPL37A, CDK5RAP3, FLJ3580, FBLN1, CKS2, C10ORF105, CDCA7, HS.489254, MAX, GINS2, MCM4, LOC648729, TATDN3, MYD88, LEPROT, LOC645159, MSRA, TPM4, NAT8B, RTP4, GRB2, SUMO3, RPS15A, MCTP1, LOC642678, PROS1, NFKBIZ, PARP12, OSBPL8, SPATA13, LIMS1, HEBP1, HIST1H4H, LOC441763, LY6E, and LOC100008588 in a biological sample from the subject; and comparing the level of MYOM2, SLC4A1, LOC402251, LOC286444, FBXO7, TCL1A, LOC100130562, C5ORF28, LOC642989, CD79B, LOC643873, LOC100129742, VPREB3, LOC100133372, RPL13, SULT1A1 (transcript variant 5), CD19, CD79B, LOC100133583, CCR6, LOC642934, LOC100132727, LOC90925, PPA2, LOC100130053, SULT1A4, FCRLA, CDC42, CERK, SDHALP1, LOC100129237, HINT3, SULT1A1 (transcript variant 3), SULT1A2, CMPK1, MEF2D, C10ORF104, JAK1, LOC644739, HS.552082, KCNH6, RPL37A, CDK5RAP3, FLJ35801, CKS2, C10ORF105, CDCA7, HS.489254, MAX, GINS2, MCM4, LOC648729, TATDN3, MYD88, LEPROT, LOC645159, MSRA, TPM4, NAT8B, RTP4, GRB2, SUMO3, RPS15A, MCTP1, LOC642678, PROS1, NFKBIZ, PARP12, OSBPL8, SPATA13, LIMS1, HEBP1, HIST1H4H, LOC441763, LY6E, and LOC100008588 to a respective control level of MYOM2, SLC4A1, LOC402251, LOC286444, FBXO7, TCL1A, LOC100130562, C5ORF28, LOC642989, CD79B, LOC643873, LOC100129742, VPREB3, LOC100133372, RPL13, SULT1A1 (transcript variant 5), CD19, CD79B, LOC100133583, CCR6, LOC642934, LOC100132727, LOC90925, PPA2, LOC100130053, SULT1A4, FCRLA, CDC42, CERK, SDHALP1, LOC100129237, HINT3, SULT1A1 (transcript variant 3), SULT1A2, CMPK1, MEF2D, C10ORF104, JAK1, LOC644739, HS.552082, KCNH6, RPL37A, CDK5RAP3, FLJ35801, CKS2, C10ORF105, CDCA7, HS.489254, MAX, GINS2, MCM4, LOC648729, TATDN3, MYD88, LEPROT, LOC645159, MSRA, TPM4, NAT8B, RTP4, GRB2, SUMO3, RPS15A, MCTP1, LOC642678, PROS1, NFKBIZ, PARP12, OSBPL8, SPATA13, LIMS1, HEBP1, HIST1H4H, LOC441763, LY6E, and LOC100008588; wherein detection of a decrease in the level of MYOM2, SLC4A1, LOC402251, LOC286444, FBXO7, TCL1A, LOC100130562, C5ORF28, LOC642989, CD79B, LOC643873, LOC100129742, VPREB3, LOC100133372, RPL13, SULT1A1 (transcript variant 5), CD19, CD79B, LOC100133583, CCR6, LOC642934, LOC100132727, LOC90925, PPA2, LOC100130053, SULT1A4, FCRLA, CDC42, CERK, SDHALP1, LOC100129237, HINT3, SULT1A1 (transcript variant 3), SULT1A2, CMPK1, MEF2D, C10ORF104, JAK1, LOC644739, HS.552082, KCNH6, RPL37A, CDK5RAP3, and FLJ35801, and an increase in the level of FBLN1, CKS2, C10ORF105, CDCA7, HS.489254, MAX, GINS2, MCM4, LOC648729, TATDN3, MYD88, LEPROT, LOC645159, MSRA, TPM4, NAT8B, RTP4, GRB2, SUMO3, RPS15A, MCTP1, LOC642678, PROS1, NFKBIZ, PARP12, OSBPL8, SPATA13, LIMS1, HEBP1, HIST1H4H, LOC441763, LY6E, and LOC100008588, as compared to the respective control level of MYOM2, SLC4A1, LOC402251, LOC286444, FBXO7, TCL1A, LOC100130562, C5ORF28, LOC642989, CD79B, LOC643873, LOC100129742, VPREB3, LOC100133372, RPL13, SULT1A1 (transcript variant 5), CD19, CD79B, LOC100133583, CCR6, LOC642934, LOC100132727, LOC90925, PPA2, LOC100130053, SULT1A4, FCRLA, CDC42, CERK, SDHALP1, LOC100129237, HINT3, SULT1A1 (transcript variant 3), SULT1A2, CMPK1, MEF2D, C10ORF104, JAK1, LOC644739, HS.552082, KCNH6, RPL37A, CDK5RAP3, FLJ35801, CKS2, C10ORF105, CDCA7, HS.489254, MAX, GINS2, MCM4, LOC648729, TATDN3, MYD88, LEPROT, LOC645159, MSRA, TPM4, NAT8B, RTP4, GRB2, SUMO3, RPS15A, MCTP1, LOC642678, PROS1, NFKBIZ, PARP12, OSBPL8, SPATA13, LIMS1, HEBP1, HIST1H4H, LOC441763, LY6E, and LOC100008588 indicates that the pharmacologic agent is effective for treating the chlamydial pelvic inflammatory disease. All of these makers can be detected. Nucleic acids and/or proteins can be detected.

Clause 10: The method of any one of clauses 1-9, wherein the sample comprises a blood, tissue, plasma or serum sample.

Clause 11: The method of any one of clauses 1-10, further comprising assessing the clinical risk factors for the subject.

Clause 12: The method of any one of clauses 1-11, wherein the one or more assays detects mRNA.

Clause 13: The method of clause 12, wherein comprising performing a polymerase chain reaction, a microarray analysis or a hybridization reaction.

Clause 14: The method of clause 12, comprising performing reverse transcriptase polymerase chain reaction (RT-PCR).

Clause 15: The method of clause 8, comprising contacting the biological sample with a microarray.

Clause 16: The method of any one of clauses 1-11, wherein the one or more assays detects protein.

Clause 17: The method of clause 16, comprising performing a Western blot, an enzyme linked immunosorbent assay, or a radioimmunoassay on the biological sample.

Clause 18: The method of clause 16, comprising performing mass spectrometry on the biological sample.

Clause 19: The method of claim 16, wherein performing the one or more assays that detect protein comprises contacting the biological sample with an antibody that specifically binds TCL1A, an antibody that specifically binds HINT3, an antibody that specifically binds CDK5RAP3, an antibody that specifically binds FLJ35801, an antibody that specifically binds VPREB3, an antibody that specifically binds SULT1A1 (transcript variant 5), an antibody that specifically binds SULT1A1 (transcript variant 3), an antibody that specifically binds FCRLA, an antibody that specifically binds LOC100130562, an antibody that specifically binds SULT1A2, an antibody that specifically binds SLC4A1, an antibody that specifically binds LOC90925, an antibody that specifically binds MYOM2, an antibody that specifically binds CD19, an antibody that specifically binds LOC100132727, an antibody that specifically binds LOC100008588, an antibody that specifically binds CDCA7, an antibody that specifically binds TATDN3, an antibody that specifically binds LOC648729, an antibody that specifically binds HIST1H4H, an antibody that specifically binds MCM4, an antibody that specifically binds LOC642678, an antibody that specifically binds RPS15A, an antibody that specifically binds CKS2, an antibody that specifically binds LIMS1, an antibody that specifically binds OSBPL8, an antibody that specifically binds GRB2, an antibody that specifically binds LOC441763, an antibody that specifically binds SPATA13, an antibody that specifically binds TPM4, an antibody that specifically binds MCTP1, and an antibody that specifically binds SUMO3, and/or an antibody that specifically binds LOC100008588 protein. One or more of these antibodies can be used.

Clause 20: The method of clause 14, wherein performing the one or more assays that detect protein comprises contacting the biological sample or a component thereof with an antibody that specifically binds MYOM2, an antibody that specifically binds SLC4A1, an antibody that specifically binds LOC402251, an antibody that specifically binds LOC286444, an antibody that specifically binds FBXO7, an antibody that specifically binds TCL1A, an antibody that specifically binds LOC100130562, an antibody that specifically binds C5ORF28, an antibody that specifically binds LOC642989, an antibody that specifically binds CD79B, an antibody that specifically binds LOC643873, an antibody that specifically binds LOC100129742, an antibody that specifically binds VPREB3, an antibody that specifically binds LOC100133372, an antibody that specifically binds RPL13, an antibody that specifically binds SULT1A1 (transcript variant 5), an antibody that specifically binds CD19, an antibody that specifically binds CD79B, an antibody that specifically binds LOC100133583, an antibody that specifically binds CCR6, an antibody that specifically binds LOC642934, an antibody that specifically binds LOC100132727, an antibody that specifically binds LOC90925, an antibody that specifically binds PPA2, an antibody that specifically binds LOC100130053, an antibody that specifically binds SULT1A4, an antibody that specifically binds FCRLA, an antibody that specifically binds CDC42, an antibody that specifically binds CERK, an antibody that specifically binds SDHALP1, an antibody that specifically binds LOC100129237, an antibody that specifically binds HINT3, an antibody that specifically binds SULT1A1 (transcript variant 3), an antibody that specifically binds SULT1A2, an antibody that specifically binds CMPK1, an antibody that specifically binds MEF2D, an antibody that specifically binds C10ORF104, an antibody that specifically binds JAK1, an antibody that specifically binds LOC644739, an antibody that specifically binds HS.552082, an antibody that specifically binds KCNH6, an antibody that specifically binds RPL37A, an antibody that specifically binds CDK5RAP3, an antibody that specifically binds FLJ35801, an antibody that specifically binds CKS2, an antibody that specifically binds C10ORF105, an antibody that specifically binds CDCA7, an antibody that specifically binds HS.489254, an antibody that specifically binds MAX, an antibody that specifically binds GINS2, an antibody that specifically binds MCM4, an antibody that specifically binds LOC648729, an antibody that specifically binds TATDN3, an antibody that specifically binds MYD88, an antibody that specifically binds LEPROT, an antibody that specifically binds LOC645159, an antibody that specifically binds MSRA, an antibody that specifically binds TPM4, an antibody that specifically binds NAT8B, an antibody that specifically binds RTP4, GRB2, an antibody that specifically binds SUMO3, an antibody that specifically binds RPS15A, an antibody that specifically binds MCTP1, an antibody that specifically binds LOC642678, an antibody that specifically binds PROS1, an antibody that specifically binds NFKBIZ, an antibody that specifically binds PARP12, an antibody that specifically binds OSBPL8, an antibody that specifically binds SPATA13, an antibody that specifically binds LIMS1, an antibody that specifically binds HEBP1, an antibody that specifically binds HIST1H4H, an antibody that specifically binds LOC441763, an antibody that specifically binds LY6E, and/or an antibody that specifically binds LOC100008588. One or more of these antibodies can be used.

Clause 21: The method of any one of clauses 19-20, wherein the antibody is directly labeled.

Clause 22: The method of clause 21, wherein the label is a radioactive marker, a fluorescent marker, an enzyme or a metal.

Clause 23: The method of any one of clauses 3-7 and 10-23, wherein the damage to a reproductive organs comprises endometritis.

Clause 24: The method of any one of claims 1-7 and 10-23, wherein the method determines elevated chlamydial burden in tissue obtained from infection sites.

Clause 25: The method of any one of clauses 1-24, wherein the subject has multiple sexual partners and/or can previously had one or more sexually transmitted disease.

EXAMPLES

Transcriptional profiling of infected women can identify women at higher risk of poor outcomes. Cost savings would be possible through targeted screening and encouragement of future vaccines and interventions with the potential to preserve fertility for those at increased risk for long-term sequelae. The procedure disclosed herein uses an easily obtained blood sample to predict inflammatory responses in the upper genital tract that cannot be evaluated without expensive or invasive procedures requiring a high level of clinical and/or radio-diagnostic intervention.

Example 1

Material and Methods

The ACE Cohort (250 patients) is comprised of women participating in a clinical trial comparing two antibiotic regimens for the treatment of women with clinical pelvic inflammatory disease (PID), defined as sexually active women experiencing pelvic or lower abdominal pain, if no cause for the illness other than PID can be identified, with one or more of the following minimum criteria present on pelvic examination: cervical motion tenderness or uterine or adnexal tenderness. Women of ages 15-40 with clinical PID were enrolled from clinical sites in Pittsburgh, Pa. Upon enrollment, a comprehensive history and physical examination was performed. Vaginal and cervical swab samples were collected for microbiologic testing. Cervicovaginal brush and endometrial biopsy samples were also obtained. Blood was collected and stored for DNA and RNA analyses. Women were assessed for symptomatic and objective evidence of resolution of infection 2-3 days from enrollment. At 4-6 weeks after enrollment, study participants were assessed for clinical cure (improvement or resolution of symptoms and abnormal findings on physical examination) and a repeat endometrial biopsy was performed and submitted for microbiologic testing, histologic analysis and RNA extraction.

The TRAC Cohort (245 patients) is comprised of women of ages 15-30 years at high risk for *C. trachomatis* infection. Criteria indicating high risk status include: ≥3 sexual partners in the previous six months, ≤14 years of age at sexual debut, or history of PID, or presentation to the recruitment site with any of the following: presence of mucopurulent cervicitis on exam, or sexual contact with a partner known to be infected with *C. trachomatis* or *N. gonorrhoeae* or non-gonococcal non-chlamydial urethritis. Participants were enrolled into a longitudinal study to investigate T cell responses important for protection from incident chlamydial infection. Clinical, histological, and microbiological testing was performed at enrollment as described for the ACE cohort, and blood and endometrial samples were obtained for DNA and RNA. Patients in this cohort were also assessed for infection and a blood sample collected at follow-up visits scheduled 1, 4, 8, and 12 months after enrollment. This cohort served as a source of uninfected controls, low disease-risk individuals with chlamydial infection limited to the cervix, and high disease-risk individuals with confirmed ascension of chlamydial infection to the endometrium at enrollment.

Recovery of RNA from Blood Samples and Microarray.

Whole blood samples were collected into TEMPUS™ vacuettes (Life Technologies) and stored at −80° C. Sample processing and microarrays were performed. Total RNA was extracted using TEMPUS™ extraction reagents according to the manufacturer's protocol. Alpha and beta globin mRNA was removed from the specimens using Globinclear (Ambion). Upon completion of the final purification, the RNA quantity and quality was measured by obtaining an A260/A280 nm wavelength ratio and verified via Agilent 2100 bioanalyzer. Samples were subjected to microarray analysis on HumanHT-12 v4 Expression BEADCHIPS® (Illumina).

Histological Assessment of Endometritis.

Endometrial tissue specimens were fixed, sectioned and stained with hematoxylin and eosin. The tissues were evaluated for endometritis according to the criteria of Kiviat et al [Kiviat et al., 1990] with the simultaneous presence of ≥5 neutrophils per 400× field in the endometrial surface epithelium and with one or more plasma cells per 120× field in endometrial stroma defining acute endometritis. The presence of plasma cells alone identified chronic endometritis (Kiviat et al., Am J Surg Pathol. 14, 167-175, 1990). All specimens were independently evaluated by two pathologists who were blinded to experimental design and to the infection status of study participants.

Data Analysis.

The overall strategy used to identify a transcriptional signature that identifies chlamydial PID is outlined in FIG. 1.

Data Quality Control:

Transcripts identified via microarray that were called 'present' in less than 10% of all samples were filtered. The intensity values of remaining data were log 2 transformed. Probes with mean expression values <6.8 and/or standard deviation <0.25 across all samples were removed from further analysis. Quantile normalization was used to normalize the expression levels across all arrays.

Identification of Differentially Expressed (DE) Genes:

To identify genes that were associated with progression to clinical PID due to *C. trachomatis*, the transcriptional profiles of patients with clinical PID who were infected with *Chlamydia*, "cases", were compared to "controls", asymptomatic women with chlamydial infection limited to the cervix without evidence of endometrial infection or histologic endometritis. Moderated t tests were used to discover DE genes between these two groups. P values were adjusted for multiple testing using the Benjamini-Hochberg method. The false discovery rate (FDR) was set at 0.05.

Identification of Optimal Classifiers in Training Set:

Multiple Support Vector Machine Recursive Feature Elimination (mSVM-RFE) was used for feature selection. All DE transcripts were used as starting points for mSVM-RFE. SVM-RFE is an iterative algorithm that works backward from an initial set of features (Guyon et al., *Mach. Learn.* 46, 389-422, 2002). At each round it first fits a simple linear SVM, then ranks the features based on their weights in the SVM solution, finally eliminating the feature with the lowest weight. mSVM-RFE extends this idea by using resampling techniques at each iteration to stabilize the feature rankings (Duan et al., *IEEE trans nanobioscience.* 4, 228-234. 2005). Two fold cross validation was used as the resampling technique. The optimal numbers of features were then selected by estimating generalization error using a varying number of top features.

Internal and External Cross Validation:

For class prediction and validation, SVM was used. The accuracy of classification was estimated using the selected optimal set of features as classifiers by leave one out cross validation in the training dataset (internal validation) and independent testing dataset (external validation). All programming and calculations were conducted in R (version 3.0.1).

Hierarchical Clustering:

Hierarchical clustering was performed to determine if the study participant samples were grouped according to extent of disease and to discover new subgroups in samples. Both genes and samples were clustered in a training dataset. Clustering of genes was based on Pearson correlation of genes, where genes with a similar expression pattern across all samples were grouped together. The dissimilarity between sets of observations was determined by average linkage. Clustering of samples was based on Spearman's rank correlation, and the average linkage criterion was used. In an independent, testing dataset, samples were clustered only and retained the set of genes derived from analysis of the training set and preserved gene order.

Prediction of Probability of Having PID by SVM:

SVM was used to build a statistical model based on our categories of cases and controls in the Training Set. This SVM model mapped the expression of samples as points in space and we used machine learning algorithm to maximally discriminate these two categories. This separation is high dimensional. Then the expression of additional test samples was mapped into the same space to predict the probability of belonging to either class.

Example 2

Results

Clinical Characteristics of Participants:

The mean and standard deviation of age for women participating in this study is 22.0±3.6 years old. Co-infection rates with recognized STI pathogens, *M. genitalium* (MG) or *N. gonorrheoae* (GC) were 18% and 11% respectively. Only 7 out of 146 samples had Hispanic or Latino ethnicity. The percentage of African American women represented in the selected samples was 67%. Table 1 summarizes the distribution of race, age and co-infection in our "cases", women with clinical PID and "controls", asymptomatic women with chlamydial infection limited to the cervix. Neither race nor age was significantly (p>0.05) different between cases and controls in both training and testing datasets.

TABLE 1

Distribution of race, age and STI co-infection between selected 'Cases' and 'Controls' for datasets analyzed.

| Dataset | | Total | Race | | Age (Years) | | Co-infection[‡] | |
|---|---|---|---|---|---|---|---|---|
| | | | Num of AA* | P value | Mean (±SD) | P value | Total | P value |
| Training | case | 10 | 6 (60%) | 0.44 | 21.2 (2.3) | 0.99 | 4 (40%) | 0.72 |
| | control | 27 | 20 (74%) | | 21.2 (3.7) | | 9 (33%) | |
| Testing | case | 5 | 3 (60%) | 0.57 | 26 (3.8) | 0.14 | 3 (60%) | 0.99 |
| | control | 14 | 11 (78%) | | 22.6 (4.9) | | 7 (50%) | |

*Number of African American women participants within groups.
[‡]Co-infections with *M. genitalium* (MG) and/or *N. gonorrheae* (GC) within groups.

Identification of 77 Chlamydial PID Classifiers from 503 Genes that were Differentially Expressed (DE) Between Cases and Controls in Training Dataset.

The Illumina Human HT12 v3.0 expression beadchip microarray employed for this study contained more than 47,000 probes. After statistically filtering low expressed and low variation probes, 4843 genes were retained and were used to identify DE genes between 10 chlamydial PID cases, and 27 controls, asymptomatic patients with cervical infection without endometritis, in a training dataset (Table 2).

TABLE 2

Microbiologic and histologic characteristics of 'Cases' and 'Controls' analyzed in this study.

| Dataset | | Enrollees (N) | Endometrial CT infection | Co-infection | | | Histology | |
|---|---|---|---|---|---|---|---|---|
| | | | | GC | MG | none | Endometritis | Tissue unavailable |
| Training | Cases | 10 | 9 | 2 | 1 | 7 | 7 | 1 |
| | Controls | 27 | 0 | 4 | 5 | 19 | 0 | 21 |
| Testing | Cases | 5 | 3 | 2 | 1 | 3 | 1 | 1 |
| | Controls | 14 | 0 | 1 | 2 | 11 | 0 | 7 |

Using moderated t-test, 503 transcripts were identified with FDR<0.05. Table 3 lists detailed information including gene symbols, fold change, p values and adjusted p values on these 503 transcripts, ordered by fold change from largest to smallest. To discover a minimal set of transcripts within this set of 503 DE genes that could serve as optimal classifiers, mSVM-RFE was used to rank the genes. After estimating generalization error using a varying number of top features, a total of 77 genes were selected (Table 4). For internal validation within this training data set we used leave-one-out cross validation to estimate the accuracy of classification for the 77 transcripts. The average error rate for this resampling algorithm was 0% and the specificity and sensitivity were 100%.

TABLE 3

List of 503 DE genes differentially expressed between women with chlamydial PID and women with asymptomatic cervical infection in Training set.

| Gene Symbol | Adjust. Pvalue* | Fold. Change* | Gene Symbol | Adjust. Pvalue* | Fold. Change* |
|---|---|---|---|---|---|
| LOC100008588 | 0.0086 | 2.9872 | SCO2 | 0.0316 | 1.4595 |
| TNFAIP6 | 0.0113 | 2.4106 | PROS1 | 0.0284 | 1.4565 |
| IFIT1 | 0.0462 | 2.2526 | GSTO1 | 0.0316 | 1.4519 |
| IL1B | 0.0187 | 2.1558 | LOC642678 | 0.0354 | 1.4514 |
| IL1RN | 0.0031 | 2.1353 | MCTP1 | 0.0029 | 1.4443 |
| IFI6 | 0.0223 | 2.1155 | RAB31 | 0.0150 | 1.4319 |
| FCGR1A | 0.0208 | 2.0197 | CECR6 | 0.0193 | 1.4274 |
| MX1 | 0.0270 | 1.8888 | TXN | 0.0469 | 1.4242 |
| EPSTI1 | 0.0265 | 1.8665 | RPS15A | 0.0146 | 1.4239 |
| LY6E | 0.0374 | 1.7685 | HIST1H2BK | 0.0170 | 1.4236 |
| ADM | 0.0374 | 1.7074 | IFNGR2 | 0.0233 | 1.4202 |
| OASL | 0.0450 | 1.7069 | ZNF438 | 0.0170 | 1.4186 |
| FER1L3 | 0.0285 | 1.6504 | IFI35 | 0.0444 | 1.4155 |
| PFKFB3 | 0.0446 | 1.6450 | ZC3H12A | 0.0392 | 1.4137 |
| LILRB4 | 0.0487 | 1.6303 | C1orf85 | 0.0395 | 1.4095 |
| LOC441763 | 0.0146 | 1.6296 | OSM | 0.0466 | 1.4092 |
| LY96 | 0.0146 | 1.6279 | CTNNA1 | 0.0280 | 1.4043 |
| DRAM1 | 0.0481 | 1.6212 | RALB | 0.0364 | 1.3944 |
| SERPING1 | 0.0170 | 1.6081 | RAB32 | 0.0080 | 1.3934 |
| HIST1H4H | 0.0159 | 1.5823 | GSTO1 | 0.0412 | 1.3897 |
| OAS2 | 0.0191 | 1.5628 | SH3GLB1 | 0.0364 | 1.3881 |
| PARP9 | 0.0393 | 1.5472 | GRAMD1A | 0.0465 | 1.3875 |
| SIGLEC5 | 0.0308 | 1.5205 | RRAS | 0.0482 | 1.3870 |
| PNKD | 0.0285 | 1.5174 | TUBA1A | 0.0106 | 1.3863 |
| SOD2 | 0.0315 | 1.5145 | ATP13A1 | 0.0148 | 1.3861 |
| HEBP1 | 0.0165 | 1.5105 | SUMO3 | 0.0316 | 1.3859 |
| SPI1 | 0.0170 | 1.4952 | LOC389386 | 0.0254 | 1.3853 |
| LIMS1 | 0.0302 | 1.4920 | DHX58 | 0.0302 | 1.3843 |
| CA2 | 0.0497 | 1.4872 | GRB2 | 0.0171 | 1.3835 |
| SPATA13 | 0.0354 | 1.4847 | SEMA4A | 0.0323 | 1.3800 |
| ITPRIPL2 | 0.0459 | 1.4811 | ADAP2 | 0.0375 | 1.3788 |
| OSBPL8 | 0.0170 | 1.4794 | PVRL2 | 0.0284 | 1.3783 |
| DAB2 | 0.0302 | 1.4771 | ZYX | 0.0146 | 1.3780 |
| SIRPA | 0.0235 | 1.4757 | NFKBIA | 0.0170 | 1.3763 |
| PARP12 | 0.0207 | 1.4742 | DDX58 | 0.0285 | 1.3737 |
| HP | 0.0285 | 1.4704 | CASP1 | 0.0245 | 1.3715 |
| SIRPA | 0.0469 | 1.4696 | YIPF1 | 0.0208 | 1.3681 |
| GNA15 | 0.0336 | 1.4671 | PSCD4 | 0.0293 | 1.3654 |
| PKM2 | 0.0497 | 1.4619 | FNDC3B | 0.0430 | 1.3633 |
| NFKBIZ | 0.0070 | 1.4617 | LYN | 0.0233 | 1.3622 |
| CUEDC1 | 0.0316 | 1.3610 | ACTR1A | 0.0466 | 1.2789 |
| SAT1 | 0.0375 | 1.3574 | HS.306876 | 0.0469 | 1.2786 |
| ZNFX1 | 0.0114 | 1.3538 | MVP | 0.0285 | 1.2774 |
| LPAR1 | 0.0494 | 1.3507 | MYD88 | 0.0285 | 1.2740 |
| GLRX | 0.0165 | 1.3499 | TATDN3 | 0.0170 | 1.2721 |
| RENBP | 0.0187 | 1.3493 | LAMP3 | 0.0302 | 1.2717 |
| RTP4 | 0.0265 | 1.3465 | TMBIM6 | 0.0274 | 1.2701 |
| NBN | 0.0029 | 1.3438 | SP100 | 0.0492 | 1.2686 |
| FBXO6 | 0.0326 | 1.3419 | LRRC25 | 0.0494 | 1.2662 |
| RRAGD | 0.0293 | 1.3402 | SUPT4H1 | 0.0232 | 1.2659 |
| HIST1H2BK | 0.0317 | 1.3367 | SORT1 | 0.0477 | 1.2630 |
| LAMP2 | 0.0497 | 1.3346 | LOC648729 | 0.0284 | 1.2624 |
| CTSA | 0.0465 | 1.3334 | MCM4 | 0.0393 | 1.2617 |
| NAT8B | 0.0482 | 1.3314 | PTPN12 | 0.0392 | 1.2595 |
| TRIM21 | 0.0300 | 1.3298 | GINS2 | 0.0316 | 1.2576 |
| RHBDF2 | 0.0469 | 1.3296 | LOC653381 | 0.0243 | 1.2543 |
| ACTN1 | 0.0310 | 1.3295 | MTX1 | 0.0470 | 1.2543 |
| TPM4 | 0.0170 | 1.3293 | PHF11 | 0.0364 | 1.2494 |
| TXNRD1 | 0.0233 | 1.3271 | RUFY1 | 0.0446 | 1.2469 |
| ITPRIP | 0.0411 | 1.3269 | MAX | 0.0291 | 1.2465 |
| GALK1 | 0.0239 | 1.3260 | HS. 488254 | 0.0170 | 1.2450 |
| ATP6V0D1 | 0.0233 | 1.3228 | CDCA5 | 0.0460 | 1.2446 |
| MSRA | 0.0315 | 1.3211 | AKIRIN2 | 0.0233 | 1.2443 |
| GBA | 0.0392 | 1.3167 | CDCA7 | 0.0437 | 1.2389 |

TABLE 3-continued

List of 503 DE genes differentially expressed between women with chlamydial PID and women with asymptomatic cervical infection in Training set.

| Gene Symbol | Adjust. Pvalue* | Fold. Change* | Gene Symbol | Adjust. Pvalue* | Fold. Change* |
|---|---|---|---|---|---|
| LOC643384 | 0.0310 | 1.3166 | C10orf105 | 0.0392 | 1.2367 |
| TDRD7 | 0.0316 | 1.3146 | TAGLN2 | 0.0448 | 1.2338 |
| NDUFB3 | 0.0139 | 1.3048 | CKS2 | 0.0274 | 1.2242 |
| FKBP15 | 0.0446 | 1.3047 | FBLN1 | 0.0448 | 1.2227 |
| M6PRBP1 | 0.0426 | 1.3042 | WIPI1 | 0.0475 | 1.2077 |
| TOM1 | 0.0466 | 1.3001 | ZMAT3 | 0.0437 | 0.8272 |
| LOC283547 | 0.0357 | 1.2998 | HS. 4988 | 0.0421 | 0.8262 |
| CD9 | 0.0199 | 1.2985 | LOC400061 | 0.0477 | 0.8201 |
| DYNLT1 | 0.0235 | 1.2970 | FLJ35801 | 0.0389 | 0.8161 |
| MAZ | 0.0430 | 1.2962 | NOP56 | 0.0357 | 0.8077 |
| LOC645159 | 0.0265 | 1.2955 | CIRBP | 0.0430 | 0.8075 |
| RHOG | 0.0170 | 1.2952 | CDK5RAP3 | 0.0376 | 0.8061 |
| ATP9A | 0.0466 | 1.2922 | OCIAD2 | 0.0478 | 0.8015 |
| LOC401152 | 0.0402 | 1.2856 | PLDN | 0.0405 | 0.8007 |
| SPATS2L | 0.0494 | 1.2847 | RPL37A | 0.0354 | 0.7997 |
| AGTRAP | 0.0265 | 1.2841 | LOC729686 | 0.0285 | 0.7985 |
| TRAPPC5 | 0.0466 | 1.2835 | NACA | 0.0462 | 0.7981 |
| LEPROT | 0.0430 | 1.2807 | AASDHPPT | 0.0318 | 0.7976 |
| ACTB | 0.0462 | 1.2796 | LOC727962 | 0.0494 | 0.7972 |
| STXBP2 | 0.0422 | 1.2793 | LOC100127975 | 0.0430 | 0.7963 |
| DDIT3 | 0.0272 | 1.2790 | LOC402694 | 0.0375 | 0.7963 |
| KCNH6 | 0.0494 | 0.7960 | LOC728734 | 0.0451 | 0.7614 |
| HS.552082 | 0.0212 | 0.7904 | ZNF430 | 0.0393 | 0.7611 |
| RNASEH2B | 0.0494 | 0.7898 | LOC100131261 | 0.0373 | 0.7599 |
| EIF2S3 | 0.0290 | 0.7891 | HSPE1 | 0.0470 | 0.7597 |
| LOC100128056 | 0.0302 | 0.7860 | CMPK1 | 0.0421 | 0.7587 |
| RPL7L1 | 0.0354 | 0.7858 | CREB1 | 0.0374 | 0.7578 |
| FYTTD1 | 0.0272 | 0.7850 | STAG3L2 | 0.0293 | 0.7575 |
| SH3YL1 | 0.0148 | 0.7846 | SNURF | 0.0460 | 0.7573 |
| P2RY10 | 0.0232 | 0.7837 | SULT1A2 | 0.0272 | 0.7573 |
| EXOSC10 | 0.0170 | 0.7828 | TMEM106A | 0.0389 | 0.7569 |
| MYBL1 | 0.0302 | 0.7827 | PNPT1 | 0.0460 | 0.7566 |
| HNRPH1 | 0.0494 | 0.7818 | PDCD4 | 0.0494 | 0.7557 |
| OSBPL10 | 0.0392 | 0.7813 | LOC644745 | 0.0219 | 0.7553 |
| CAST | 0.0364 | 0.7812 | LOC644937 | 0.0364 | 0.7545 |
| LOC730004 | 0.0206 | 0.7811 | LOC390183 | 0.0346 | 0.7544 |
| HNRPDL | 0.0247 | 0.7793 | MYC | 0.0326 | 0.7543 |
| BUB3 | 0.0232 | 0.7781 | LOC391019 | 0.0326 | 0.7543 |
| SP4 | 0.0293 | 0.7780 | LOC391126 | 0.0392 | 0.7540 |
| RPL7A | 0.0305 | 0.7774 | GIMAP7 | 0.0494 | 0.7536 |
| POLR2J3 | 0.0316 | 0.7755 | RPS2 | 0.0272 | 0.7530 |
| ZNF791 | 0.0293 | 0.7754 | WASPIP | 0.0305 | 0.7511 |
| P2RY10 | 0.0466 | 0.7747 | LOC729500 | 0.0302 | 0.7508 |
| LOC653702 | 0.0175 | 0.7746 | RBM34 | 0.0175 | 0.7499 |
| BCL11A | 0.0243 | 0.7736 | SBDS | 0.0175 | 0.7493 |
| LOC401676 | 0.0186 | 0.7726 | VPS41 | 0.0385 | 0.7489 |
| LOC644739 | 0.0450 | 0.7707 | CDAN1 | 0.0334 | 0.7488 |
| PTPLB | 0.0316 | 0.7705 | RPL35 | 0.0187 | 0.7488 |
| LOC646483 | 0.0285 | 0.7695 | LOC285053 | 0.0161 | 0.7481 |
| NFATC2IP | 0.0240 | 0.7679 | ZNF652 | 0.0232 | 0.7475 |
| LOC728026 | 0.0466 | 0.7670 | SACM1L | 0.0302 | 0.7454 |
| RPLP0 | 0.0274 | 0.7665 | CCM2 | 0.0357 | 0.7453 |
| TNFAIP8 | 0.0293 | 0.7657 | HS. 276860 | 0.0428 | 0.7450 |
| AFF3 | 0.0271 | 0.7650 | ZNF786 | 0.0394 | 0.7448 |
| LOC100130562 | 0.0285 | 0.7644 | LOC100132795 | 0.0405 | 0.7435 |
| JAK1 | 0.0285 | 0.7640 | LOC100131866 | 0.0276 | 0.7428 |
| BCL11A | 0.0186 | 0.7638 | TSPYL1 | 0.0208 | 0.7418 |
| CMPK1 | 0.0357 | 0.7638 | RPL14L | 0.0373 | 0.7416 |
| C10orf104 | 0.0146 | 0.7635 | FAM116A | 0.0108 | 0.7404 |
| LOC284821 | 0.0285 | 0.7631 | SULT1A1 | 0.0171 | 0.7401 |
| PPCS | 0.0315 | 0.7628 | GZMM | 0.0465 | 0.7400 |
| PEBP1 | 0.0469 | 0.7621 | RBM3 | 0.0134 | 0.7398 |
| DENR | 0.0494 | 0.7620 | LOC728843 | 0.0203 | 0.7387 |
| HNRPDL | 0.0226 | 0.7620 | DDX51 | 0.0285 | 0.7386 |
| MEF2D | 0.0108 | 0.7619 | HINT3 | 0.0046 | 0.7379 |
| AIRE | 0.0460 | 0.7615 | CCDC125 | 0.0405 | 0.7368 |
| LOC649821 | 0.0363 | 0.7366 | IL17RD | 0.0310 | 0.7104 |
| SYNE2 | 0.0316 | 0.7359 | LOC653314 | 0.0243 | 0.7098 |
| LOC100129237 | 0.0170 | 0.7358 | RASGRP1 | 0.0146 | 0.7097 |
| LOC440311 | 0.0199 | 0.7356 | LOC648921 | 0.0362 | 0.7096 |
| LOC643310 | 0.0485 | 0.7344 | LOC646996 | 0.0165 | 0.7086 |
| C9orf80 | 0.0233 | 0.7342 | CAST | 0.0384 | 0.7084 |
| PYHIN1 | 0.0459 | 0.7340 | LOC729236 | 0.0254 | 0.7083 |
| SDHALP1 | 0.0402 | 0.7339 | CD79B | 0.0394 | 0.7078 |

TABLE 3-continued

List of 503 DE genes differentially expressed between women with chlamydial PID and women with asymptomatic cervical infection in Training set.

| Gene Symbol | Adjust. Pvalue* | Fold. Change* | Gene Symbol | Adjust. Pvalue* | Fold. Change* |
|---|---|---|---|---|---|
| SNRPN | 0.0187 | 0.7336 | ANKRD30B | 0.0402 | 0.7074 |
| TMED10 | 0.0176 | 0.7314 | PIP5K2B | 0.0290 | 0.7066 |
| DEM1 | 0.0450 | 0.7299 | MCART1 | 0.0219 | 0.7060 |
| DUXAP3 | 0.0316 | 0.7294 | RPL14L | 0.0285 | 0.7053 |
| CERK | 0.0105 | 0.7287 | ZNF486 | 0.0356 | 0.7048 |
| LOC389322 | 0.0465 | 0.7284 | OCIAD1 | 0.0171 | 0.7042 |
| LDHB | 0.0385 | 0.7280 | GIMAP2 | 0.0285 | 0.7042 |
| CROP | 0.0285 | 0.7278 | TARP | 0.0375 | 0.7034 |
| MGC87895 | 0.0465 | 0.7271 | LOC441743 | 0.0247 | 0.7029 |
| LOC388344 | 0.0193 | 0.7267 | GRAP | 0.0497 | 0.7020 |
| FAM73A | 0.0301 | 0.7265 | DTWD2 | 0.0385 | 0.7016 |
| LEP | 0.0494 | 0.7263 | LOC729926 | 0.0357 | 0.7014 |
| PLEKHA1 | 0.0120 | 0.7263 | LOC100130053 | 0.0262 | 0.7013 |
| PYHIN1 | 0.0354 | 0.7242 | ALPP | 0.0316 | 0.7012 |
| EIF3M | 0.0460 | 0.7240 | LOC100134053 | 0.0316 | 0.7006 |
| LBH | 0.0146 | 0.7234 | LOC285741 | 0.0274 | 0.7004 |
| HECA | 0.0250 | 0.7233 | LOC100129211 | 0.0256 | 0.6992 |
| CATSPER2 | 0.0194 | 0.7230 | LOC728903 | 0.0275 | 0.6986 |
| LOC647436 | 0.0170 | 0.7225 | LOC441506 | 0.0316 | 0.6975 |
| HSD17B7 | 0.0219 | 0.7224 | LOC100132992 | 0.0233 | 0.6967 |
| ZNF14 | 0.0384 | 0.7223 | LOC202781 | 0.0243 | 0.6962 |
| NACAP1 | 0.0316 | 0.7217 | ATM | 0.0175 | 0.6956 |
| CDC42 | 0.0255 | 0.7194 | LOC647285 | 0.0170 | 0.6956 |
| LOC644907 | 0.0285 | 0.7189 | LOC645452 | 0.0357 | 0.6944 |
| LOC100129502 | 0.0331 | 0.7176 | LOC100132658 | 0.0062 | 0.6933 |
| CCBE1 | 0.0485 | 0.7164 | RELL1 | 0.0316 | 0.6933 |
| FCRLA | 0.0392 | 0.7162 | CDC42SE2 | 0.0170 | 0.6929 |
| LCOR | 0.0175 | 0.7156 | LOC338870 | 0.0481 | 0.6928 |
| LOC729423 | 0.0175 | 0.7152 | FLJ44124 | 0.0170 | 0.6907 |
| NUBPL | 0.0470 | 0.7151 | FCRL3 | 0.0393 | 0.6888 |
| LOC388556 | 0.0108 | 0.7148 | LOC399804 | 0.0113 | 0.6883 |
| LOC100133772 | 0.0170 | 0.7147 | LOC653086 | 0.0300 | 0.6878 |
| FLJ35390 | 0.0409 | 0.7138 | KCTD12 | 0.0485 | 0.6871 |
| LOC731985 | 0.0223 | 0.7137 | FLJ36131 | 0.0384 | 0.6867 |
| SULT1A4 | 0.0176 | 0.7117 | PPA2 | 0.0138 | 0.6858 |
| LOC388532 | 0.0469 | 0.7116 | EDG1 | 0.0146 | 0.6851 |
| C2orf69 | 0.0242 | 0.7115 | C8orf45 | 0.0232 | 0.6848 |
| SLC35E1 | 0.0165 | 0.6843 | PTMA | 0.0293 | 0.6624 |
| LOC731640 | 0.0364 | 0.6842 | LOC100128098 | 0.0264 | 0.6623 |
| LOC255167 | 0.0428 | 0.6830 | S1PR1 | 0.0146 | 0.6612 |
| BCL2 | 0.0384 | 0.6826 | LOC645436 | 0.0146 | 0.6608 |
| LOC100134648 | 0.0274 | 0.6825 | RASGRP2 | 0.0475 | 0.6604 |
| GIMAP1 | 0.0181 | 0.6815 | LOC643949 | 0.0175 | 0.6604 |
| LOC100132585 | 0.0349 | 0.6813 | LOC100131787 | 0.0146 | 0.6593 |
| LOC90925 | 0.0176 | 0.6810 | IFP38 | 0.0170 | 0.6593 |
| LOC100131196 | 0.0120 | 0.6802 | LOC390354 | 0.0170 | 0.6592 |
| USP49 | 0.0207 | 0.6786 | SULT1A1 | 0.0029 | 0.6588 |
| BCL2 | 0.0146 | 0.6784 | LOC100131572 | 0.0170 | 0.6587 |
| LOC729102 | 0.0232 | 0.6782 | LOC100131989 | 0.0208 | 0.6581 |
| LOC100132727 | 0.0175 | 0.6776 | LOC647030 | 0.0170 | 0.6559 |
| LOC642934 | 0.0293 | 0.6770 | LOC728820 | 0.0105 | 0.6556 |
| LOC645173 | 0.0316 | 0.6770 | SP4 | 0.0046 | 0.6549 |
| CCR6 | 0.0130 | 0.6769 | CRCP | 0.0145 | 0.6543 |
| LOC90586 | 0.0203 | 0.6766 | LOC645715 | 0.0120 | 0.6535 |
| ZNF682 | 0.0130 | 0.6755 | LOC645157 | 0.0394 | 0.6525 |
| DMC1 | 0.0289 | 0.6745 | PNPT1 | 0.0170 | 0.6515 |
| LOC100131866 | 0.0107 | 0.6734 | LOC730029 | 0.0308 | 0.6514 |
| LOC648210 | 0.0105 | 0.6733 | RPL13 | 0.0049 | 0.6509 |
| LOC388621 | 0.0302 | 0.6730 | LOC100133372 | 0.0029 | 0.6505 |
| LOC100133583 | 0.0477 | 0.6729 | LOC728732 | 0.0175 | 0.6487 |
| LOC728481 | 0.0175 | 0.6721 | LOC728484 | 0.0051 | 0.6483 |
| ID2 | 0.0175 | 0.6718 | LOC100131718 | 0.0302 | 0.6465 |
| LOC387825 | 0.0275 | 0.6714 | LOC100128062 | 0.0255 | 0.6450 |
| LOC653820 | 0.0250 | 0.6708 | RPS6P1 | 0.0108 | 0.6443 |
| CXCR5 | 0.0385 | 0.6707 | LOC100130892 | 0.0146 | 0.6428 |
| LOC728553 | 0.0093 | 0.6707 | LOC730990 | 0.0235 | 0.6425 |
| LOC642817 | 0.0108 | 0.6706 | LOC388076 | 0.0185 | 0.6394 |
| LOC389787 | 0.0357 | 0.6700 | VPREB3 | 0.0195 | 0.6393 |
| CD79B | 0.0170 | 0.6698 | LOC645385 | 0.0062 | 0.6390 |
| LOC440927 | 0.0049 | 0.6697 | BLZF1 | 0.0162 | 0.6382 |
| LOC390345 | 0.0247 | 0.6693 | HNRPA1P4 | 0.0106 | 0.6380 |
| RPL13L | 0.0219 | 0.6693 | LOC646785 | 0.0082 | 0.6375 |
| SPTLC1 | 0.0145 | 0.6692 | EEF1AL7 | 0.0040 | 0.6371 |
| LOC653489 | 0.0359 | 0.6674 | DDX17 | 0.0232 | 0.6350 |

TABLE 3-continued

List of 503 DE genes differentially expressed between women with chlamydial PID and women with asymptomatic cervical infection in Training set.

| Gene Symbol | Adjust. Pvalue* | Fold. Change* | Gene Symbol | Adjust. Pvalue* | Fold. Change* |
|---|---|---|---|---|---|
| SUMO2 | 0.0316 | 0.6662 | LOC100129742 | 0.0310 | 0.6350 |
| CD19 | 0.0215 | 0.6661 | LOC643873 | 0.0106 | 0.6345 |
| LOC728060 | 0.0274 | 0.6661 | CDKN1B | 0.0285 | 0.6339 |
| LOC728060 | 0.0170 | 0.6658 | LOC730288 | 0.0041 | 0.6336 |
| LOC727865 | 0.0208 | 0.6636 | LOC100128410 | 0.0108 | 0.6320 |
| LOC645138 | 0.0148 | 0.6628 | LOC391833 | 0.0207 | 0.6318 |
| LOC91561 | 0.0131 | 0.6627 | KLRD1 | 0.0285 | 0.6293 |
| LOC648622 | 0.0086 | 0.6290 | LOC728672 | 0.0062 | 0.5814 |
| LOC388654 | 0.0170 | 0.6276 | LOC649946 | 0.0092 | 0.5799 |
| LOC100134159 | 0.0146 | 0.6270 | LOC148430 | 0.0145 | 0.5789 |
| LOC729340 | 0.0130 | 0.6268 | LOC653658 | 0.0106 | 0.5774 |
| LOC646688 | 0.0106 | 0.6225 | CD79A | 0.0396 | 0.5757 |
| ZNF738 | 0.0146 | 0.6225 | LOC651202 | 0.0170 | 0.5717 |
| RPS27 | 0.0091 | 0.6207 | LOC728643 | 0.0014 | 0.5710 |
| CD79B | 0.0305 | 0.6202 | RPL23 | 0.0030 | 0.5704 |
| LOC728973 | 0.0115 | 0.6175 | LOC100130070 | 0.0092 | 0.5688 |
| LOC645691 | 0.0193 | 0.6156 | LOC651149 | 0.0080 | 0.5686 |
| LOC648210 | 0.0146 | 0.6147 | RPLP1 | 0.0049 | 0.5628 |
| NLRP8 | 0.0108 | 0.6132 | LOC220433 | 0.0053 | 0.5622 |
| LOC100131905 | 0.0161 | 0.6117 | RPL7 | 0.0051 | 0.5589 |
| LOC728820 | 0.0080 | 0.6089 | LOC100132528 | 0.0014 | 0.5565 |
| RASGRP2 | 0.0146 | 0.6081 | HNRPA1L-2 | 0.0019 | 0.5560 |
| LOC341315 | 0.0146 | 0.6081 | LOC100129657 | 0.0145 | 0.5489 |
| LOC728590 | 0.0430 | 0.6073 | LOC648210 | 0.0029 | 0.5475 |
| LOC730255 | 0.0106 | 0.6044 | RPL14 | 0.0106 | 0.5433 |
| LOC642989 | 0.0208 | 0.6038 | TCL1A | 0.0014 | 0.5339 |
| LOC158345 | 0.0049 | 0.6032 | FLJ43681 | 0.0120 | 0.5322 |
| SNHG7 | 0.0142 | 0.6027 | LOC642828 | 0.0203 | 0.5281 |
| LOC727984 | 0.0057 | 0.6019 | LOC100134504 | 0.0029 | 0.5275 |
| LOC728590 | 0.0029 | 0.6018 | FBXO7 | 0.0175 | 0.5154 |
| LOC653773 | 0.0108 | 0.6005 | LOC100132291 | 0.0032 | 0.5132 |
| LOC402112 | 0.0014 | 0.5997 | RPS28 | 0.0051 | 0.5116 |
| LOC646688 | 0.0049 | 0.5972 | LOC286444 | 0.0146 | 0.5094 |
| RPL9 | 0.0187 | 0.5919 | ETS1 | 0.0120 | 0.4995 |
| LOC100131609 | 0.0029 | 0.5905 | LOC402251 | 0.0001 | 0.4957 |
| C5orf28 | 0.0106 | 0.5896 | SLC4A1 | 0.0288 | 0.4938 |
| LOC100130562 | 0.0065 | 0.5864 | LOC100132673 | 0.0082 | 0.4734 |
| LOC100131609 | 0.0029 | 0.5859 | LOC100129028 | 0.0029 | 0.4537 |
| LOC100128936 | 0.0019 | 0.5851 | MYOM2 | 0.0378 | 0.4305 |
| LOC653232 | 0.0113 | 0.5845 | | | |

*P values and Fold Change rounded to 4 decimal places.

TABLE 4

List of 77 optimal classifiers of chlamydial PID derived from 503 DE genes via SVM-RFE algorithm

| gene_symbol | adjust. pvalue | pvalue | fold. change | CYTOBAND |
|---|---|---|---|---|
| TCL1A | 0.00141 | 1.46E-06 | 0.533888 | 14q32.13b |
| HINT3 | 0.004615 | 2.20E-05 | 0.737912 | 6q22.32a |
| LOC100008588 | 0.008563 | 8.13E-05 | 2.987179 | |
| CDK5RAP3 | 0.037587 | 0.002965 | 0.806075 | 17q21.32b |
| CDCA7 | 0.043731 | 0.003892 | 1.238948 | 2q31.1e |
| FLJ35801 | 0.038881 | 0.003148 | 0.816076 | 22q12.2c |
| TATDN3 | 0.01699 | 0.000503 | 1.272091 | 1q32.3c |
| LOC648729 | 0.028438 | 0.001562 | 1.262351 | 8p12e |
| VPREB3 | 0.019499 | 0.000733 | 0.639321 | 22q11.23a |
| HIST1H4H | 0.015898 | 0.000381 | 1.582308 | 6p22.1d |
| MCM4 | 0.039332 | 0.003274 | 1.261673 | 8q11.21b |
| SULT1A1 | 0.002882 | 7.22E-06 | 0.658823 | 16p11.2e |
| LOC642678 | 0.035437 | 0.002592 | 1.451406 | 2p11.1d |
| FCRLA | 0.03918 | 0.003198 | 0.71618 | 1q23.3b |
| RPS15A | 0.014557 | 0.000299 | 1.42391 | 16p12.3b |
| LOC100130562 | 0.006455 | 5.07E-05 | 0.586418 | 12q24.23a |
| CKS2 | 0.02742 | 0.001466 | 1.224172 | 9q22.2a |
| LIMS1 | 0.030177 | 0.001899 | 1.491971 | 2q12.3c-q13a |
| OSBPL8 | 0.01699 | 0.000519 | 1.479427 | 12q21.2a |
| GRB2 | 0.017078 | 0.000532 | 1.383546 | 17q25.1c |
| SULT1A2 | 0.027223 | 0.001421 | 0.75727 | 16p11.2e |
| LOC441763 | 0.014569 | 0.000307 | 1.629603 | |
| SLC4A1 | 0.028779 | 0.001694 | 0.493817 | 17q21.31c |
| LOC90925 | 0.017628 | 0.000604 | 0.681048 | |
| SPATA13 | 0.035437 | 0.002594 | 1.484737 | 13q12.12b |
| TPM4 | 0.01699 | 0.000486 | 1.329267 | 19p13.12a |
| MYOM2 | 0.03779 | 0.002989 | 0.430463 | 8p23.3a |
| MCTP1 | 0.002882 | 7.90E-06 | 1.444266 | 5q15c |
| SUMO3 | 0.031648 | 0.00221 | 1.385856 | 21q22.3d |
| CD19 | 0.021543 | 0.000885 | 0.666118 | 16p11.2e |
| LOC132727 | 0.01748 | 0.000565 | 0.677568 | 15q11.2a |
| GINS2 | 0.031648 | 0.002208 | 1.257559 | 16q24.1b |
| C10orf105 | 0.039183 | 0.003236 | 1.236658 | 10q22.1d |
| PPA2 | 0.013842 | 0.000246 | 0.685848 | 4q24d |
| LOC100133372 | 0.002882 | 9.29E-06 | 0.650468 | |
| LEPROT | 0.042955 | 0.003798 | 1.280661 | 1p31.3b |
| CDC42 | 0.025512 | 0.001264 | 0.719356 | 1p36.12a |
| NAT8B | 0.04818 | 0.004805 | 1.331352 | 2p13.2a |
| MSRA | 0.031535 | 0.002097 | 1.321064 | 8p23.1c |
| CD79B | 0.01699 | 0.000509 | 0.669781 | 17q23.3b |
| MAX | 0.029134 | 0.001739 | 1.246549 | 14q23.3a |
| PROS1 | 0.028438 | 0.001562 | 1.456486 | 3q11.2a |

TABLE 4-continued

List of 77 optimal classifiers of chlamydial PID
derived from 503 DE genes via SVM-RFE algorithm

| gene_symbol | adjust. pvalue | pvalue | fold. change | CYTOBAND |
|---|---|---|---|---|
| CCR6 | 0.01304 | 0.000222 | 0.676927 | 6q27c |
| FBXO7 | 0.01748 | 0.000553 | 0.515381 | 22q12.3a |
| SULT1A4 | 0.017628 | 0.000603 | 0.711744 | 16p11.2d |
| LOC642934 | 0.029316 | 0.001773 | 0.677049 | 10q23.1c |
| LOC100129237 | 0.01699 | 0.000455 | 0.735832 | 8q12.1b |
| LOC645159 | 0.026464 | 0.00135 | 1.295461 | 1q21.1e |
| LOC644739 | 0.045026 | 0.0041 | 0.770681 | Xp11.23f |
| RPL13 | 0.004896 | 2.58E-05 | 0.650902 | 16q24.3b |
| LOC643873 | 0.010558 | 0.000125 | 0.634471 | Xq23a |
| LOC286444 | 0.014569 | 0.00033 | 0.509379 | Xp11.4b |
| C10orf104 | 0.014569 | 0.000329 | 0.763498 | 10q22.1e-q22.1f |
| LOC100133583 | 0.047681 | 0.004706 | 0.672867 | |
| MYD88 | 0.028475 | 0.001642 | 1.274019 | 3p22.2a |
| LOC100129742 | 0.031024 | 0.002043 | 0.634978 | 2q24.2a |
| RPL37A | 0.035437 | 0.002585 | 0.799735 | 2q35c |
| JAK1 | 0.028475 | 0.001631 | 0.764033 | 1p31.3b |
| PARP12 | 0.020732 | 0.000818 | 1.4742 | 7q34c |
| SDHALP1 | 0.040202 | 0.00342 | 0.733872 | 3q29f |
| CERK | 0.010516 | 0.000115 | 0.728713 | 22q13.31d |
| CMPK1 | 0.042058 | 0.003645 | 0.758726 | 1p33d |
| NFKBIZ | 0.007 | 5.64E-05 | 1.461664 | 3q12.3a |
| LY6E | 0.037448 | 0.002905 | 1.768509 | 8q24.3f |
| C5orf28 | 0.01063 | 0.000134 | 0.589604 | 5p12c |
| LOC402251 | 9.92E-05 | 2.05E-08 | 0.49572 | |
| LOC642989 | 0.02076 | 0.000827 | 0.603774 | |
| HEBP1 | 0.016547 | 0.000418 | 1.510498 | 12p13.1b |
| MEF2D | 0.01076 | 0.000148 | 0.76193 | 1q22d |
| LOC100130053 | 0.026212 | 0.00131 | 0.701257 | 10p13c |
| RTP4 | 0.026464 | 0.001348 | 1.34651 | 3q27.3b |
| KCNH6 | 0.049371 | 0.005086 | 0.79598 | 17q23.3a |
| FBLN1 | 0.044839 | 0.004055 | 1.222655 | 22q13.31c |
| BCL11A | 0.024336 | 0.001148 | 0.773627 | 2p16.1a |
| SERPING1 | 0.01699 | 0.0005 | 1.608092 | 11q12.1a |
| AKIRIN2 | 0.023268 | 0.001033 | 1.244339 | 6q15b |
| CDCA5 | 0.046018 | 0.004263 | 1.244602 | 11q13.1c |

To determine if the samples grouped according to extent of disease, hierarchical clustering (both samples and genes) was performed using this Training dataset. Within this set, the transcriptional profiles from eight of the ten subjects with chlamydial PID were tightly clustered, indicating that 503 DE genes could identify the majority of women with chlamydial PID.

Additionally, it was observed that some cervically-infected women also clustered with this group, suggesting that this gene set also identified asymptomatic subjects displaying responses associated with disease. Using only the 77 classifier transcripts, all 10 chlamydial PID patients formed a single, distinct cluster. This indicated that a signature using these 77 classifiers performed better than one incorporating all 503 DE genes.

Validation of 77 Classifier Genes in an Independent Test Set.

The strength of these classifiers was further evaluated using an independent Test set of samples drawn from the same cohorts (5 cases and 14 controls). The Table below shows all 503 DE genes. Profiles from 4 out of 5 subjects with chlamydial PID tightly clustered. Sample clustering of the Testing data set using 77 classifier transcripts again more effectively grouped subjects with chlamydial PID with all 5 cases tightly clustered. The accuracy of classification was estimated using leave-one-out cross-validation for the 77 optimal classifier genes and the sensitivity and specificity were 100% with zero average error rates for this set, confirming the utility of these classifiers for a chlamydial PID signature.

Investigation of Chlamydial PID Signature Specificity.

Clinical PID can be caused by sexually transmitted pathogens other than C. trachomatis such as Mycoplasma genitalium and N. gonorrhoeae. Gardnerella vaginalis, Atopobium sp and other anaerobes have also been implicated as causing PID and histologic endometritis (reviewed by Judlin, Curr Opin Infect Dis. 23, 83-7, 2010). It was first sought to explore whether the chlamydial PID signature could distinguish patients with chlamydial PID from those with PID due to M. genitalium (N=9). It was found that the chlamydial PID signature was pathogen-specific. Patients with MG PID formed a distinct cluster independent of the patients with chlamydial PID. This suggests that similar approaches could be used to define a MG PID signature. Additionally, in several subjects an infectious cause for their PID symptoms was not identified (N=30). It was determined if the chlamydial PID signature of 77 classifiers distinguished these patients from those with CT PID. Indeed, patients with clinical PID but without an STI clustered separately from the patients with CT PID. As previously observed with the Training set, some asymptomatic subjects with cervical CT infection nevertheless clustered with chlamydial PID. As a final control, an additional group comprised of asymptomatic, uninfected subjects (N=25) was examined. The patients with CT PID remained tightly clustered, whereas subjects with cervical CT infection were indistinguishable from uninfected subjects with respect to genes within the PID signature.

Prediction of Elevated Risk for Upper Reproductive Tract Disease after Asymptomatic C. trachomatis Infection.

Figure 2:
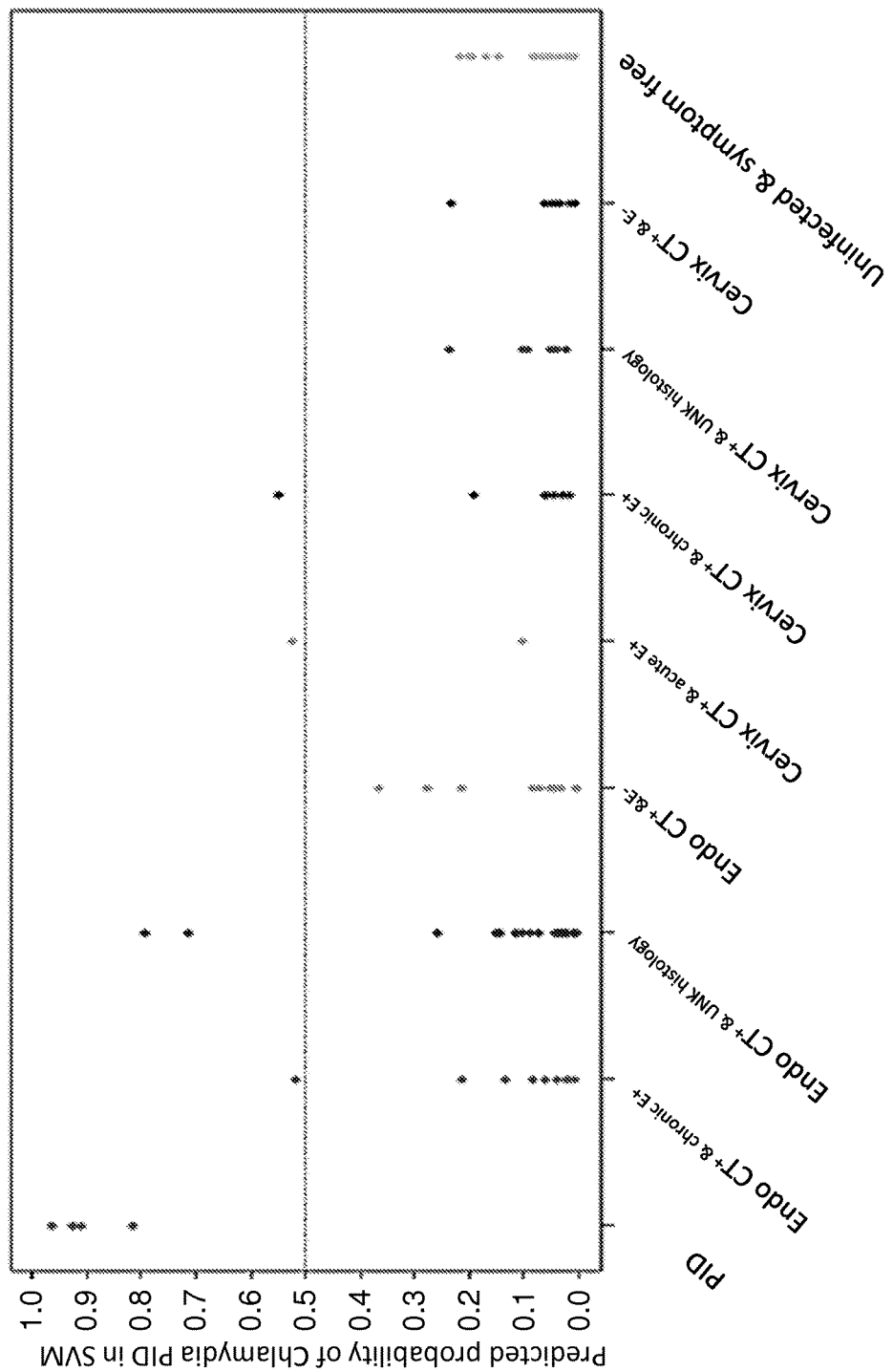
FIG. 2. Predicted probability of *chlamydia* PID using SVM in asymptomatic women with CT infection. Study participants are assorted into groups reflecting potential risk factors for disease including; Endo CT+: endometrial chlamydial infection, and the presence of histologically confirmed endometritis (E+). Groups of participants lacking recognized risk factors because CT infection was limited to the cervix (Cervical CT+) or who did not have endometritis (E−) are also included. Study participants with insufficient tissue for histologic diagnosis are designated as UNK.

It is already recognized that women who develop clinical PID caused by C. trachomatis are at risk for long term reproductive morbidities. Chlamydia trachomatis genital infection can be easily detected via commercial nucleic acid amplification tests, and effective antibiotic treatment is available once infection is diagnosed. However, the majority of women are asymptomatically infected and consequently fail to seek treatment. These women may have subclinical inflammation of the upper genital which lead to the same reproductive morbidities known to occur with clinical PID (Wiesenfeld et al, Obstet Gynecol 120, 37-43, 2012). Consequently, SVM was used to develop a predictive algorithm based on the 77 classifiers of chlamydial PID to see if subjects with chlamydial infection could be placed in high and low risk groups. As shown in FIG. 2, the predicted probability of belonging to the chlamydial PID group for all 5 test cases based on the Training set-derived data was >0.8, while all controls had a predicted probability of <0.25 of belonging to this group. Five out of 90 (5.6%) asymptomatic women with chlamydial infection were predicted to have a high probability of chlamydial PID by SVM. High-risk women have been determined to progress to clinical PID at a rate of ~3-5% within two weeks of infection diagnosis in the absence of treatment (Geisler et al., J Infect Dis. 201 Suppl 2, S104-13, 2010). Thus, the rate in the test group agrees with clinical data. Likely risk factors for disease include endometrial infection and genetic predisposition to a heightened inflammatory response. Of the women predicted to have high-risk for PID, three had endometritis and two with unknown histology had confirmed endometrial infection.

Example 3

Strategy for the Selection of the Minimal Set of 34 Classifiers in Training Set

Multiple Support Vector Machine Recursive Feature Elimination (mSVM-RFE) (Duan et al., IEEE trans nanobioscience. 4, 228-234. 2005) was used for feature selection. All DE transcripts from above step were used as starting point for mSVM-RFE. SVM-RFE (Guyon et al., 2002, *Machine Learning* 46: 389-422) is an iterative algorithm that works backward from an initial set of features. At each round it first fits a simple linear SVM, then ranks the features based on their weights in the SVM solution, and finally eliminates the feature with the lowest weight. mSVM-RFE extends this idea by using resampling techniques at each iteration to stabilize the feature rankings. Here we use two fold cross validation.

The optimal numbers of features were then selected by estimating generalization error using a varying number of top features.

The minimal number of classifiers with estimated generalization error ≤0.05 in training data using mSVM-RFE is 34. Leave one out cross-validation showed the average error rate in independent testing dataset is zero with 100% sensitivity and specificity using these 34 classifiers.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of treating a human subject with chlamydial pelvic inflammatory disease, comprising:
    performing one or more assays that detect a level of T cell leukemia/lymphoma 1A(TCL1A), histidine triad nucleotide binding protein 3 (HINT3), CDK5 regulatory subunit associated protein 3 (CDK5RAP3), *Homo sapiens* chromosome 22 open reading frame 27 (FLJ35801), pre-B lymphocyte gene 3 (VPREB3), *sapiens* sulfotransferase family cytosolic 1A phenol-preferring member 1 (SULT1A1) (transcript variant 5), SULT1A1 (transcript variant 3), Fc receptor like A (FCRLA), LOC100130562, sulfotransferase family cytosolic 1A phenol-preferring member 2 (SULT1A2), solute carrier family 4 anion exchanger member 1 (SLC4A1), LOC90925, myomesin 2 (MYOM2), CD19 molecule (CD19), LOC100132727, LOC100008588, cell division cycle associated 7 (CDCA7), TatD DNase domain containing 3 (TATDN3), LOC648729, histone cluster 1 H4 family member h (HIST1H4H), minichromosome maintenance complex component 4 (MCM4), LOC642678, ribosomal protein S15a (RPS15A), CDC28 protein kinase regulatory subunit 2 (CKS2), LIM and senescent cell antigen-like domains 1 (LIMS1), oxysterol binding protein like 8 (OSBPL8), growth factor receptor-bound protein 2 (GRB2), LOC441763, spermatogenesis associated 13 (SPATA13), tropomyosin 4 (TPM4), multiple C2 domains transmembrane 1 (MCTP1), and small ubiquitin-like modifier 3 (SUMO3) mRNA in a blood sample from the subject; and
    comparing the level of TCL1A, HINT3, CDK5RAP3, FLJ35801, VPREB3, SULT1A1 (transcript variant 5), SULT1A1 (transcript variant 3), FCRLA, LOC100130562, SULT1A2, SLC4A1, LOC90925, MYOM2, CD19, LOC100132727, LOC100008588, CDCA7, TATDN3, LOC648729, HIST1H4H, MCM4, LOC642678, RPS15A, CKS2, LIMS1, OSBPL8, GRB2, LOC441763, SPATA13, TPM4, MCTP1, SUMO3 mRNA to a respective control level of TCL1A, HINT3, CDK5RAP3, FLJ35801, VPREB3, SULT1A1 (transcript variant 5), SULT1A1 (transcript variant 3), FCRLA, LOC100130562, SULT1A2, SLC4A1, LOC90925, MYOM2, CD19, LOC100132727, LOC100008588, CDCA7, TATDN3, LOC648729, HIST1H4H, MCM4, LOC642678, RPS15A, CKS2, LIMS1, OSBPL8, GRB2, LOC441763, SPATA13, TPM4, MCTP1, and SUMO3 mRNA, respectively;
    detecting a decrease in the level of TCL1A, HINT3, CDK5RAP3, FLJ35801, VPREB3, SULT1A1 (transcript variant 5), SULT1A1 (transcript variant 3), FCRLA, LOC100130562, SULT1A2, SLC4A1, LOC90925, MYOM2, CD19, LOC100132727 mRNA, and an increase in the level of LOC100008588, CDCA7, TATDN3, LOC648729, HIST1H4H, MCM4, LOC642678, RPS15A, CKS2, LIMS1, OSBPL8, GRB2, LOC441763, SPATA13, TPM4, MCTP1, and SUMO3 mRNA, and
    administering to the human subject an effective amount of azithromycin, doxycycline, erythromycin, amoxicillin or ofloxacin, thereby treating the chlamydial pelvic inflammatory disease in the human subject.

2. The method of claim 1, comprising contacting the blood sample with a microarray.

3. The method of claim 1, further comprising:
    performing one or more assays that detect a level of MYOM2, SLC4A1, LOC402251, LOC286444, F-box protein 7 (FBXO7), TCL1A, LOC100130562, *Homo sapiens* chromosome 5 open reading frame 28 (C5orf28), LOC642989, CD79B antigen (immunoglobulin-associated beta) (CD79B), LOC643873, LOC100129742, VPREB3, LOC100133372, ribosomal protein L13 (RPL13), SULT1A1 (transcript variant 5), CD19, LOC100133583, C-C motif chemokine receptor 6 (CCR6), LOC642934, LOC100132727, LOC90925, pyrophosphatase (inorganic) 2 (PPA2), LOC100130053, sulfotransferase family cytosolic 1A phenol-preferring member 4 (SULT1A4), FCRLA, cell division cycle 42 (CDC42), ceramide kinase (CERK), succinate dehydrogenase complex subunit A flavoprotein pseudogene 1 (SDHALP1), LOC100129237, HINT3, SULT1A1 (transcript variant 3), SULT1A2, cytidine monophosphate (UMP-CMP) kinase 1 cytosolic (CMPK1), myocyte enhancer factor 2D (MEF2D), anaphase promoting complex subunit 16 (C10ORF104), Janus kinase 1 (JAK1), LOC644739, *Homo sapiens* cDNA clone UI-H-FH1-bfi-p-18-0-UI 3-(HS.552082), potassium voltage-gated channel subfamily H (eag-related) member 6 (KCNH6), ribosomal protein L37a (RPL37A), CDK5RAP3, F113580, fibulin 1 (FBLN1), CKS2, *Homo sapiens* chromosome 10 open reading frame 105 (C10ORF105), CDCA7, *Homo sapiens* ring finger protein 36 (HS.489254), MYC associated factor X (MAX), GINS complex subunit 2 (Psf2 homolog) (GINS2), minichromosome maintenance complex component 4 (MCM4), LOC648729, TATDN3, myeloid differentiation primary response gene (88) (MYD88), leptin receptor overlapping transcript (LEPROT), LOC645159, methionine sulfoxide reductase A (MSRA), TPM4, N-acetyltransferase 8B (putative, gene/pseudogene) (NAT8B), receptor transporter protein 4 (RTP4), GRB2, SUMO3, RPS15A, multiple C2 domains transmembrane 1 (MCTP1), LOC642678, protein S (alpha) (PROS1), nuclear factor of kappa light polypeptide gene enhancer in B-cells inhibitor zeta (NFKBIZ), poly (ADP-ribose) polymerase family member 12 (PARP12), OSBPL8, SPATA13, LIMS1, heme binding protein 1 (HEBP1), histone cluster 1 H4 family member h (HIST1H4H), LOC441763, lymphocyte antigen 6 complex locus E (LY6E), and LOC100008588 mRNA in the blood sample from the human subject; and comparing the level of MYOM2, SLC4A1, LOC402251, LOC286444, FBXO7, TCL1A, LOC100130562, C5ORF28, LOC642989, CD79B, LOC643873, LOC100129742, VPREB3, LOC100133372, RPL13, SULT1A1 (transcript variant 5), CD19, LOC100133583, CCR6, LOC642934, LOC100132727, LOC90925, PPA2, LOC100130053, SULT1A4, FCRLA, CDC42, CERK, SDHALP1, LOC100129237, HINT3, SULT1A1 (transcript variant 3), SULT1A2, CMPK1, MEF2D, C10ORF104, JAK1, LOC644739, HS.552082, KCNH6, RPL37A, CDK5RAP3, FLJ35801, FBLN1, CKS2, C10ORF105, CDCA7, HS.489254, MAX, GINS2, MCM4, LOC648729, TATDN3, MYD88, LEPROT, LOC645159, MSRA, TPM4, NAT8B, RTP4, GRB2, SUMO3, RPS15A, MCTP1, LOC642678, PROS1, NFKBIZ, PARP12, OSBPL8, SPATA13, LIMS1, HEBP1, HIST1H4H, LOC441763, LY6E, and LOC100008588 mRNA to a respective control level of MYOM2, SLC4A1, LOC402251, LOC286444, FBXO7, TCL1A, LOC100130562, C5ORF28, LOC642989, CD79B, LOC643873, LOC100129742, VPREB3, LOC100133372, RPL13, SULT1A1 (transcript variant 5), CD19, CD79B, LOC100133583, CCR6, LOC642934, LOC100132727, LOC90925, PPA2, LOC100130053, SULT1A4, FCRLA, CDC42, CERK, SDHALP1, LOC100129237, HINT3, SULT1A1 (transcript variant 3), SULT1A2, CMPK1, MEF2D, C10ORF104, JAK1, LOC644739, HS.552082, KCNH6, RPL37A, CDK5RAP3, FLJ35801, CKS2, C10ORF105, CDCA7, HS.489254, MAX, GINS2, MCM4, LOC648729, TATDN3, MYD88, LEPROT, LOC645159, MSRA, TPM4, NAT8B, RTP4, GRB2, SUMO3, RPS15A, MCTP1, LOC642678, PROS1, NFKBIZ, PARP12, OSBPL8, SPATA13, LIMS1, HEBP1, HIST1H4H, LOC441763, LY6E, and LOC100008588 mRNA;

detecting a decrease in the level of MYOM2, SLC4A1, LOC402251, LOC286444, FBXO7, TCL1A, LOC100130562, C5ORF28, LOC642989, CD79B, LOC643873, LOC100129742, VPREB3, LOC100133372, RPL13, SULT1A1 (transcript variant 5), CD19, LOC100133583, CCR6, LOC642934, LOC100132727, LOC90925, PPA2, LOC100130053, SULT1A4, FCRLA, CDC42, CERK, SDHALP1, LOC100129237, HINT3, SULT1A1 (transcript variant 3), SULT1A2, CMPK1, MEF2D, C10ORF104, JAK1, LOC644739, HS.552082, KCNH6, RPL37A, CDK5RAP3, and F1135801 mRNA, and an increase in the level of FBLN1, CKS2, C10ORF105, CDCA7, HS.489254, MAX, GINS2, MCM4, LOC648729, TATDN3, MYD88, LEPROT, LOC645159, MSRA, TPM4, NAT8B, RTP4, GRB2, SUMO3, RPS15A, MCTP1, LOC642678, PROS1, NFKBIZ, PARP12, OSBPL8, SPATA13, LIMS1, HEBP1, HIST1H4H, LOC441763, LY6E, and LOC100008588 mRNA, as compared to the respective control.

4. The method of claim 3, wherein the human subject has multiple sexual partners and/or previously has or had one or more sexually transmitted diseases.

5. The method of claim 3, further comprising assessing the clinical risk factors for the human subject.

6. The method of claim 3, comprising performing a polymerase chain reaction, a microarray analysis or a hybridization reaction.

7. The method of claim 6, comprising performing reverse transcriptase polymerase chain reaction (RT-PCR).

8. The method of claim 3, wherein the method determines elevated chlamydial burden in tissue obtained from infection sites.

* * * * *

UNITED STATES PATENT AND TRADEMARK OFFICE
CERTIFICATE OF CORRECTION

PATENT NO. : 10,184,152 B2  
APPLICATION NO. : 15/304836  
DATED : January 22, 2019  
INVENTOR(S) : O'Connell et al.

Page 1 of 1

It is certified that error appears in the above-identified patent and that said Letters Patent is hereby corrected as shown below:

In the Specification

In Column 1, Line 19, "Grant Nos. A1084024-01 and A1098660" should be replaced with --Grant Nos. AI084024 and AI098660--.

Signed and Sealed this
Twenty-seventh Day of August, 2019

Andrei Iancu
*Director of the United States Patent and Trademark Office*